US012668591B2

(12) United States Patent
Carceller González et al.

(10) Patent No.: US 12,668,591 B2
(45) Date of Patent: Jun. 30, 2026

(54) 1,2,4-OXADIAZOLE DERIVATIVES AS HISTONE DEACETYLASE 6 INHIBITORS

(71) Applicant: Oryzon Genomics, S.A., Madrid (ES)

(72) Inventors: Elena Carceller González, Sant Cugat del Vallès (ES); Alberto Ortega Muñoz, Vilassar de Dalt (ES); Jorge Salas Solana, Granollers (ES)

(73) Assignee: ORYZON GENOMICS, S.A., Madrid (ES)

(*) Notice: Subject to any disclaimer, the term of this patent is extended or adjusted under 35 U.S.C. 154(b) by 1148 days.

(21) Appl. No.: 17/650,561

(22) Filed: Feb. 10, 2022

(65) Prior Publication Data

US 2023/0026909 A1 Jan. 26, 2023

Related U.S. Application Data

(63) Continuation of application No. 16/768,931, filed as application No. PCT/EP2018/083655 on Dec. 5, 2018, now abandoned.

(30) Foreign Application Priority Data

Dec. 5, 2017 (EP) .................................... 17382835
Jul. 26, 2018 (EP) .................................... 18382562

(51) Int. Cl.
*C07D 471/04* (2006.01)
*C07D 413/14* (2006.01)

(52) U.S. Cl.
CPC ......... *C07D 471/04* (2013.01); *C07D 413/14* (2013.01)

(58) Field of Classification Search
CPC ............................ C07D 471/04; C07D 413/14
See application file for complete search history.

(56) References Cited

U.S. PATENT DOCUMENTS

| | | | | |
|---|---|---|---|---|
| 10,081,624 | B2 | 9/2018 | Kaieda et al. | |
| 10,357,484 | B2 | 7/2019 | Kaieda et al. | |
| 10,406,146 | B2 | 9/2019 | Kaieda et al. | |
| 2010/0136024 | A1* | 6/2010 | Bartels ................. | A61K 31/713 530/389.1 |
| 2020/0339569 | A1 | 10/2020 | Carceller Gonzalez et al. | |
| 2022/0298156 | A1 | 9/2022 | Carceller Gonzalez et al. | |

FOREIGN PATENT DOCUMENTS

| | | |
|---|---|---|
| BR | 112014012815 | 6/2017 |
| CN | 103998446 | 8/2014 |
| EA | 201390711 | 3/2014 |
| EP | 1870401 | 12/2007 |
| JP | 2014/533721 | 12/2014 |
| WO | WO2006/109817 | 10/2006 |
| WO | WO2012/068109 | 5/2012 |
| WO | WO2013/066839 | 5/2013 |
| WO | WO2013/080120 | 6/2013 |
| WO | WO2016/031815 | 3/2016 |
| WO | WO2017/014170 | 1/2017 |
| WO | WO2017/014321 | 1/2017 |
| WO | WO2017/033946 | 3/2017 |
| WO | WO2017/161033 | 9/2017 |
| WO | WO2017/222950 | 12/2017 |
| WO | WO2017/222951 | 12/2017 |
| WO | WO2017/222952 | 12/2017 |
| WO | WO2018/118781 | 6/2018 |

OTHER PUBLICATIONS

Academic.ru, official terminology, "pharmaceutical composition", captured in the Internet Archive (Wayback Machine) on Dec. 4, 2013 (https://web.archive.org/web/20131204144425/https://official.academic.ru/28407/Фармацевтическая _композиция ).
Belikov, V.G.: "Pharmaceutical Chemistry", Chapter 2.6 "The relationship between the chemical structure, the properties of substances and their effect on the body", Moscow, MEDpress-inform, 2007, p. 27-29.
Berge, S.M. et al.: "Pharmaceutical Salts", *J Pharm Sci*, 1977, 66(1), 1-19, doi:10.1002/jps.2600660104.
Budchanov, Y.I.: "Transplantation Immunology", Manual for Students, 2012, p. 18.
Wikipedia, entry on "Autoimmune diseases" (Russian language version), captured in the Internet Archive (Wayback Machine) on Feb. 22, 2006 (https://web.archive.org/web/20060222180704/https://ru.wikipedia.org/wiki/Аутоиммунные_заболев ания ).
Wikipedia, entry on "Cardiovascular diseases" (Russian language version), captured in the Internet Archive (Wayback Machine) on Nov. 12, 2011 (https://web.archive.org/web/20111112151547/https://ru.wikipedia.org/wiki/Сердечно- сосудистые заболевания ).
Wikipedia, entry on "Category:Diseases of the central nervous system" (Russian language version), captured in the Internet Archive (Wayback Machine) on Sep. 13, 2006 (https://web.archive.org/web/20060913000000/https://ru.wikipedia.org/wiki/Категория:Заболевания _центральной_нервной_системы ).
Wikipedia, entry on "Ciliopathies" (Russian language version), captured in the Internet Archive (Wayback Machine) on Oct. 19, 2015 (https://web.archive.org/web/20151019031428/https://ru.wikipedia.org/wiki/Цилиопатии) ).
Wikipedia, entry on "Infectious diseases" (Russian language version), captured in the Internet Archive (Wayback Machine) on Jun. 21, 2006 (https://web.archive.org/web/20060621100102/https://ru.wikipedia.org/wiki/Инфекционные_заболев ания ).

(Continued)

*Primary Examiner* — Kamal A Saeed
*Assistant Examiner* — Quincy McKoy
(74) *Attorney, Agent, or Firm* — FINNEGAN, HENDERSON, FARABOW, GARRETT & DUNNER, LLP

(57) ABSTRACT

The invention relates to compounds of Formula (I) as described herein, useful as histone deacetylase 6 (HDAC6) inhibitors. The invention also relates to pharmaceutical compositions comprising these compounds and to their use in therapy.

22 Claims, No Drawings

(56) References Cited

OTHER PUBLICATIONS

Wikipedia, entry on "Malignant tumor" (Russian language version), captured in the Internet Archive (Wayback Machine) on Jan. 15, 2006 (https://web.archive.org/web/20060115150816/https://ru.wikipedia.org/wiki/Злокачественная_опухо ль ).

Wikipedia, entry on "Mental disorder" (Russian language version), captured in the Internet Archive (Wayback Machine) on Sep. 13, 2006 (https://web.archive.org/web/20060913000000/https://ru.wikipedia.org/wiki/ /Психическое_расстройст во ).

International Search Report and Written Opinion of the International Searching Authority for International Application No. PCT/EP2018/083655.

* cited by examiner

1,2,4-OXADIAZOLE DERIVATIVES AS HISTONE DEACETYLASE 6 INHIBITORS

This application is a continuation of application Ser. No. 16/768,931, filed Jun. 2, 2020, which is a national stage filing under 35 U.S.C. § 371 of International Application No. PCT/EP2018/083655, filed on Dec. 5, 2018, which claims benefit of European Patent Application Nos. 17382835.1, filed on Dec. 5, 2017, and European Patent Application No. 18382562.9, filed on Jul. 26, 2018, all of which are incorporated herein by reference.

TECHNICAL FIELD

The invention relates to 1,2,4-oxadiazole derivatives useful as histone deacetylase 6 inhibitors. The invention also relates to pharmaceutical compositions comprising these compounds and to their use in therapy.

BACKGROUND

Histone deacetylases (HDACs) are part of a large family of enzymes that catalyze the removal of acetyl group from histones and non-histone proteins. HDACs have crucial roles in numerous biological processes, largely through their repressive influence on transcription. In humans, there are four classes of HDACs which include a total of 18 proteins: class I HDACs are HDAC1, HDAC2, HDAC3 and HDAC8; class II HDACs are HDAC4, HDAC5, HDAC6, HDAC7, HDAC9 and HDAC10; class III HDACs are Sir2-like proteins SIRT1, SIRT2, SIRT3, SIRT4, SIRT5, SIRT6 and SIRT7; and class IV HDACs, which is HDAC11. The class II enzymes are further divided into two subclasses, class IIa (HDAC4, HDAC5, HDAC7 and HDAC9) and class IIb (HDAC6 and HDAC10).

Histone deacetylase 6 (HDAC6) catalyzes primarily the deacetylation of non-histone substrates such as alpha-tubulin, heat shock protein (Hsp)90 and cortactin.

HDAC6 activity has been reported to be involved in several pathological conditions, including cancer, neurological, ciliopathic, infectious, cardiovascular, infectious and immune and inflammatory diseases, as discussed in more detail below. HDAC6 inhibitors have thus emerged as an attractive therapeutic approach to treat a broad spectrum of diseases.

Many of the HDAC inhibitors currently in development are pan-HDAC inhibitors, which are non-selective against different HDAC isoforms. Pan-HDAC inhibitors are known to exhibit significant side effects; in particular, toxic side effects have been associated with inhibition of certain HDAC class I isoforms, particularly HDAC1 and HDAC2.

It would be advantageous to identify HDAC inhibitors that inhibit one or more, but not all HDAC isoforms, and in particular compounds that inhibit HDAC6 while not inhibiting or inhibiting to a much lower extent HDAC1 or HDAC2.

SUMMARY OF THE INVENTION

In one aspect, the present invention provides a compound of Formula (I) as described below or a salt thereof:

(I)

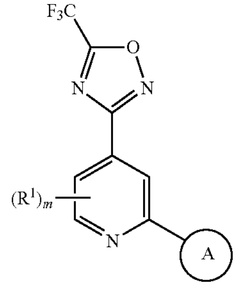

wherein m is 0, 1 or 2;

each $R^1$ is independently selected from halo, methyl and trifluoromethyl;

A is selected from:

i) a 5- or 6-membered monocyclic or 9- or 10-membered bicyclic heteroaryl ring that is fully aromatic, and ii) a 9- or 10-membered bicyclic heteroaryl ring consisting of a 5- or 6-membered monocyclic heteroaryl ring fused to a saturated or partially unsaturated carbocyclic or heterocyclic ring, wherein the 9- or 10-membered bicyclic heterocyclic ring is linked to the rest of the molecule through the 5- or 6-membered monocyclic heteroaryl ring, wherein A contains one ring N atom at a position adjacent to the ring atom through which ring A is attached to the rest of the molecule, wherein A optionally contains from 1 to 3 additional ring heteroatoms selected independently from N, O and S, and wherein A is optionally substituted with one or two $R^2$ and in addition A is optionally substituted with one $R^3$; each $R^2$ is independently selected from halo, $C_{1-6}$ alkyl, $C_{1-6}$ haloalkyl, $C_{3-7}$ cycloalkyl and —($C_{1-6}$ alkylene)-$OR^4$; $R^3$ is selected from -$L^1$-$R^5$, -$L^2$-$OR^6$, -$L^3$-$NR^7R^8$, -$L^4$-$CONR^9R^1$, -$L^5$-$NR^{11}COR^{12}$, —Y-$L^6$-$OR^6$ and —Y-$L^7$-$NR^7R^6$; $L^1$, $L^2$, $L^3$, $L^4$ and $L^5$ are each independently selected from a bond and $C_{1-6}$ alkylene;

$L^6$ and $L^7$ are each independently selected from $C_{2-6}$ alkylene;

each Y is independently selected from —O—, —$NR^{13}$—, —$CONR^{14}$— and —$NR^{15}CO$—;

each $R^4$ is independently selected from hydrogen, $C_{1-6}$ alkyl, $C_{1-6}$ haloalkyl, $C_{3-7}$ cycloalkyl and $C_{3-7}$ cycloalkyl-$C_{1-6}$ alkyl;

each $R^5$ is independently selected from carbocyclyl, aryl, heterocyclyl and heteroaryl, wherein the carbocyclyl, the aryl, the heterocyclyl and the heteroaryl are each optionally substituted with one or more $R^{16}$; $R^6$ and $R^{12}$ are each independently selected from hydrogen, $C_{1-6}$ alkyl, $C_{1-6}$ haloalkyl and -$L^1$-$R^5$;

$R^7$ and $R^8$ are each independently selected from hydrogen, $C_{1-6}$ alkyl, $C_6$ haloalkyl, —($C_{1-6}$ alkylene)-$OR^4$ and -$L^1$-$R^5$;

$R^9$ and $R^{10}$ are each independently selected from hydrogen, $C_{1-6}$ alkyl, $C_{1-6}$ haloalkyl, —($C_{1-6}$ alkylene)-$OR^4$ and -$L^1R^5$, or $R^9$ and $R^{10}$ taken together with the N atom to which they are attached form a saturated 4- to 12-membered heterocyclic ring optionally containing one additional heteroatom selected from N, O and S, wherein said heterocyclic ring is optionally substituted with one or more $R^{16}$—;

$R^{11}$, $R^{13}$, $R^{14}$ and $R^{15}$ are each independently selected from hydrogen, $C_{1-6}$ alkyl, $C_{1-6}$ haloalkyl, $C_{3-7}$ cycloalkyl, $C_{3-7}$ cycloalkyl-$C_{1-6}$ alkyl and —($C_{1-6}$ alkylene)-$OR^4$—;

each $R^{16}$ is independently selected from $C_{1-6}$ alkyl, $C_{1-6}$ haloalkyl, halo, $C_{1-6}$ alkoxy, $C_{1-6}$ haloalkoxy, —OH, —$NR^{17}R^{18}$, —$COR^{19}$, —CN, -$L^8$-carbocyclyl, -$L^8$-aryl, -$L^8$-heterocyclyl and -$L^8$-heteroaryl, wherein the carbocyclyl in -$L^8$-carbocyclyl, the aryl in -$L^8$-aryl, the heterocyclyl in -$L^8$-heterocyclyl and the heteroaryl in -$L^8$-heteroaryl are each optionally substituted with one or more $R^{20}$;

each $L^8$ is independently selected from a bond and $C_{1-6}$ alkylene;

$R^{17}$ and $R^{18}$ are each independently selected from hydrogen, $C_{1-6}$ alkyl, $C_6$ haloalkyl, $C_{3-7}$ cycloalkyl and $C_{3-7}$ cycloalkyl-$C_{1-6}$ alkyl;

$R^{19}$ is selected from hydrogen, $C_{1-6}$ alkyl and $C_{1-6}$ haloalkyl; and each $R^{20}$ is independently selected from $C_{1-6}$ alkyl, $C_{1-6}$ haloalkyl, halo, $C_{1-6}$ alkoxy, $C_{1-6}$ haloalkoxy, —OH, —$NR^{17}R^{18}$, —$COR^9$ and —CN.

The compounds of Formula (I) as described herein are inhibitors of HDACs, particularly HDAC6. These compounds, and pharmaceutical compositions comprising these compounds, are useful for the treatment of diseases associated with HDAC6. For example, the disease is cancer, an autoimmune or inflammatory disease, transplant rejection, a ciliopathy, a disease of the nervous system, a mental or behavioral disorder, an infectious disease, a cardiovascular disease, muscle atrophy or cachexia.

The present invention further provides a pharmaceutical composition comprising a compound of Formula (I), or a pharmaceutically acceptable salt thereof, and a pharmaceutically acceptable carrier.

The present invention further provides a compound of Formula (I), or a pharmaceutically acceptable salt thereof, for use as a medicament.

The present invention further provides a compound of Formula (I), or a pharmaceutically acceptable salt thereof, or a pharmaceutical composition comprising said compound and a pharmaceutically acceptable carrier, for use in the treatment of a disease associated with HDAC6.

The present invention further provides the use of a compound of Formula (I), or a pharmaceutically acceptable salt thereof, for the manufacture of a medicament for the treatment of a disease associated with HDAC6.

The present invention further provides the use of a compound of Formula (I), or a pharmaceutically acceptable salt thereof, for treating a disease associated with HDAC6.

The present invention further provides a compound of Formula (I), or a pharmaceutically acceptable salt thereof, for use as a HDAC6 inhibitor.

The present invention further provides a method for treating a disease associated with HDAC6, comprising administering a therapeutically effective amount of a compound of Formula (I), or a pharmaceutically acceptable salt thereof, to a patient in need thereof.

The present invention further provides a method of inhibiting HDAC6 activity, comprising administering to a patient in need of said treatment an amount of a compound of Formula (I), or a pharmaceutically acceptable salt thereof, sufficient to inhibit HDAC6 activity.

The present invention further provides a compound of Formula (I), or a pharmaceutically acceptable salt thereof, or a pharmaceutical composition comprising said compound and a pharmaceutically acceptable carrier, for use in the treatment of a disease selected from cancer, an autoimmune or inflammatory disease, transplant rejection, a ciliopathy, a disease of the nervous system, a mental or behavioral disorder, an infectious disease, a cardiovascular disease, muscle atrophy and cachexia.

The present invention further provides the use of a compound of Formula (I), or a pharmaceutically acceptable salt thereof, for the manufacture of a medicament for the treatment of a disease selected from cancer, an autoimmune or inflammatory disease, transplant rejection, a ciliopathy, a disease of the nervous system, a mental or behavioral disorder, an infectious disease, a cardiovascular disease, muscle atrophy and cachexia.

The present invention further provides the use of a compound of Formula (I), or a pharmaceutically acceptable salt thereof, for treating a disease selected from cancer, an autoimmune or inflammatory disease, transplant rejection, a ciliopathy, a disease of the nervous system, a mental or behavioral disorder, an infectious disease, a cardiovascular disease, muscle atrophy and cachexia.

The present invention further provides a method for treating a disease selected from cancer, an autoimmune or inflammatory disease, transplant rejection, a ciliopathy, a disease of the nervous system, a mental or behavioral disorder, an infectious disease, a cardiovascular disease, muscle atrophy and cachexia, comprising administering a therapeutically effective amount of a compound of Formula (I), or a pharmaceutically acceptable salt thereof, to a patient in need thereof.

DETAILED DESCRIPTION OF THE INVENTION

The present invention provides a compound of Formula (I) or a salt thereof:

(I)

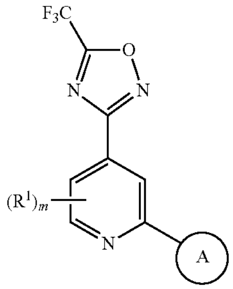

wherein m is 0, 1 or 2;

each $R^1$ is independently selected from halo, methyl and trifluoromethyl;

A is selected from:

i) a 5- or 6-membered monocyclic or 9- or 10-membered bicyclic heteroaryl ring that is fully aromatic, and ii) a 9- or 10-membered bicyclic heteroaryl ring consisting of a 5- or 6-membered monocyclic heteroaryl ring fused to a saturated or partially unsaturated carbocyclic or heterocyclic ring, wherein the 9- or 10-membered bicyclic heterocyclic ring is linked to the rest of the molecule through the 5- or 6-membered monocyclic heteroaryl ring, wherein A contains one ring N atom at a position adjacent to the ring atom through which ring A is attached to the rest of the molecule, wherein A optionally contains from 1 to 3 additional ring heteroatoms selected independently from N, O and S, and wherein A is optionally substituted with one or two $R^2$ and in addition A is optionally substituted with one $R^3$;

each $R^2$ is independently selected from halo, $C_{1-6}$ alkyl, $C_{1-6}$ haloalkyl, $C_{3-7}$ cycloalkyl and —($C_{1-6}$ alkylene)-$OR^4$;

$R^3$ is selected from -$L^1$-$R^5$, -$L^2$-$OR^6$, -$L^3$-$NR^7R^8$, -$L^4$-$CONR^9R^{10}$, -$L^5$-$NR^{11}COR^{12}$, -Y-$L^6$-$OR^6$ and -Y-$L^7$-$NR^7R^8$;

$L^1$, $L^2$, $L^3$, $L^4$ and $L^5$ are each independently selected from a bond and $C_{1-6}$ alkylene;

$L^6$ and $L^7$ are each independently selected from $C_{2-6}$ alkylene;

each Y is independently selected from —O—, —$NR^{13}$—, —$CONR^{14}$— and —$NR^{15}CO$—;

each $R^4$ is independently selected from hydrogen, $C_{1-6}$ alkyl, $C_{1-6}$ haloalkyl, $C_{3-7}$ cycloalkyl and $C_{3-7}$ cycloalkyl-$C_{1-6}$ alkyl;

each $R^5$ is independently selected from carbocyclyl, aryl, heterocyclyl and heteroaryl, wherein the carbocyclyl, the aryl, the heterocyclyl and the heteroaryl are each optionally substituted with one or more $R^{16}$; $R^6$ and $R^{12}$ are each independently selected from hydrogen, $C_{1-6}$ alkyl, $C_{1-6}$ haloalkyl and -$L^1$-$R^5$;

$R^7$ and $R^8$ are each independently selected from hydrogen, $C_{1-6}$ alkyl, $C_{1-6}$ haloalkyl, —($C_{1-6}$ alkylene)-$OR^4$ and -$L^1$-$R^5$;

$R^9$ and $R^{10}$ are each independently selected from hydrogen, $C_{1-6}$ alkyl, $C_{1-6}$ haloalkyl, —($C_{1-6}$ alkylene)-$OR^4$ and -$L^1$-$R^5$, or $R^9$ and $R^{10}$ taken together with the N atom to which they are attached form a saturated 4- to 12-membered heterocyclic ring optionally containing one additional heteroatom selected from N, O and S, wherein said heterocyclic ring is optionally substituted with one or more $R^{16}$;

$R^{11}$, $R^{13}$, $R^{14}$ and $R^{15}$ are each independently selected from hydrogen, $C_{1-6}$ alkyl, $C_{1-6}$ haloalkyl, $C_{3-7}$ cycloalkyl, $C_{3-7}$ cycloalkyl-$C_{1-6}$ alkyl and —($C_{1-6}$ alkylene)-$OR^4$;

each $R^{16}$ is independently selected from $C_{1-6}$ alkyl, $C_{1-6}$ haloalkyl, halo, $C_{1-6}$ alkoxy, $C_{1-6}$ haloalkoxy, —OH, —$NR^{17}R^{18}$, —$COR^{19}$, —CN, -$L^8$-carbocyclyl, -$L^8$-aryl, -$L^8$-heterocyclyl and -$L^8$-heteroaryl, wherein the carbocyclyl in -$L^8$-carbocyclyl, the aryl in -$L^8$-aryl, the heterocyclyl in -$L^8$-heterocyclyl and the heteroaryl in -$L^8$-heteroaryl are each optionally substituted with one or more $R^{20}$;

each $L^8$ is independently selected from a bond and $C_{1-6}$ alkylene; $R^{17}$ and $R^{18}$ are each independently selected from hydrogen, $C_{1-6}$ alkyl, $C_{1-6}$ haloalkyl, $C_{3-7}$ cycloalkyl and $C_{3-7}$ cycloalkyl-$C_{1-6}$ alkyl;

$R^{19}$ is selected from hydrogen, $C_{1-6}$ alkyl and $C_{1-6}$ haloalkyl; and each $R^{20}$ is independently selected from $C_{1-6}$ alkyl, $C_{1-6}$ haloalkyl, halo, $C_{1-6}$ alkoxy, $C_{1-6}$ haloalkoxy, —OH, —$NR^{17}R^{18}$, —$COR^{19}$ and —CN.

Embodiments of the present invention are outlined in the following paragraphs. Each of the embodiments described below can be combined with any other embodiment described herein that is not inconsistent with the embodiment with which it is combined.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic administration to a subject).

Furthermore, each of the embodiments described herein envisions within its scope the salts (for example pharmaceutically acceptable salts) of the compounds described herein. Accordingly, the phrase "or a salt thereof" (including also "or a pharmaceutically acceptable salt thereof") is implicit in the description of all compounds described herein. The invention also specifically relates to all compounds described herein in non-salt form.

In a compound of Formula (I) each $R^1$ is independently selected from halo, methyl and trifluoromethyl, and preferably each $R^1$ is fluoro. It will be understood that each substituent $R^1$ can be placed at any available ring C atom of the pyridine ring to which $R^1$ is attached.

Preferably, in a compound of Formula (I) m is 0.

In a compound of Formula (I), A is a cyclic group selected from:

i) a 5- or 6-membered monocyclic or 9- or 10-membered bicyclic heteroaryl ring that is fully aromatic, and ii) a 9- or 10-membered bicyclic heteroaryl ring consisting of a 5- or 6-membered monocyclic heteroaryl ring fused to a saturated or partially unsaturated carbocyclic or heterocyclic ring, wherein the 9- or 10-membered bicyclic heterocyclic ring is linked to the rest of the molecule through the 5- or 6-membered monocyclic heteroaryl ring, wherein A contains one ring N atom at a position adjacent to the ring atom through which ring A is attached to the rest of the molecule, wherein A optionally contains from 1 to 3 additional ring heteroatoms selected independently from N, O and S (and wherein all remaining ring atoms of A are carbon atoms), and wherein A is optionally substituted with one or two $R^2$ and in addition A is optionally substituted with one $R^3$. It will be understood that ring A can be attached to the rest of the molecule via a ring C atom or a ring N atom of A.

It will be understood that each substituent $R^2$ or $R^3$ which is attached to ring A can be placed at any available ring atom. In particular, any substituent $R^2$ or $R^3$ (if present) can be attached to a ring C atom or a ring N atom of A. It will further be understood that if ring A is a bicyclic ring, the substituent(s) $R^2$ and/or $R^3$ can each be attached to any available ring atom (e.g., any available ring C atom or any available ring N atom) of any one of the rings constituting the bicyclic ring group A. For example, if ring A is a bicyclic ring, the one or two optional substituents $R^2$ (if present) and the optional substituent $R^3$ (if present) may be attached to the ring that does not contain the ring atom through which A is attached to the rest of the molecule, or said optional substituent(s) may be attached to the ring that contains the ring atom through which A is attached to the rest of the molecule, or the respective optional substituents may be attached to both rings constituting the bicyclic ring group A. Moreover, it will be understood that the one or two optional substituents $R^2$ (if present) and the optional substituent $R^3$ (if present) are typically each attached to a different ring atom of A. The attachment of two of these optional substituents to the same ring atom of A is possible only if the corresponding ring atom has enough available attachment sites. For example, if A is a 2,3-dihydro-1H-pyrrolo[3,2-c]pyridin-6-yl ring (which is composed of a pyridine ring fused to a pyrrolidine ring), a ring atom —$CH_2$— of the pyrrolidine moiety of the 2,3-dihydro-1H-pyrrolo[3,2-c]pyridin-6-yl ring may be substituted by two of the aforementioned optional substituents (e.g., by two substituents $R^2$, resulting in a ring atom —$C(R^2)(R^2)$—, or by one substituent $R^2$ and one substituent $R^3$, resulting in a ring atom —$C(R^2)(R^3)$—).
Non-limiting examples of cyclic groups A include the groups listed in Table 1 below, and any tautomeric form thereof:
TABLE 1
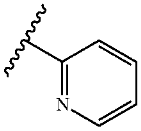 [SMILES: *c1ccccn1]
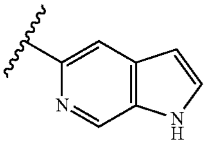 [SMILES: *c1cc2cc[nH]c2cn1]
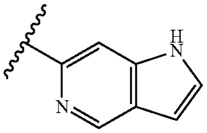 [SMILES: *c1cc2[nH]ccc2cn1]
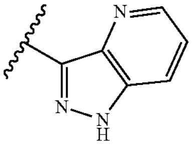 [SMILES: *c1n[nH]c2cccnc12]
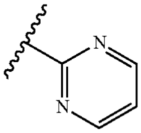 [SMILES: *c1ncccn1]
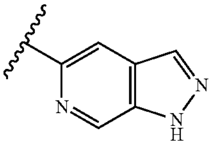
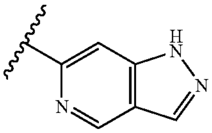 [SMILES: *c1cc2[nH]ncc2cn1]
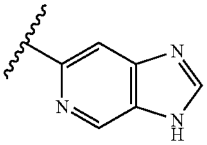 [SMILES: *c1cc2nc[nH]c2cn1]
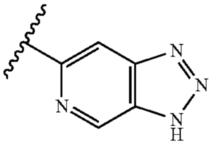 [SMILES: *c1cc2nn[nH]c2cn1]
TABLE 1-continued
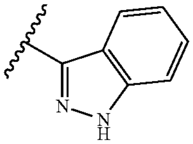 [SMILES: *c1n[nH]c2ccccc12]
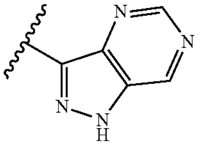 [SMILES: *c1n[nH]c2cncnc12]
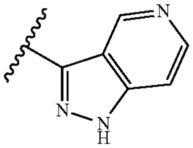 [SMILES: *c1n[nH]c2ccncc12]
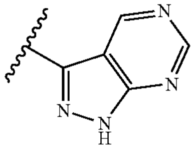 [SMILES: *c1n[nH]c2ncncc12]
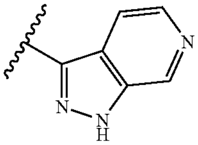 [SMILES: *c1n[nH]c2cnccc12]
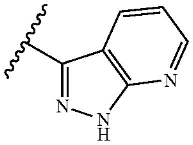 [SMILES: *c1n[nH]c2ncccc12]
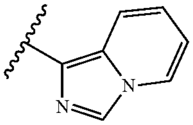
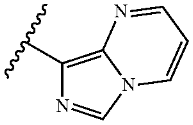 [SMILES: *c1ncn2cccnc12]
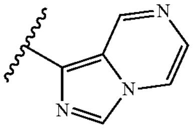 [SMILES: *c1ncn2ccncc12]
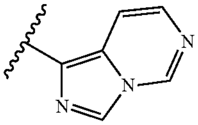 [SMILES: *c1ncn2cnccc12]

TABLE 1-continued
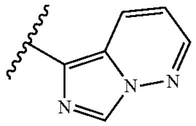 [SMILES: *c1ncn2ncccc12]
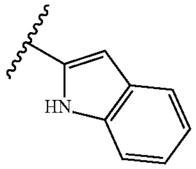 [SMILES: *c1cc2ccccc2[nH]1]
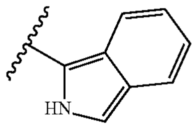 [SMILES: *c1[nH]cc2ccccc12]
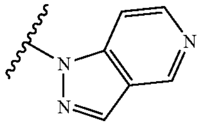 [SMILES: *n1ncc2cnccc21]
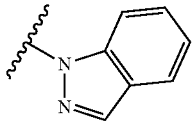 [SMILES: *n1ncc2ccccc21]
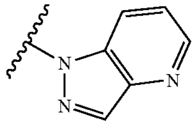 [SMILES: *n1ncc2ncccc21]
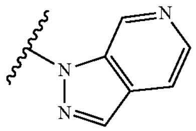 [SMILES: *n1ncc2ccncc21]
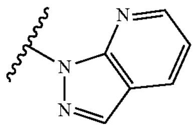 [SMILES: *n1ncc2cccnc21]
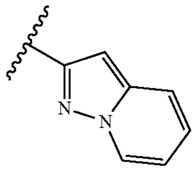 [SMILES: *c1cc2ccccn2n1]
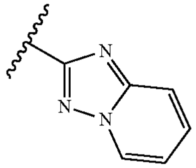 [SMILES: *c1nc2ccccn2n1]
TABLE 1-continued
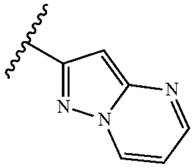 [SMILES: *c1cc2ncccn2n1]
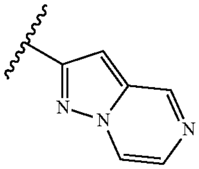 [SMILES: *c1cc2cnccn2n1]
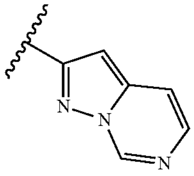 [SMILES: *c1cc2ccncn2n1]
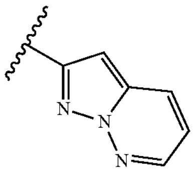 [SMILES: *c1cc2cccnn2n1]
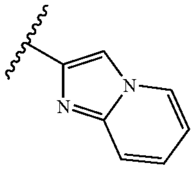 [SMILES: *c1cn2ccccc2n1]
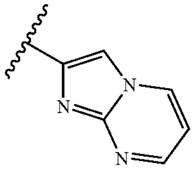 [SMILES: *c1cn2cccnc2n1]
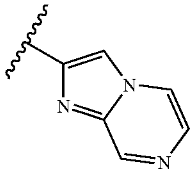 [SMILES: *c1cn2ccncc2n1]
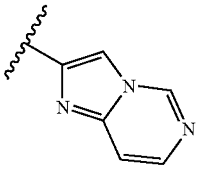 [SMILES: *c1cn2cnccc2n1]
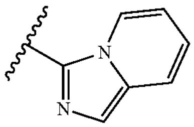 [SMILES: *c1ncc2ccccn12]

TABLE 1-continued
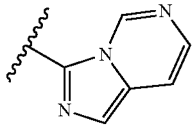 [SMILES: *c1ncc2ccncn12]
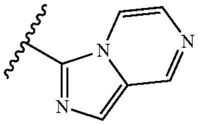 [SMILES: *c1ncc2cnccn12]
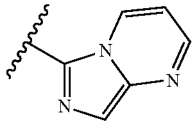 [SMILES: *c1ncc2ncccn12]
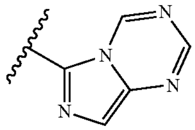 [SMILES: *c1ncc2ncncn12]
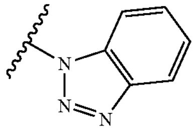 [SMILES: *n1nnc2ccccc21]
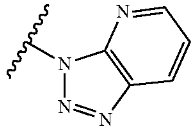 [SMILES: *n1nnc2cccnc21]
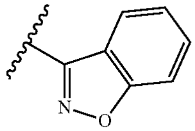
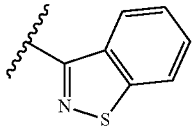 [SMILES: *c1nsc2ccccc12]
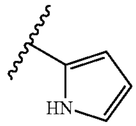 [SMILES: *c1ccc[nH]1]
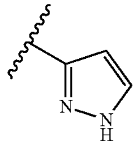 [SMILES: *c1cc[nH]n1]
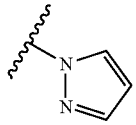 [SMILES: *n1cccn1]
TABLE 1-continued
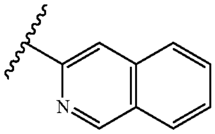 [SMILES: *c1cc2ccccc2cn1]
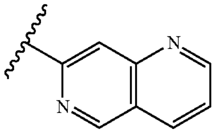 [SMILES: *c1cc2ncccc2cn1]
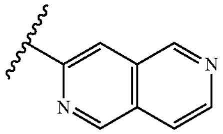 [SMILES: *c1cc2cnccc2cn1]
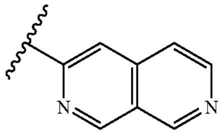 [SMILES: *c1cc2ccncc2cn1]
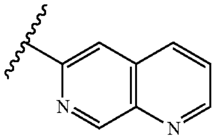 [SMILES: *c1cc2cccnc2cn1]
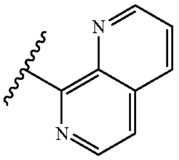 [SMILES: *c1nccc2cccnc12]
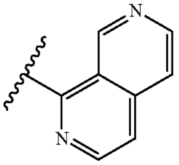 [SMILES: *c1nccc2ccncc12]
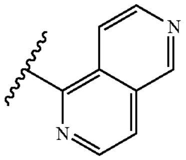 [SMILES: *c1nccc2cnccc12]
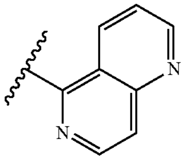 [SMILES: *c1nccc2ncccc12]
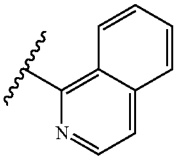 [SMILES: *c1nccc2ccccc12]

TABLE 1-continued
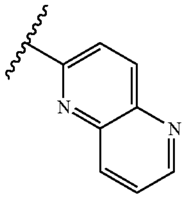 [SMILES: *c1ccc2ncccc2n1]
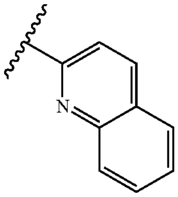 [SMILES: *c1ccc2ccccc2n1]
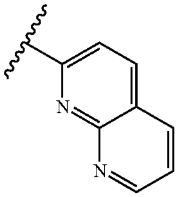 [SMILES: *c1ccc2cccnc2n1]
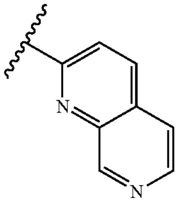 [SMILES: *c1ccc2ccncc2n1]
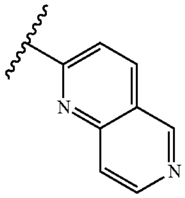 [SMILES: *c1ccc2cnccc2n1]
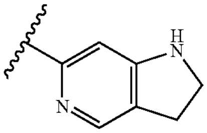 [SMILES: *c1cc2c(cn1)CCN2]
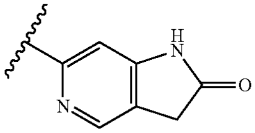 [SMILES: *c1cc2c(cn1)CC(=O)N2]
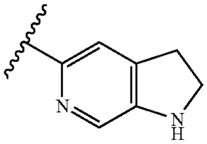 [SMILES: *c1cc2c(cn1)NCC2]
TABLE 1-continued
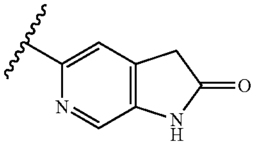 [SMILES: *c1cc2c(cn1)NC(=O)C2]
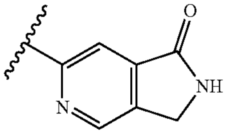 [SMILES: *c1cc2c(cn1)CNC2=O]
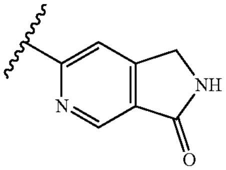 [SMILES: *c1cc2c(cn1)C(=O)NC2]
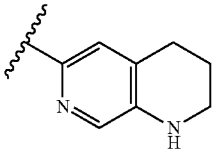 [SMILES: *c1cc2c(cn1)NCCC2]
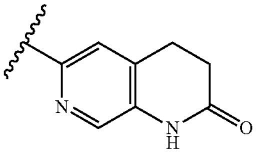 [SMILES: *c1cc2c(cn1)NC(=O)CC2]
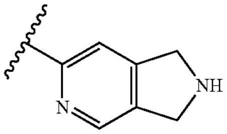 [SMILES: *c1cc2c(cn1)CNC2]
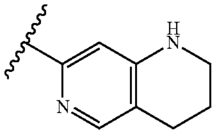 [SMILES: *c1cc2c(cn1)CCCN2]
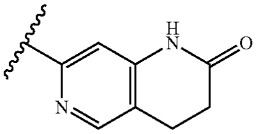 [SMILES: *c1cc2c(cn1)CCC(=O)N2]
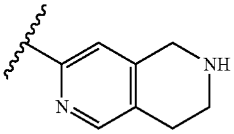 [SMILES: *c1cc2c(cn1)CCNC2]
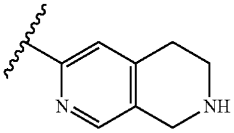 [SMILES: *c1cc2c(cn1)CNCC2]

TABLE 1-continued
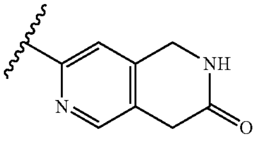 [SMILES: *c1cc2c(cn1)CC(=O)NC2]
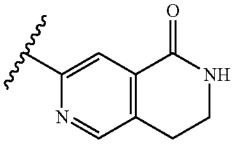 [SMILES: *c1cc2c(cn1)CCNC2=O]
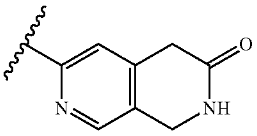 [SMILES: *c1cc2c(cn1)CNC(=O)C2]
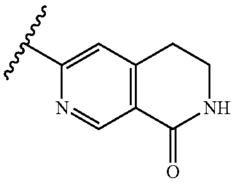 [SMILES: *c1cc2c(cn1)C(=O)NCC2]
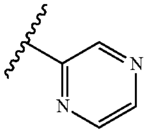 [SMILES: *c1cnccn1]
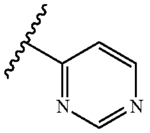 [SMILES: *c1ccncn1]
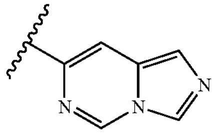 [SMILES: *c1cc2cncn2cn1]
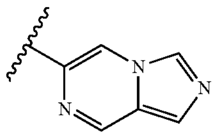 [SMILES: *c1cn2cncc2cn1]
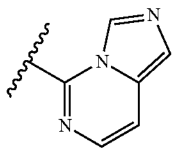 [SMILES: *c1nccc2cncn12]
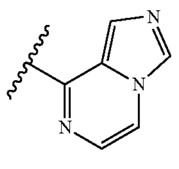 [SMILES: *c1nccn2cncc12]
TABLE 1-continued
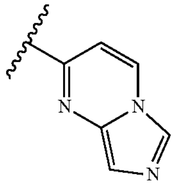 [SMILES: *c1ccn2cncc2n1]
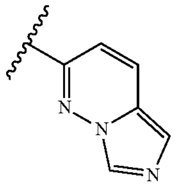 [SMILES: *c1ccc2cncn2n1]
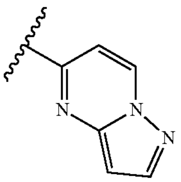 [SMILES: *c1ccn2nccc2n1]
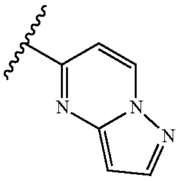 [SMILES: *c1ccn2nccc2n1]
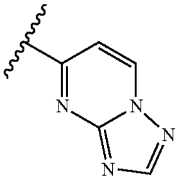 [SMILES: *c1ccn2ncnc2n1]
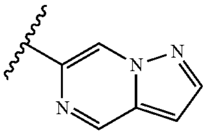 [SMILES: *c1cn2nccc2cn1]
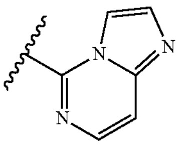 [SMILES: *c1nccc2nccn12]
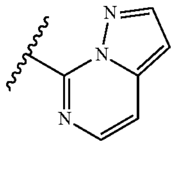 [SMILES: *c1nccc2ccnn12]
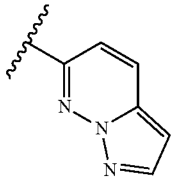 [SMILES: *c1ccc2ccnn2n1]

TABLE 1-continued

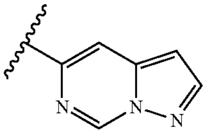 [SMILES: *c1cc2ccnn2cn1]
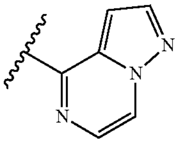 [SMILES: *c1nccn2nccc12]
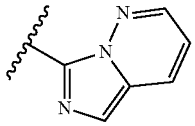 [SMILES: *c1ncc2cccnn12]
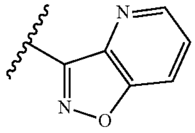 [SMILES: *c1noc2cccnc12]
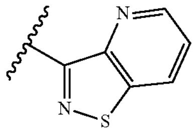 [SMILES: *c1nsc2cccnc12]
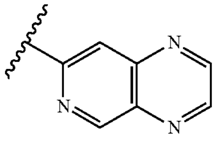 [SMILES: *c1cc2nccnc2cn1]
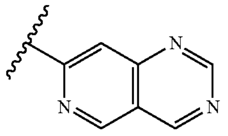 [SMILES: *c1cc2ncncc2cn1]
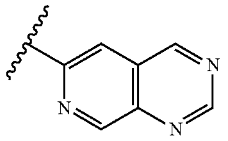 [SMILES: *c1cc2cncnc2cn1]
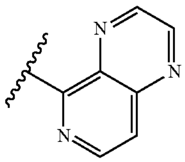 [SMILES: *c1nccc2nccnc12]
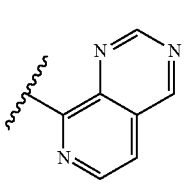 [SMILES: *c1nccc2cncnc12]

TABLE 1-continued

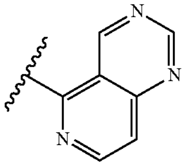 [SMILES: *c1nccc2ncncc12]
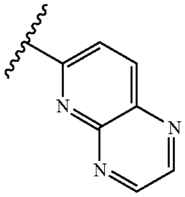 [SMILES: *c1ccc2nccnc2n1]
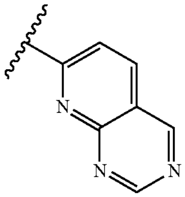 [SMILES: *c1ccc2cncnc2n1]
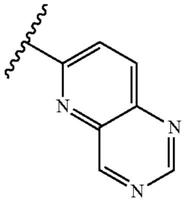 [SMILES: *c1ccc2ncncc2n1]

wherein any of said A groups depicted in Table 1 is optionally substituted with one or two $R^2$ and in addition any of said A is optionally substituted with one $R^3$.

In some embodiments, in a compound of Formula (I), A is selected from the groups listed in Table 1 (including any tautomeric form thereof), wherein A is optionally substituted with one or two $R^2$ and in addition A is optionally substituted with one $R^3$.

Preferably, in a compound of Formula (I), A is selected from:

i) a 5- or 6-membered monocyclic or 9- or 10-membered bicyclic heteroaryl ring that is fully aromatic, and ii) a 9- or 10-membered bicyclic heteroaryl ring consisting of a 5- or 6-membered monocyclic heteroaryl ring fused to a saturated or partially unsaturated carbocyclic or heterocyclic ring, wherein the 9- or 10-membered bicyclic heterocyclic ring is linked to the rest of the molecule through the 5- or 6-membered monocyclic heteroaryl ring, wherein A contains one ring N atom at a position adjacent to the ring atom through which ring A is attached to the rest of the molecule, wherein A optionally contains from 1 to 3, preferably 1 or 2, additional ring N atoms (and wherein all remaining ring atoms of A are carbon atoms), and wherein A is optionally substituted with one or two $R^2$ and in addition A is optionally substituted with one $R^3$.

More preferably, in a compound of Formula (I), A is a 5- or 6-membered monocyclic or 9- or 10-membered bicyclic heteroaryl ring that is fully aromatic, wherein A contains one ring N atom at a position adjacent to the ring atom through which ring A is attached to the rest of the molecule, wherein A optionally contains from 1 to 3, preferably 1 or 2, additional ring N atoms (and wherein all remaining ring atoms of A are carbon atoms), and wherein A is optionally substituted with one or two, preferably one, $R^2$ and in addition A is optionally substituted with one $R^3$.

Still more preferably, in a compound of Formula (I) A is selected rom the cyclic groups listed below:

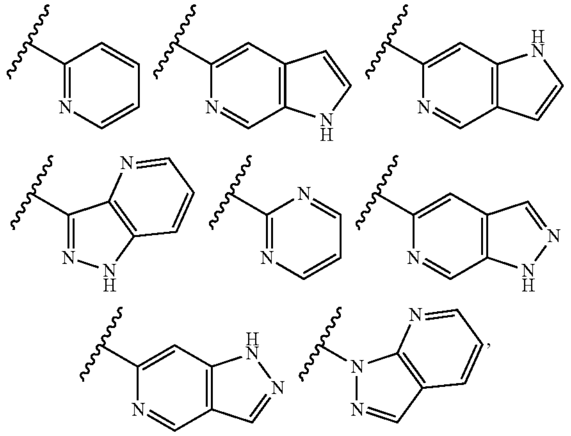

wherein A is optionally substituted with one or two, preferably one, $R^2$ and in addition A is optionally substituted with one $R^3$.

It is particularly preferred that in a compound of Formula (I), A is selected from the cyclic groups listed below:

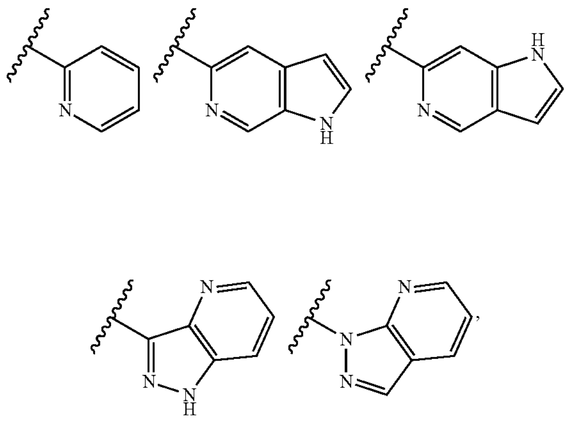

wherein is optionally substituted with one or two, preferably one, $R^2$ and in addition A is optionally substituted with one $R^3$.

In some embodiments, in a compound of Formula (I) A is substituted, i.e. at least one of the optional substituents $R^2$ and/or $R^3$ is present. Said substitutent(s) can be attached to any available ring atom of A (including any available ring N atom), as previously indicated. In some embodiments, in a compound of Formula (I), A is substituted with one $R^3$ and in addition is optionally substituted with one or two (preferably one) $R^2$.

In some other embodiments, in a compound of Formula (I), A is unsubstituted (i.e. A does not have any optional substituent $R^2$ or $R^3$).

In some preferred embodiments, in a compound of Formula (I), A is

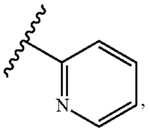

wherein A is optionally substituted with one or two, preferably one, $R^2$ and in addition A is optionally substituted with one $R^3$, wherein it is preferred that A is substituted with one $R^3$ and in addition is optionally substituted with one or two, preferably one, $R^2$. In certain embodiments, A is substituted with one $R^3$ and has no optional substituent(s) $R^2$. Preferably, the substituent $R^3$, if present, is placed at the ring C atom at position 4 or 5 of the pyridyl ring A, according to the numbering indicated in the chemical drawing below:

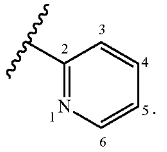 [SMILES: *c1ccccn1]

In some other preferred embodiments, in a compound of Formula (I), A is

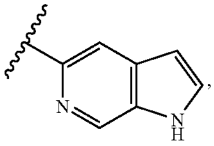

wherein A is optionally substituted with one or two, preferably one, $R^2$ and in addition A is optionally substituted with one $R^3$. Preferably, the one or two optional substituent(s) $R^2$ (if present) and the optional substituent $R^3$ (if present) are attached to the pyrrole ring forming part of ring A. In certain embodiments, A is unsubstituted. More preferably, A is substituted with one $R^3$ and in addition is optionally substituted with one or two, preferably one, $R^2$, wherein the substituent $R^3$ and the one or two optional substituents $R^2$ (if present) are preferably attached to the pyrrole ring forming part of ring A.

In some other referred embodiments, in a compound of Formula (I), A is

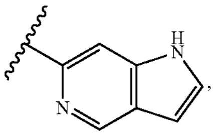

wherein A is optionally substituted with one or two, preferably one, $R^2$ and in addition A is optionally substituted with one $R^3$. Preferably, the one or two optional substituent(s) $R^2$ (if present) and the optional substituent $R^3$ (if present) are attached to the pyrrole ring forming part of ring A. In certain preferred embodiments, A is unsubstituted. In certain other preferred embodiments, A is substituted with one $R^3$ and in addition is optionally substituted with one or two, preferably one, $R^2$, wherein the substituent $R^3$ and the one or two optional substituents $R^2$ (if present) are preferably attached to the pyrrole ring forming part of ring A.

In some other preferred embodiments, in a compound of Formula (I), A is

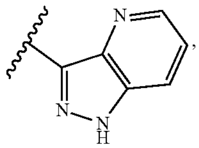

, wherein A is optionally substituted with one or two, preferably one, $R^2$ and in addition A is optionally substituted with one $R^3$.

In some other preferred embodiments, in a compound of Formula (I), A is

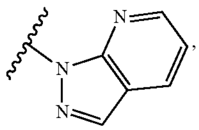

, wherein A is optionally substituted with one or two, preferably one, $R^2$ and in addition A is optionally substituted with one $R^3$.

In some embodiments, in a compound of Formula (I), each $R^2$ is independently selected from halo, $C_{1-4}$ alkyl, $C_{1-4}$ haloalkyl, $C_{3-7}$ cycloalkyl and —($C_{1-4}$ alkylene)-$OR^4$.

Preferably, in a compound of Formula (I), each $R^2$ is independently selected from $C_{1-4}$ alkyl, $C_{1-4}$ haloalkyl and —($C_{1-4}$ alkylene)-$OR^4$. In some embodiments, each $R^2$ is independently selected from $C_{1-4}$ alkyl and —($C_{2-4}$ alkylene)-$OR^4$. In some embodiments, one $R^2$ is selected from methyl, ethyl, propyl and butyl (e.g., n-butyl). In some embodiments, one $R^2$ is —$CH_2CH_2$—$OCH_3$.

In some embodiments, in a compound of Formula (I), $R^3$ is selected from -$L^1$-$R^5$, -$L^2$-$OR^6$, -$L^3$-$NR^7R^8$, —$CONR^9R^{10}$, —$NR^{11}COR^{12}$ and -Y-$L^7$-$NR^7R^8$, wherein preferably Y is selected from —O— and —$NR^{13}$—.

In some preferred embodiments, in a compound of Formula (I), $R^3$ is -$L^1$-$R^5$, wherein preferably $R^5$ is selected from heterocyclyl and heteroaryl, wherein the heterocyclyl and the heteroaryl are each optionally substituted with one or more $R^{16}$.

In some preferred embodiments, in a compound of Formula (I), $R^3$ is —$CONR^9R^{10}$ or —$NR^{11}COR^{12}$.

In some preferred embodiments, in a compound of Formula (I), $R^3$ is -Y-$L^7$-$NR^7R^8$, wherein Y is selected from —O— and —$NR^{13}$—.

In some preferred embodiments, in a compound of Formula (I), $R^3$ is —$OR^6$, wherein $R^6$ is -$L^1$-$R^5$, wherein $L^1$ in said -$L^1$-$R^5$ is preferably $C_{1-6}$ alkylene, more preferably $C_{1-4}$ alkylene, and $R^5$ in said -$L^1$-$R^5$ is preferably selected from heterocyclyl and heteroaryl, wherein the heterocyclyl and the heteroaryl are each optionally substituted with one or more $R^{19}$, or $R^3$ is —$NR^7R^8$, wherein one of $R^7$ or $R^8$ is -$L^1$-$R^1$, wherein $L^1$ in said -$L^1$-$R^5$ is preferably $C_{1-6}$ alkylene, more preferably $C_{1-4}$ alkylene, and $R^5$ in said -$L^1$-$R^5$ is preferably selected from heterocyclyl and heteroaryl, wherein the heterocyclyl and the heteroaryl are each optionally substituted with one or more $R^{16}$.

In some preferred embodiments, in a compound of Formula (I), $R^3$ is -$L^2$-$OR^6$ or -$L^3$-$NR^7R^8$, wherein $L^2$ and $L^3$ are each independently selected from $C_{1-6}$ alkylene, preferably $C_{1-4}$ alkylene.

In some embodiments, in a compound of Formula (I), $R^{11}$, $R^{13}$, $R^{14}$ and $R^{15}$ are each independently selected from hydrogen, $C_{1-6}$ alkyl and $C_{1-6}$ haloalkyl.

In some embodiments, in a compound of Formula (I), each $R^{16}$ is independently selected from $C_{1-6}$ alkyl, $C_{1-6}$ haloalkyl, halo, $C_{1-6}$ alkoxy, $C_{1-6}$ haloalkoxy, —OH, —$NR^{17}R^{18}$, —$COR^{19}$, —CN and $C_{3-7}$ cycloalkyl.

A preferred embodiment relates to a compound of Formula (I), or a salt thereof, wherein:

A is a cyclic group selected from:

i) a 5- or 6-membered monocyclic or 9- or 10-membered bicyclic heteroaryl ring that is fully aromatic, and ii) a 9- or 10-membered bicyclic heteroaryl ring consisting of a 5- or 6-membered monocyclic heteroaryl ring fused to a saturated or partially unsaturated carbocyclic or heterocyclic ring, wherein the 9- or 10-membered bicyclic heterocyclic ring is linked to the rest of the molecule through the 5- or 6-membered monocyclic heteroaryl ring, and preferably A is a 5- or 6-membered monocyclic or 9- or 10-membered bicyclic heteroaryl ring that is fully aromatic, wherein A contains one ring N atom at a position adjacent to the ring atom through which ring A is attached to the rest of the molecule, wherein A optionally contains from 1 to 3, preferably 1 or 2, additional ring N atoms (and wherein all remaining ring atoms of A are carbon atoms), and wherein A is optionally substituted with one or two $R^2$ and in addition A is optionally substituted with one $R^3$;

$R^3$, if present, is selected from -$L^1$-$R^5$, -$L^2$-$OR^6$, -$L^3$-$NR^7R^8$, —$CONR^9R^{10}$, —$NR^{11}COR^{12}$ and -Y-$L^7$-$NR^7R^8$, wherein preferably Y is selected from —O— and —$NR^{13}$—; and wherein preferably m is 0.

A more preferred embodiment relates to a compound of Formula (I), or a salt thereof, wherein:

A is selected from the cyclic groups listed below:

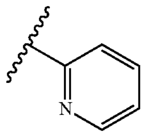
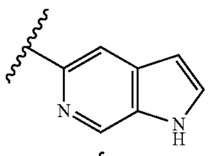
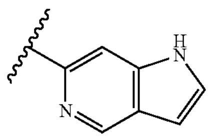
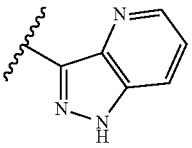
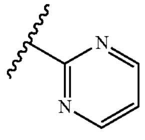
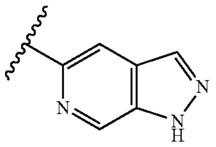
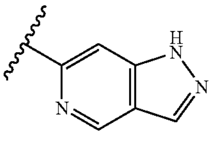
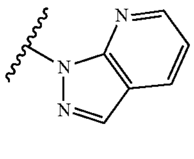

, and preferably A is selected from the cyclic groups listed below:

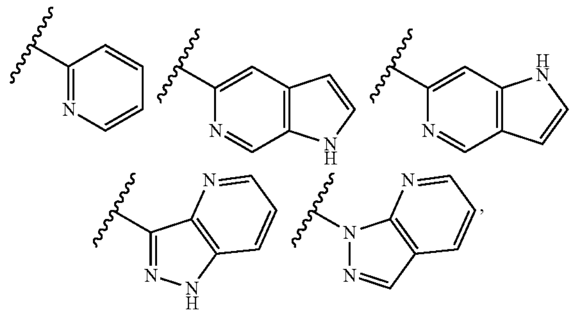

wherein A is optionally substituted with one or two, preferably one, $R^2$ and in addition A is optionally substituted with one $R^3$;

$R^3$, if present, is selected from $-L^1-R^5$, $-L^2-OR^6$, $-L^3-NR^7R^8$, $—CONR^9R^{10}$, $—NR^{11}COR^{12}$ and $-Y-L^7-NR^7R^8$, wherein preferably Y is selected from —O— and $—NR^{13}—$; and wherein preferably m is 0.

In a particularly preferred embodiment, the invention provides a compound of Formula (I), or a salt thereof, having formula (IIa) or (Ib):

(IIa)

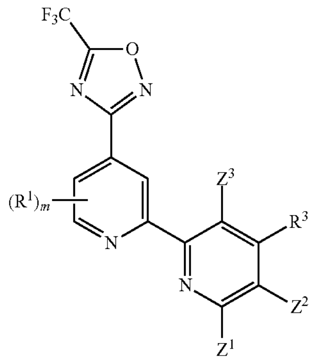

(IIb)

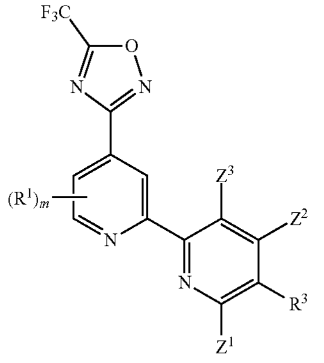

wherein one of $Z^1$, $Z^2$ and $Z^3$ is H and the others are independently selected from H and $R^2$, and preferably all of $Z^1$, $Z^2$ and $Z^3$ are H; and wherein preferably $R^3$ is selected from $-L^1-R^5$, $-L^2-OR^6$, $-L^3-NR^7R^8$, $—CONR^9R^{10}$, $—NR^{11}COR^{12}$ and $-Y-L^7-NR^7R^8$, and more preferably $R^3$ is selected from $—OR^6$, $—NR^7R^8$, $—NR^1COR^{12}$ and $-Y-L^7-NR^7R^8$, wherein preferably Y is selected from —O— and $—NR^{13}—$; and wherein preferably m is 0. In certain preferred embodiments, in a compound of Formula (IIa) or (IIb) $R^3$ is $—NR^1COR^{12}$. In certain other preferred embodiments, in a compound of Formula (IIa) or (IIb) $R^3$ is $-Y-L^7-NR^7R^8$ and Y is selected from —O— and $—NR^{13}—$. In certain other preferred embodiments, in a compound of Formula (IIa) or (IIb) $R^3$ is $—OR^6$, wherein $R^6$ is $-L^1-R^5$, wherein $L^1$ in said $-L^1-R^5$ is preferably $C_{1-4}$ alkylene and $R^5$ in said $-L^1-R^5$ is preferably selected from heterocyclyl and heteroaryl, wherein the heterocyclyl and the heteroaryl are each optionally substituted with one or more $R^{16}$, or $R^3$ is $—NR^7R^8$, wherein one of $R^7$ or $R^8$ is $-L^1-R^5$, wherein $L^1$ in said $-L^1-R^5$ is preferably $C_{1-4}$ alkylene and $R^5$ in said $-L^1-R^5$ is preferably selected from heterocyclyl and heteroaryl, wherein the heterocyclyl and the heteroaryl are each optionally substituted with one or more $R^{16}$.

In another particularly preferred embodiment, the invention relates to a compound of Formula (I), or a salt thereof, having formula (IIIa) or (IIIb):

(IIIa)

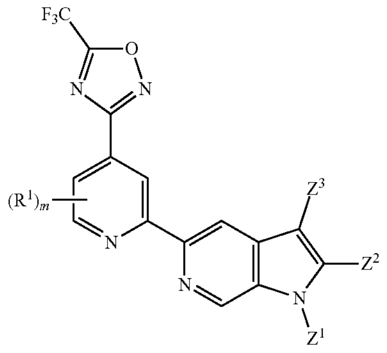

(IIIb)

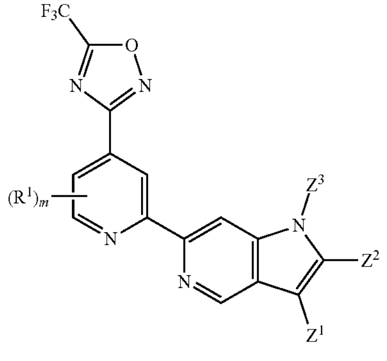

wherein one of $Z^1$, $Z^2$ and $Z^3$ is $R^3$ or H, preferably $R^3$, and the others are independently selected from H and $R^2$;

wherein preferably $R^3$, if present, is selected from $-L^1-R^5$, $-L^2-OR^6$, $-L^3-NR^7R^8$, $—CONR^9R^{10}$, $—NR^{11}COR^{12}$ and $-Y-L^7-NR^7R^8$, wherein preferably Y is selected from —O— and $—NR^{13}—$, and more preferably $R^3$ is selected from $-L^1-R^5$, $-L^2-OR^6$, $-L^3-NR^7R^8$ and $—CONR^9R^{10}$, wherein preferably $L^2$ and $L^3$ are each independently selected from $C_{1-4}$ alkylene; and wherein preferably m is 0. In certain preferred embodiments, the compound of Formula (I) is a compound of formula (IIIa). In certain preferred embodiments, the compound of Formula (I) is a compound of formula (IIIb). In certain preferred embodiments, in a compound of Formula (IIIa) or (IIIb) one of $Z^1$, $Z^2$ and $Z^3$, preferably $Z^2$, is $R^3$ and the others are independently selected from H and $R^2$, and $R^3$ is —$CONR^9R^{10}$. In certain other preferred embodiments, in a compound of Formula (IIIa) or (IIIb) one of $Z^1$, $Z^2$ and $Z^3$ is $R^3$ and the others are independently selected from H and $R^2$, and $R^3$ is $-L^1-R^5$, wherein preferably $R^5$ in said $-L^1-R^5$ is selected from heterocyclyl and heteroaryl, wherein the heterocyclyl and the heteroaryl are each optionally substituted with one or more $R^{16}$. In certain other preferred embodiments, in a compound of Formula (IIIa) or (IIIb) one of $Z^1$, $Z^2$ and $Z^3$ is $R^3$ and the others are independently selected from H and $R^2$, and $R^3$ is $-L^2-OR^6$ or $-L^3-NR^7R^8$ wherein $L^2$ and $L^3$ are each independently selected from $C_{1-4}$ alkylene.

In another particularly preferred embodiment, the invention relates to a compound of Formula (I), or a salt thereof, having formula (IVa):

(IVa)

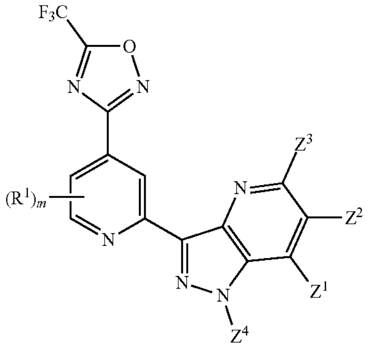

wherein one of $Z^1$, $Z^2$, $Z^3$ and $Z^4$ is selected from $R^2$, $R^3$ and H, and the others are independently selected from H and $R^2$, with the proviso that only up to two of $Z^1$, $Z^2$, $Z^3$ and $Z^4$ are $R^2$; and wherein preferably m is 0. In certain preferred embodiments, in a compound of Formula (IVa) $Z^4$ is selected from $R^2$, $R^3$ and H, and $Z^1$, $Z^2$ and $Z^3$ are independently selected from H and $R^2$ with the proviso that only up to two of $Z^1$, $Z^2$, $Z^3$ and $Z^4$ are $R^2$, and wherein preferably $Z^3$ is H. In certain preferred embodiments, in a compound of Formula (IVa) $Z^4$ is selected from $R^2$, $R^3$ and H, and $Z^1$, $Z^2$ and $Z^3$ are H.

In another particularly preferred embodiment, the invention relates to a compound of Formula (I), or a salt thereof, having formula (IVa-1):

(IVa-1)

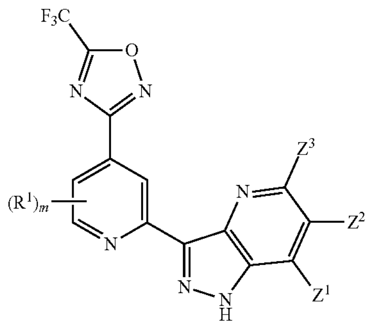

wherein one of $Z^1$, $Z^2$ and $Z^3$ is $R^3$ or H, and the others are independently selected from H and $R^2$, and preferably all of $Z^1$, $Z^2$ and $Z^3$ are H; and wherein preferably m is 0.

In another particularly preferred embodiment, the invention relates to a compound of Formula (I), or a salt thereof, having formula (IVb):

(IVb)

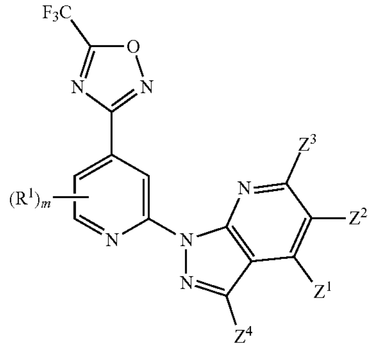

wherein one of $Z^1$, $Z^2$, and Z is selected from $R^2$, $R^3$ and H, and the others are independently selected from H and $R^2$, with the proviso that only up to two of $Z^1$, $Z^2$, $Z^3$ and $Z^4$ are $R^2$; and wherein preferably m is 0.

In another particularly preferred embodiment, the invention relates to a compound of Formula (I), or a salt thereof, having formula (IVb-1):

(IVb-1)

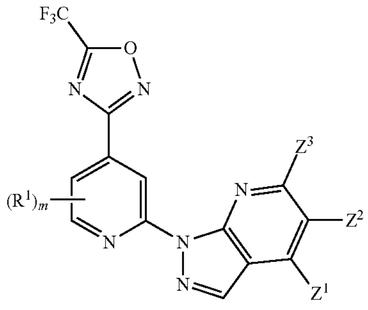

wherein one of $Z^1$, $Z^2$ and $Z^3$ is $R^3$ or H, and the others are independently selected from H and $R^2$, and wherein preferably m is 0.

In certain embodiments, the invention provides a compound of Formula (I), or a salt thereof, selected from:

3-(2-(1-Butyl-1H-pyrrolo[2,3-c]pyridin-5-yl)pyridin-4-yl)-5-(trifluoromethyl)-1,2,4-oxadiazole, 3-(2-(1-Propyl-1H-pyrrolo[2,3-c]pyridin-5-yl)pyridin-4-yl)-5-(trifluoromethyl)-1,2,4-oxadiazole, 1-Butyl-N,N-dimethyl-5-(4-(5-(trifluoromethyl)-1,2,4-oxadiazol-3-yl)pyridin-2-yl)-1H-pyrrolo[2,3-c]pyridine-2-carboxamide, N,N-Diethyl-3-((4'-(5-(trifluoromethyl)-1,2,4-oxadiazol-3-yl)-[2,2'-bipyridin]-5-yl)oxy)propan-1-amine, 1-Butyl-N-ethyl-5-(4-(5-(trifluoromethyl)-1,2,4-oxadiazol-3-yl)pyridin-2-yl)-1H-pyrrolo[2,3-c]pyridine-2-carboxamide, 4-(3-((4'-(5-(Trifluoromethyl)-1,2,4-oxadiazol-3-yl)-[2,2'-bipyridin]-5-yl)oxy)propyl)morpholine, 3-(5'-(3-(4,4-Difluoropiperidin-1-yl)propoxy)-[2,2'-bipyridin]-4-yl)-5-(trifluoromethyl)-1,2,4-oxadiazole, 3-(2-(3-(Piperidin-1-ylmethyl)-1-propyl-1H-pyrrolo[2,3-c]pyridin-5-yl)pyridin-4-yl)-5-(trifluoromethyl)-1,2,4-oxadiazole, 4-((1-Propyl-5-(4-(5-(trifluoromethyl)-1,2,4-oxadiazol-3-yl)pyridin-2-yl)-1H-pyrrolo[2,3-c]pyridin-3-yl)methyl)morpholine, N-Butyl-3-methoxy-N-(4'-(5-(trifluoromethyl)-1,2,4-oxadiazol-3-yl)-[2,2'-bipyridin]-5-yl)propanamide, N-(Cyclopropylmethyl)-N-methyl-4'-(5-(trifluoromethyl)-1,2,4-oxadiazol-3-yl)-[2,2'-bipyridin]-5-amine, N1,N1-Diethyl-N3-(4'-(5-(trifluoromethyl)-1,2,4-oxadiazol-3-yl)-[2,2'-bipyridin]-5-yl)propane-1,3-diamine, N-(3-(4,4-Difluoropiperidin-1-yl)propyl)-N-methyl-4'-(5-(trifluoromethyl)-1,2,4-oxadiazol-3-yl)-[2,2'-bipyridin]-5-amine, N,N-Diethyl-3-(2-(4-(5-(trifluoromethyl)-1,2,4-oxadiazol-3-yl)pyridin-2-yl)pyrimidin-5-yloxy)propan-1-amine, N1,N1-Diethyl-N3-methyl-N3-(4'-(5-(trifluoromethyl)-1,2,4-oxadiazol-3-yl)-2,2'-bipyridin-5-yl)propane-1,3-diamine, 3-(2-(1-(Tetrahydro-2H-pyran-4-yl)-1H-pyrrolo[3,2-c]pyridin-6-yl)pyridin-4-yl)-5-(trifluoromethyl)-1,2,4-oxadiazole, N-Ethyl-N-phenethyl-3-((4'-(5-(trifluoromethyl)-1,2,4-oxadiazol-3-yl)-[2,2'-bipyridin]-5-yl)oxy)propan-1-amine, 2-Phenyl-N-(4'-(5-(trifluoromethyl)-1,2,4-oxadiazol-3-yl)-[2,2'-bipyridin]-5-yl)acetamide, 3-(2-(1-((Tetrahydro-2H-pyran-4-yl)methyl)-1H-pyrrolo[3,2-c]pyridin-6-yl)pyridin-4-yl)-5-(trifluoromethyl)-1,2,4-oxadiazole, 3-(4'-(2-(4,4-Difluoropiperidin-1-yl)ethoxy)-[2,2'-bipyridin]-4-yl)-5-(trifluoromethyl)-1,2,4-oxadiazole, 4-(2-((4'-(5-(Trifluoromethyl)-1,2,4-oxadiazol-3-yl)-[2,2'-bipyridin]-4-yl)oxy)ethyl)morpholine, N,N,1-Trimethyl-5-(4-(5-(trifluoromethyl)-1,2,4-oxadiazol-3-yl)pyridin-2-yl)-1H-pyrrolo[2,3-c]pyridine-2-carboxamide, 3-(2-(1-Propyl-3-(1H-pyrazol-4-yl)-1H-pyrrolo[2,3-c]pyridin-5-yl)pyridin-4-yl)-5-(trifluoromethyl)-1,2,4-oxadiazole, 1-Butyl-N,N-diethyl-5-(4-(5-(trifluoromethyl)-1,2,4-oxadiazol-3-yl)pyridin-2-yl)-1H-pyrrolo[2,3-c]pyridine-2-carboxamide, 3-(2-(1-(2-Methoxyethyl)-1H-pyrrolo[2,3-c]pyridin-5-yl)pyridin-4-yl)-5-(trifluoromethyl)-1,2,4-oxadiazole, 2-(4,4-Difluoropiperidin-1-yl)-N-(4'-(5-(trifluoromethyl)-1,2,4-oxadiazol-3-yl)-[2,2'-bipyridin]-4-yl)acetamide, N-(2-(4,4-Difluoropiperidin-1-yl)ethyl)-4'-(5-(trifluoromethyl)-1,2,4-oxadiazol-3-yl)-[2,2'-bipyridin]-4-amine, 3-(2-(3-(Piperidin-1-ylmethyl)-1H-pyrazolo[3,4-c]pyridin-5-yl)pyridin-4-yl)-5-(trifluoromethyl)-1,2,4-oxadiazole, 3-(2-(1-(2-(4,4-Difluoropiperidin-1-yl)ethyl)-1H-pyrrolo[3,2-c]pyridin-6-yl)pyridin-4-yl)-5-(trifluoromethyl)-1,2,4-oxadiazole, 1-Methyl-N-(4'-(5-(trifluoromethyl)-1,2,4-oxadiazol-3-yl)-[2,2'-bipyridin]-5-yl)piperidine-4-carboxamide, 3-Phenyl-N-(4'-(5-(trifluoromethyl)-1,2,4-oxadiazol-3-yl)-[2,2'-bipyridin]-4-yl)propanamide, 2-Cyclobutyl-N-(4'-(5-(trifluoromethyl)-1,2,4-oxadiazol-3-yl)-[2,2'-bipyridin]-4-yl)acetamide, N-(Piperidin-3-yl)-4'-(5-(trifluoromethyl)-1,2,4-oxadiazol-3-yl)-[2,2'-bipyridine]-4-carboxamide, 3-(5'-(3-(1H-Pyrazol-1-yl)propoxy)-[2,2'-bipyridin]-4-yl)-5-(trifluoromethyl)-1,2,4-oxadiazole, (1-Propyl-5-(4-(5-(trifluoromethyl)-1,2,4-oxadiazol-3-yl)pyridin-2-yl)-1H-pyrrolo[2,3-c]pyridin-3-yl)methanol, 3-(2-(3-(Methoxymethyl)-1-propyl-1H-pyrrolo[2,3-c]pyridin-5-yl)pyridin-4-yl)-5-(trifluoromethyl)-1,2,4-oxadiazole, 4-((1-Propyl-5-(4-(5-(trifluoromethyl)-1,2,4-oxadiazol-3-yl)pyridin-2-yl)-1H-pyrrolo[2,3-c]pyridin-3-yl)methyl)morpholine, 3-(2-(1H-Pyrrolo[3,2-c]pyridin-6-yl)pyridin-4-yl)-5-(trifluoromethyl)-1,2,4-oxadiazole, 3-(2-(1-(Pyridin-4-ylmethyl)-1H-pyrrolo[3,2-c]pyridin-6-yl)pyridin-4-yl)-5-(trifluoromethyl)-1,2,4-oxadiazole, N-((1-Methylpiperidin-4-yl)methyl)-4'-(5-(trifluoromethyl)-1,2,4-oxadiazol-3-yl)-[2,2'-bipyridine]-4-carboxamide, N-((1-Methylpiperidin-4-yl)methyl)-4'-(5-(trifluoromethyl)-1,2,4-oxadiazol-3-yl)-[2,2'-bipyridine]-5-carboxamide, 3-(2-(1-(1-(2,2,2-Trifluoroethyl)piperidin-4-yl)-1H-pyrrolo[3,2-c]pyridin-6-yl)pyridin-4-yl)-5-(trifluoromethyl)-1,2,4-oxadiazole, 3-(2-(1-Methyl-3-(1H-pyrazol-4-yl)-1H-pyrrolo[2,3-c]pyridin-5-yl)pyridin-4-yl)-5-(trifluoromethyl)-1,2,4-oxadiazole, 3-(2-(1-Butyl-3-(1-methyl-1,2,3,6-tetrahydropyridin-4-yl)-1H-pyrrolo[2,3-c]pyridin-5-yl)pyridin-4-yl)-5-(trifluoromethyl)-1,2,4-oxadiazole, N-Methyl-3-(4'-(5-(trifluoromethyl)-1,2,4-oxadiazol-3-yl)-2,2'-bipyridin-5-yloxy)propan-1-amine, 1-(1-Butyl-5-(4-(5-(trifluoromethyl)-1,2,4-oxadiazol-3-yl)pyridin-2-yl)-1H-pyrrolo[2,3-c]pyridin-3-yl)-N,N-dimethylmethanamine, 3-(2-(1H-Pyrazolo[4,3-b]pyridin-3-yl)pyridin-4-yl)-5-(trifluoromethyl)-1,2,4-oxadiazole, N-(4'-(5-(trifluoromethyl)-1,2,4-oxadiazol-3-yl)-[2,2'-bipyridin]-4-yl)piperidine-3-carboxamide, 1-(2-Methoxyethyl)-N,N-dimethyl-5-(4-(5-(trifluoromethyl)-1,2,4-oxadiazol-3-yl)pyridin-2-yl)-1H-pyrrolo[2,3-c]pyridine-2-carboxamide, 3-(2-(1-(2-Methoxyethyl)-3-(1H-pyrazol-4-yl)-1H-pyrrolo[2,3-c]pyridin-5-yl)pyridin-4-yl)-5-(trifluoromethyl)-1,2,4-oxadiazole, 3-(2-(1-Methyl-1H-pyrrolo[2,3-c]pyridin-5-yl)pyridin-4-yl)-5-(trifluoromethyl)-1,2,4-oxadiazole, 3-(2-(1-(2-Methoxyethyl)-1H-pyrrolo[3,2-c]pyridin-6-yl)pyridin-4-yl)-5-(trifluoromethyl)-1,2,4-oxadiazole, 3-(2-(1-(Pyridin-3-ylmethyl)-1H-pyrrolo[3,2-c]pyridin-6-yl)pyridin-4-yl)-5-(trifluoromethyl)-1,2,4-oxadiazole, 3-(2-(1-(Pyridin-2-ylmethyl)-1H-pyrrolo[3,2-c]pyridin-6-yl)pyridin-4-yl)-5-(trifluoromethyl)-1,2,4-oxadiazole, 2-(Methyl(3-((4'-(5-(trifluoromethyl)-1,2,4-oxadiazol-3-yl)-[2,2'-bipyridin]-5-yl)oxy)propyl)amino)ethan-1-ol, 3-(2-(1-(2-Methoxyethyl)-1H-pyrazolo[3,4-c]pyridin-5-yl)pyridin-4-yl)-5-(trifluoromethyl)-1,2,4-oxadiazole, 3-(2-(2-(2-Methoxyethyl)-2H-pyrazolo[3,4-c]pyridin-5-yl)pyridin-4-yl)-5-(trifluoromethyl)-1,2,4-oxadiazole, 3-(2-(1H-Pyrazolo[3,4-b]pyridin-1-yl)pyridin-4-yl)-5-(trifluoromethyl)-1,2,4-oxadiazole, N,N-Dimethyl-3-((4'-(5-(trifluoromethyl)-1,2,4-oxadiazol-3-yl)-[2,2'-bipyridin]-5-yl)oxy)propan-1-amine, 3-(2-(1-Methyl-1H-pyrazolo[4,3-b]pyridin-3-yl)pyridin-4-yl)-5-(trifluoromethyl)-1,2,4-oxadiazole, 3-(2-(1-(2-Methoxyethyl)-1H-pyrazolo[4,3-b]pyridin-3-yl)pyridin-4-yl)-5-(trifluoromethyl)-1,2,4-oxadiazole, 3-(2-(1-Ethyl-1H-pyrazolo[4,3-b]pyridin-3-yl)pyridin-4-yl)-5-(trifluoromethyl)-1,2,4-oxadiazole, 3-(2-(1-(2-(1-Methyl-1H-imidazol-2-yl)ethyl)-1H-pyrazolo[4,3-b]pyridin-3-yl)pyridin-4-yl)-5-(trifluoromethyl)-1,2,4-oxadiazole, and 3-(2-(1-((1-Methyl-1H-pyrazol-4-yl)methyl)-1H-pyrrolo[3,2-c]pyridin-6-yl)pyridin-4-yl)-5-(trifluoromethyl)-1,2,4-oxadiazole, or a salt thereof.

Further examples of compounds of Formula (I) according to the invention include the compounds shown below and salts thereof:

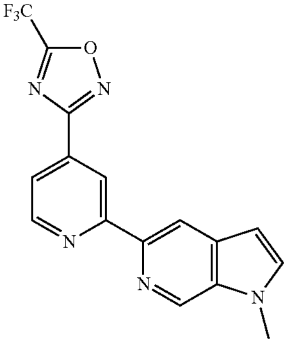

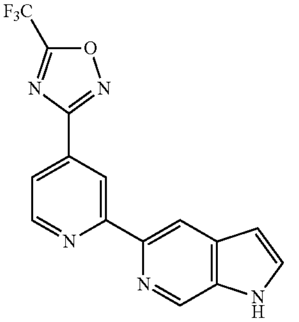

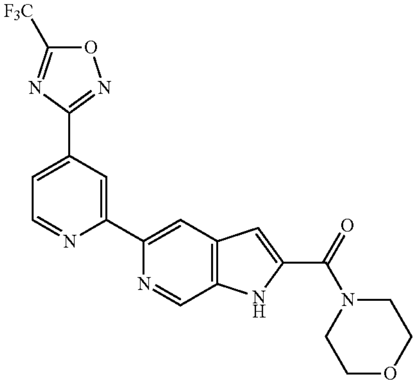

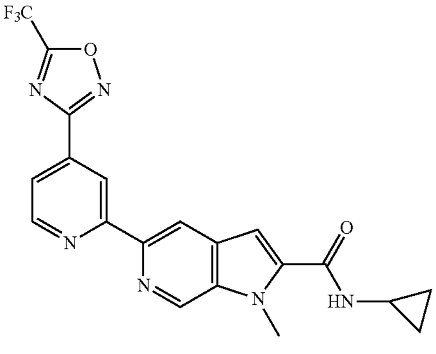

-continued

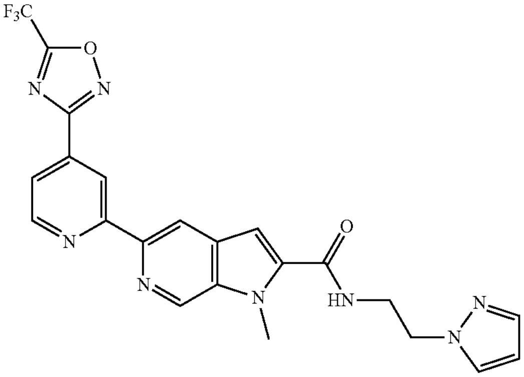

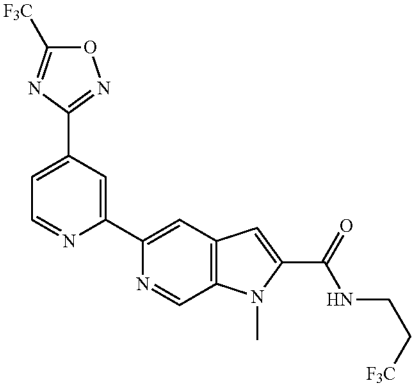

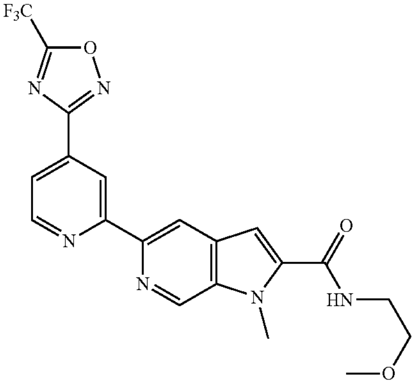

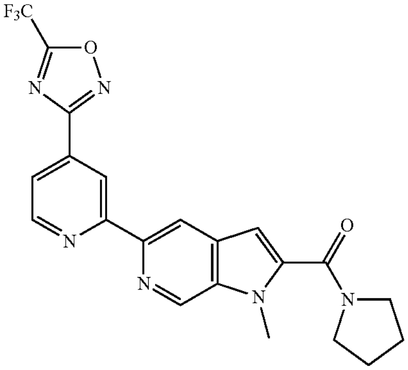

-continued
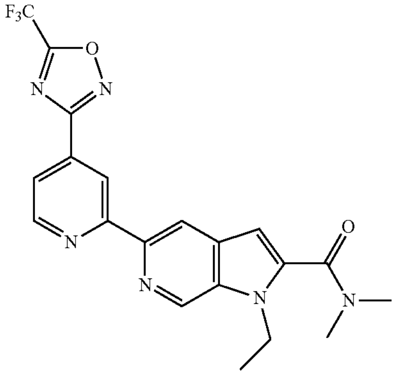
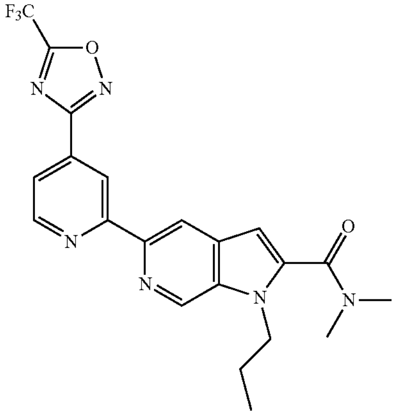
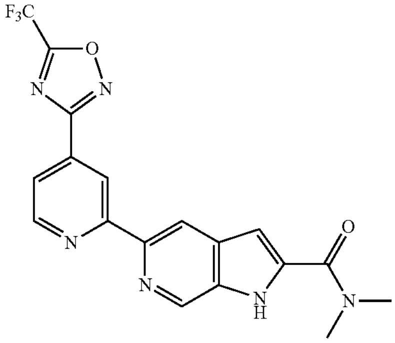
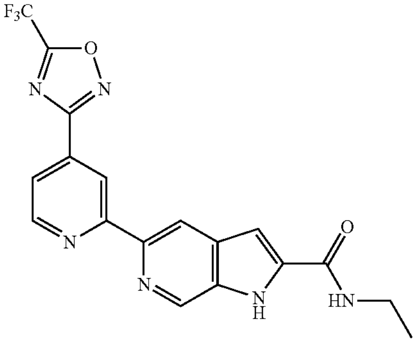
-continued
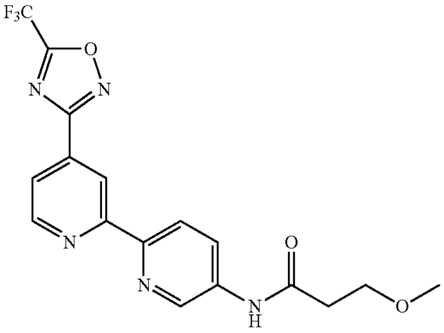
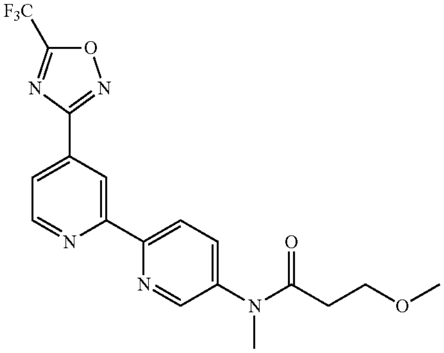
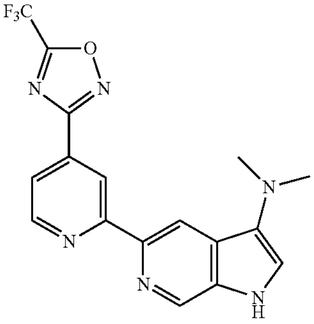
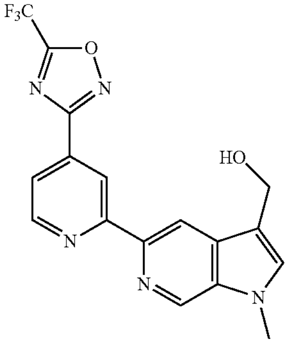
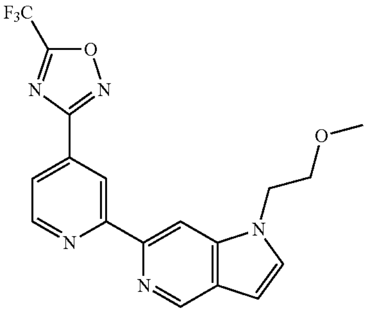

-continued
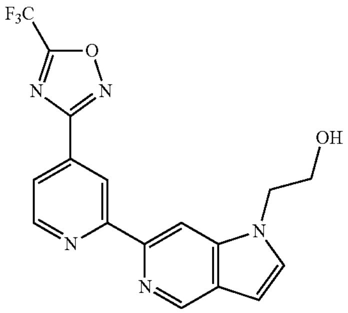
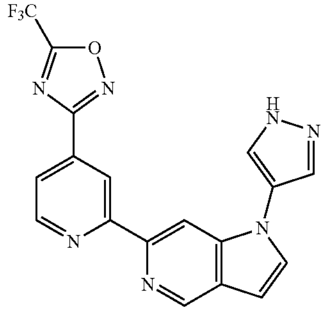
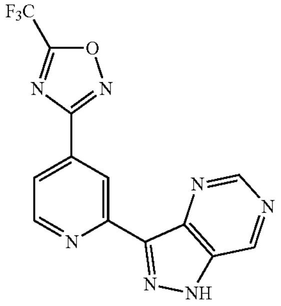
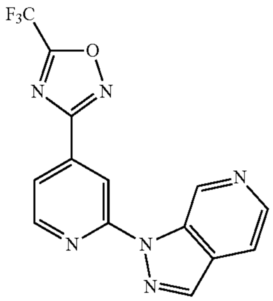
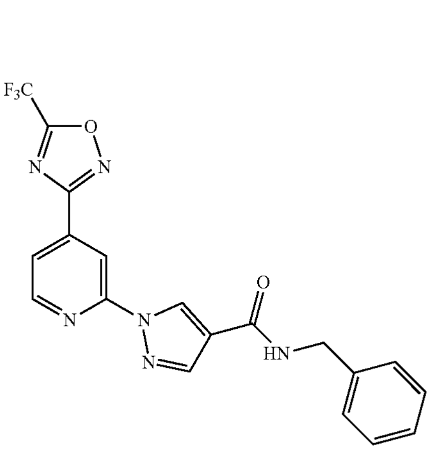
-continued
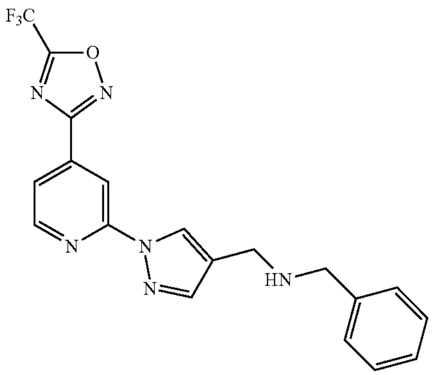
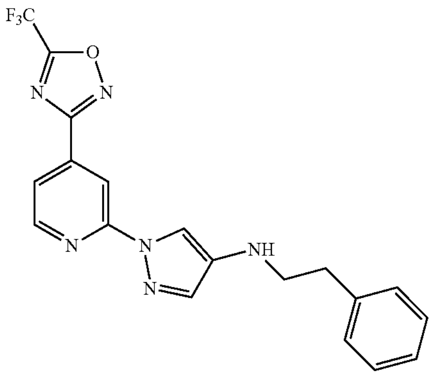
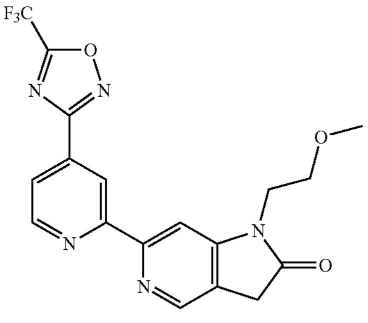
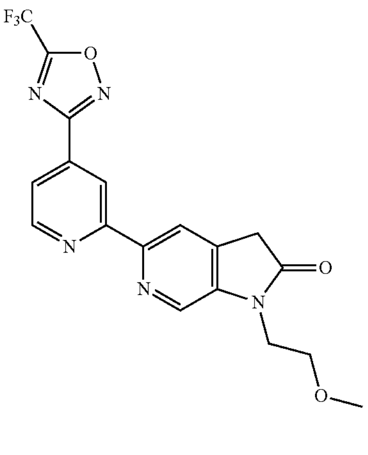

-continued
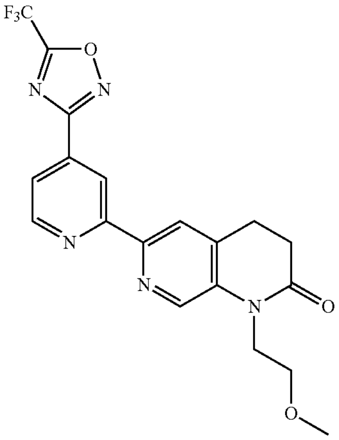
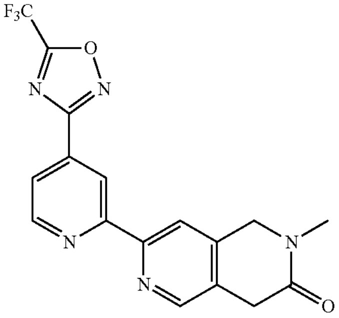
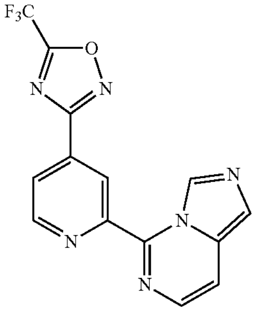
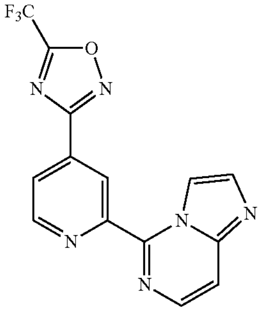
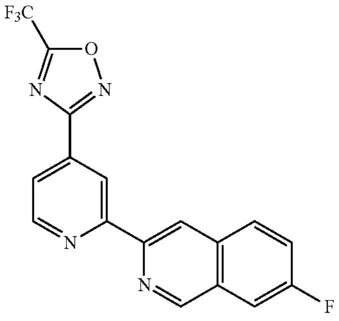
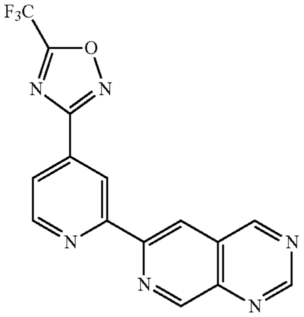
-continued
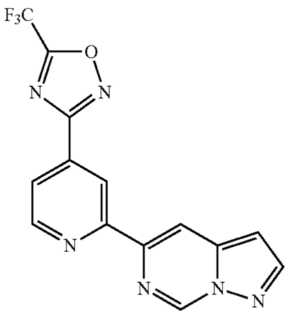
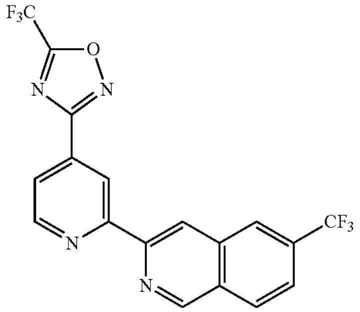
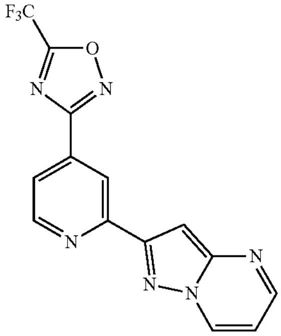
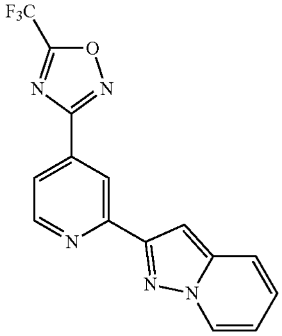
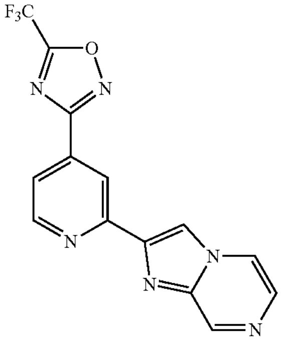
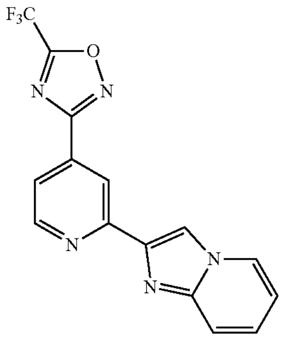
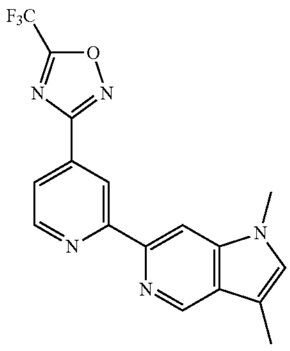

In a particularly preferred embodiment, the invention provides a compound of Formula (I), or a salt thereof, selected from N,N-Diethyl-3-((4'-(5-(trifluoromethyl)-1,2,4-oxadiazol-3-yl)-[2,2'-bipyridin]-5-yl)oxy)propan-1-amine, 1-Butyl-N,N-dimethyl-5-(4-(5-(trifluoromethyl)-1,2,4-oxadiazol-3-yl)pyridin-2-yl)-1H-pyrrolo[2,3-c]pyridine-2-carboxamide, N,N,1-Trimethyl-5-(4-(5-(trifluoromethyl)-1,2,4-oxadiazol-3-yl)pyridin-2-yl)-1H-pyrrolo[2,3-c]pyridine-2-carboxamide, 3-(2-(1-Propyl-3-(1H-pyrazol-4-yl)-1H-pyrrolo[2,3-c]pyridin-5-yl)pyridin-4-yl)-5-(trifluoromethyl)-1,2,4-oxadiazole, 2-(4,4-Difluoropiperidin-1-yl)-N-(4'-(5-(trifluoromethyl)-1,2,4-oxadiazol-3-yl)-[2,2'-bipyridin]-4-yl)acetamide, 3-(2-(1-(2-Methoxyethyl)-1H-pyrazolo[4,3-b]pyridin-3-yl)pyridin-4-yl)-5-(trifluoromethyl)-1,2,4-oxadiazole, 3-(2-(1-Ethyl-1H-pyrazolo[4,3-b]pyridin-3-yl)pyridin-4-yl)-5-(trifluoromethyl)-1,2,4-oxadiazole, 3-(2-(1-(2-(1-Methyl-1H-imidazol-2-yl)ethyl)-1H-pyrazolo[4,3-b]pyridin-3-yl)pyridin-4-yl)-5-(trifluoromethyl)-1,2,4-oxadiazole, 3-(2-(1H-Pyrazolo[4,3-b]pyridin-3-yl)pyridin-4-yl)-5-(trifluoromethyl)-1,2,4-oxadiazole, and 3-(2-(1-Methyl-1H-pyrazolo[4,3-b]pyridin-3-yl)pyridin-4-yl)-5-(trifluoromethyl)-1,2,4-oxadiazole, or a salt thereof.

The invention also relates to any individual compound or any subgroup of the compounds recited in the lists above, and their salts.

Moreover, the present invention also relates to a compound of Formula (I), or a salt thereof, as described and defined herein (including any of the preferred definitions/embodiments described herein above), wherein it is preferred that the following compounds are excluded from Formula (I):

3-(2-(thiazol-4-yl)pyridin-4-yl)-5-(trifluoromethyl)-1,2,4-oxadiazole, 3-(2-(2-methylthiazol-4-yl)pyridin-4-yl)-5-(trifluoromethyl)-1,2,4-oxadiazole, N,N-dimethyl-4-(4-(5-(trifluoromethyl)-1,2,4-oxadiazol-3-yl)pyridin-2-yl)thiazole-2-carboxamide, 3-(2-(oxazol-4-yl)pyridin-4-yl)-5-(trifluoromethyl)-1,2,4-oxadiazole, 3-(2-(2-methyloxazol-4-yl)pyridin-4-yl)-5-(trifluoromethyl)-1,2,4-oxadiazole, N,N-dimethyl-4-(4-(5-(trifluoromethyl)-1,2,4-oxadiazol-3-yl)pyridin-2-yl)oxazole-2-carboxamide, 3-(2-(1H-imidazol-4-yl)pyridin-4-yl)-5-(trifluoromethyl)-1,2,4-oxadiazole, 3-(2-(1,2-dimethyl-1H-imidazol-4-yl)pyridin-4-yl)-5-(trifluoromethyl)-1,2,4-oxadiazole, N,N,1-trimethyl-4-(4-(5-(trifluoromethyl)-1,2,4-oxadiazol-3-yl)pyridin-2-yl)-1H-imidazole-2-carboxamide, 3-(2-(1H-pyrrol-2-yl)pyridin-4-yl)-5-(trifluoromethyl)-1,2,4-oxadiazole, 3-(2-(5-methyl-1H-pyrrol-2-yl)pyridin-4-yl)-5-(trifluoromethyl)-1,2,4-oxadiazole, N,N-dimethyl-5-(4-(5-(trifluoromethyl)-1,2,4-oxadiazol-3-yl)pyridin-2-yl)-1H-pyrrole-2-carboxamide, 3-(2-(1,2,4-thiadiazol-5-yl)pyridin-4-yl)-5-(trifluoromethyl)-1,2,4-oxadiazole, 3-(2-(3-methyl-1,2,4-thiadiazol-5-yl)pyridin-4-yl)-5-(trifluoromethyl)-1,2,4-oxadiazole, N,N-dimethyl-5-(4-(5-(trifluoromethyl)-1,2,4-oxadiazol-3-yl)pyridin-2-yl)-1,2,4-thiadiazole-3-carboxamide, 3-(2-(1,2,4-oxadiazol-5-yl)pyridin-4-yl)-5-(trifluoromethyl)-1,2,4-oxadiazole, 3-methyl-5-(4-(5-(trifluoromethyl)-1,2,4-oxadiazol-3-yl)pyridin-2-yl)-1,2,4-oxadiazole, N,N-dimethyl-5-(4-(5-(trifluoromethyl)-1,2,4-oxadiazol-3-yl)pyridin-2-yl)-1,2,4-oxadiazole-3-carboxamide, 3-(2-(1H-1,2,4-triazol-5-yl)pyridin-4-yl)-5-(trifluoromethyl)-1,2,4-oxadiazole, 3-(2-(3-methyl-1H-1,2,4-triazol-5-yl)pyidin-4-yl)-5-(trifluoromethyl)-1,2,4-oxadiazole, N,N-dimethyl-5-(4-(5-(trifluoromethyl)-1,2,4-oxadiazol-3-yl)pyridin-2-yl)-1H-1,2,4-triazole-3-carboxamide, 3-(2-(1H-pyrazol-5-yl)pyridin-4-yl)-5-(trifluoromethyl)-1,2,4-oxadiazole, 3-(2-(3-methyl-1H-pyrazol-5-yl)pyridin-4-yl)-5-(trifluoromethyl)-1,2,4-oxadiazole, N,N-dimethyl-5-(4-(5-(trifluoromethyl)-1,2,4-oxadiazol-3-yl)pyridin-2-yl)-1H-pyrazole-3-carboxamide, 3-(2-(1H-1,2,3-triazol-4-yl)pyridin-4-yl)-5-(trifluoromethyl)-1,2,4-oxadiazole, 3-(2-(1-methyl-1H-1,2,3-triazol-4-yl)pyridin-4-yl)-5-(trifluoromethyl)-1,2,4-oxadiazole, N,N-dimethyl-4-(4-(5-(trifluoromethyl)-1,2,4-oxadiazol-3-yl)pyridin-2-yl)-1H-1,2,3-triazole-1-carboxamide, 3-(2-(4H-1,2,4-triazol-3-yl)pyridin-4-yl)-5-(trifluoromethyl)-1,2,4-oxadiazole, 3-(2-(5-methyl-4H-1,2,4-triazol-3-yl)pyridin-4-yl)-5-(trifluoromethyl)-1,2,4-oxadiazole, N,N-dimethyl-5-(4-(5-(trifluoromethyl)-1,2,4-oxadiazol-3-yl)pyridin-2-yl)-4H-1,2,4-triazole-3-carboxamide, 3-(2-(1,3,4-oxadiazol-2-yl)pyridin-4-yl)-5-(trifluoromethyl)-1,2,4-oxadiazole, 3-(2-(5-methyl-1,3,4-oxadiazol-2-yl)pyridin-4-yl)-5-(trifluoromethyl)-1,2,4-oxadiazole, N,N-dimethyl-5-(4-(5-(trifluoromethyl)-1,2,4-oxadiazol-3-yl)pyridin-2-yl)-1,3,4-oxadiazole-2-carboxamide, 3-(2-(1,3,4-thiadiazol-2-yl)pyridin-4-yl)-5-(trifluoromethyl)-1,2,4-oxadiazole, 3-(2-(5-methyl-1,3,4-thiadiazol-2-yl)pyridin-4-yl)-5-(trifluoromethyl)-1,2,4-oxadiazole, N,N-dimethyl-5-(4-(5-(trifluoromethyl)-1,2,4-oxadiazol-3-yl)pyridin-2-yl)-1,3,4-thiadiazole-2-carboxamide, 3-(2-(2H-1,2,3-triazol-4-yl)pyridin-4-yl)-5-(trifluoromethyl)-1,2,4-oxadiazole, 3-(2-(2-methyl-2H-1,2,3-triazol-4-yl)pyridin-4-yl)-5-(trifluoromethyl)-1,2,4-oxadiazole, N,N-dimethyl-4-(4-(5-(trifluoromethyl)-1,2,4-oxadiazol-3-yl)pyridin-2-yl)-2H-1,2,3-triazole-2-carboxamide, 3-(2-(2H-tetrazol-5-yl)pyridin-4-yl)-5-(trifluoromethyl)-1,2,4-oxadiazole, 3-(2-(2-methyl-2H-tetrazol-5-yl)pyridin-4-yl)-5-(trifluoromethyl)-1,2,4-oxadiazole, N,N-dimethyl-5-(4-(5-(trifluoromethyl)-1,2,4-oxadiazol-3-yl)pyridin-2-yl)-2H-tetrazole-2-carboxamide, 3-(2-(1,3,5-triazin-2-yl)pyridin-4-yl)-5-(trifluoromethyl)-1,2,4-oxadiazole, 3-(2-(4-methyl-1,3,5-triazin-2-yl)pyridin-4-yl)-5-(trifluoromethyl)-1,2,4-oxadiazole, N,N-dimethyl-4-(4-(5-(trifluoromethyl)-1,2,4-oxadiazol-3-yl)pyridin-2-yl)-1,3,5-triazine-2-carboxamide, 3-(2-(pyridazin-3-yl)pyridin-4-yl)-5-(trifluoromethyl)-1,2,4-oxadiazole, 3-(2-(6-methylpyridazin-3-yl)pyridin-4-yl)-5-(trifluoromethyl)-1,2,4-oxadiazole, N,N-dimethyl-6-(4-(5-(trifluoromethyl)-1,2,4-oxadiazol-3-yl)pyridin-2-yl)pyridazine-3-carboxamide, 3-(2-(pyrimidin-4-yl)pyridin-4-yl)-5-(trifluoromethyl)-1,2,4-oxadiazole,
3-(2-(2-methylpyrimidin-4-yl)pyridin-4-yl)-5-(trifluoromethyl)-1,2,4-oxadiazole,
N,N-dimethyl-4-(4-(5-(trifluoromethyl)-1,2,4-oxadiazol-3-yl)pyridin-2-yl)pyrimidine-2-carboxamide,
3-(2-(pyrazin-2-yl)pyridin-4-yl)-5-(trifluoromethyl)-1,2,4-oxadiazole,
3-(2-(5-methylpyrazin-2-yl)pyridin-4-yl)-5-(trifluoromethyl)-1,2,4-oxadiazole,
N,N-dimethyl-5-(4-(5-(trifluoromethyl)-1,2,4-oxadiazol-3-yl)pyridin-2-yl)pyrazine-2-carboxamide,
3-(2-(indolizin-3-yl)pyridin-4-yl)-5-(trifluoromethyl)-1,2,4-oxadiazole,
3-(2-(1H-indol-2-yl)pyridin-4-yl)-5-(trifluoromethyl)-1,2,4-oxadiazole,
3-(2-(1-methyl-1H-benzo[d]imidazol-2-yl)pyridin-4-yl)-5-(trifluoromethyl)-1,2,4-oxadiazole,
3-(2-(1-methyl-1H-indazol-3-yl)pyridin-4-yl)-5-(trifluoromethyl)-1,2,4-oxadiazole,
3-(2-(benzo[d]isothiazol-3-yl)pyridin-4-yl)-5-(trifluoromethyl)-1,2,4-oxadiazole,
3-(4-(5-(trifluoromethyl)-1,2,4-oxadiazol-3-yl)pyridin-2-yl)benzo[d]isoxazole,
3-(2-(isoquinolin-1-yl)pyridin-4-yl)-5-(trifluoromethyl)-1,2,4-oxadiazole,
3-(2-(1,8-naphthyridin-2-yl)pyridin-4-yl)-5-(trifluoromethyl)-1,2,4-oxadiazole, and
3-(2-(phthalazin-1-yl)pyridin-4-yl)-5-(trifluoromethyl)-1,2,4-oxadiazole.

Accordingly, it is preferred that the compounds mentioned in the preceding sentence as well as salts and tautomers thereof are excluded.

Definitions of specific terms as used in the specification and claims are provided below. All other technical and scientific terms used herein and not defined below shall have the same meaning as commonly understood by one of ordinary skill in the art to which this invention pertains. In the case of conflict, the present specification, including definitions, will control.

In the case of conflict between the chemical structures and names of the compounds disclosed herein, the chemical structures will control.

At various places in the present specification, substituents of compounds of the invention are disclosed in groups or in ranges. It is specifically intended that the invention include each and every individual subcombination of the members of such groups and ranges.

At various places in the present specification various aryl, heteroaryl, carbocyclyl and heterocyclyl groups are described. Unless otherwise specified, these rings can be attached to the rest of the molecule at any ring member as permitted by valency. For example, the term "pyridyl" (or pyridinyl) may refer to a pyridin-2-yl, pyridin-3-yl or pyridin-4-yl ring, and the term "piperidinyl" may refer to a piperidin-1-yl, piperidin-2-yl, piperidin-3-yl or piperidin-4-yl ring.

The term "n-membered" where n is an integer describes the number of ring-forming atoms in a ring system where the number of ring-forming atoms is n. For example, phenyl is an example of a 6-membered aryl, cyclopropyl is an example of a 3-membered carbocyclyl, pyrazolyl is an example of a 5-membered heteroaryl, quinolinyl is an example of a 10-membered heteroaryl, piperidinyl is an example of a 6-membered heterocyclyl, and decahydroquinolinyl is an example of a 10-membered heterocyclyl.

The term "$C_{y-z}$", where y and z are integers, used in combination with a chemical group, designates a range of the number of carbon atoms in the chemical group, with y and z being the endpoints, which are included. Examples include $C_{1-6}$, $C_{2-6}$, $C_{3-7}$ and the like.

The term "$C_{y-z}$ alkyl" refers to a saturated straight or branched acyclic hydrocarbon group having y to z carbon atoms. Thus, a $C_{1-6}$ alkyl is an alkyl having from one to six carbon atoms. Examples of $C_{1-6}$ alkyl include, but are not limited to, methyl, ethyl, n-propyl, isopropyl, n-butyl, isobutyl, sec-butyl, tert-butyl, n-pentyl, isopentyl, sec-pentyl, neopentyl, n-hexyl, or sec-hexyl.

The term "$C_{y-z}$ alkoxy" refers to an $C_{y-z}$, alkyl group (as defined above) covalently linked to an oxygen atom, i.e. a group of formula —O-alkyl where the alkyl group has y to z carbon atoms. The term $C_{1-6}$ alkoxy thus refers to an alkoxy group wherein the alkyl moiety has from 1 to 6 carbon atoms. Examples of $C_{1-6}$ alkoxy include, but are not limited to, methoxy, ethoxy, n-propoxy, isopropoxy, n-butoxy, iso-butoxy, sec-butoxy, tert-butoxy, n-pentoxy or n-hexyloxy.

The term "$C_{y-z}$ alkylene" refers to a saturated straight or branched divalent acyclic hydrocarbon group having from y to z carbon atoms. Thus, for example, a $C_{1-6}$ alkylene is an alkylene having from one to six carbon atoms. Preferably, said alkylene groups are polymethylene groups, i.e. $(CH_2)_x$, where x indicates the number of $CH_2$ units in the respective alkylene group, like from 1 to 6. Examples of a $C_{1-6}$ alkylene include, but are not limited to, methylene, ethylene, propylene, n-butylene, n-pentylene or n-hexylene.

The term "aryl", unless otherwise specified, refers to a 6- to 18-membered hydrocarbon ring system which contains only hydrogen and carbon atoms and which is monocyclic or multicyclic (e.g. fused, bridged or spiro rings), wherein at least one of the rings in the ring system is aromatic. Aryl as used herein thus covers fully aromatic hydrocarbon ring systems, i.e. where all the ring(s) in the system are aromatic, like phenyl, naphthyl or anthracyl, as well as ring systems in which an aromatic hydrocarbon ring (e.g. phenyl) is fused to one or more non-aromatic (i.e. saturated or partially unsaturated) hydrocarbon rings, like indanyl, indenyl, 1-oxo-2,3-dihydro-1H-indenyl, tetrahydronaphthyl, fluorenyl and the like. In some embodiments, the point of attachment is on the aromatic hydrocarbon ring. In some embodiments, the aryl group has from 6 to 10 carbon atoms. In some embodiments, the aryl group is a fully aromatic hydrocarbon ring system. Preferably, the aryl group is phenyl. Aryl groups can be optionally substituted, as indicated elsewhere in the specification, and the substituent(s) may be placed at any available position in the ring system.

The term "bond" refers to a single bond, unless specifically indicated otherwise.

The term "carbocyclyl", unless otherwise specified, refers to a 3- to 18-membered non-aromatic hydrocarbon ring system which contains only hydrogen and carbon atoms and which is monocyclic or multicyclic (e.g. fused, bridged or spiro rings). Each of the rings in the ring system is fully saturated or partially unsaturated, i.e. none of the rings is aromatic. One or more ring carbon atoms of a carbocyclyl group can each be optionally oxidized to form a CO group. In some embodiments, carbocyclyl contains from 3 to 10 carbon atoms. In some embodiments, carbocyclyl is a fully saturated hydrocarbon ring system, i.e. it does not contain any unsaturation; a fully saturated carbocyclyl is also referred herein as "cycloalkyl". Examples of carbocyclyl include, but are not limited to, cyclopropyl, cyclobutyl, cyclopentyl, cyclohexyl, cycloheptyl, cyclooctyl, cyclopentenyl, cyclohexenyl, cycloheptenyl, cyclooctenyl, adamantyl, bicyclo[2.2.1]heptanyl, bicyclo[2.2.2]octanyl, decalinyl, and the like. Preferably, carbocyclyl is $C_{3-7}$ cycloalkyl. Carbocyclyl groups can be optionally substituted, as indicated elsewhere in the specification, and the substituent(s) may be placed at any available position in the ring system.

The term "$C_{3-7}$ cycloalkyl" refers to a monocyclic cycloalkyl having from 3 to 7 ring-forming carbon atoms, and includes cyclopropyl, cyclobutyl, cyclopentyl, cyclohexyl and cycloheptyl. Cycloalkyl groups can be optionally substituted, as indicated elsewhere in the specification, and the substituent(s) may be placed at any available position in the ring system.

"Halo" or "halogen" refers to bromo, chloro, fluoro or iodo. Preferably, halo is fluoro.

The term "$C_{y-z}$ haloalkyl" refers to an alkyl group having from y to z carbon atoms as defined herein which is substituted one or more times with one or more halo, which can be the same or different. Accordingly, a $C_{1-6}$ haloalkyl is a $C_{1-6}$ alkyl which is substituted one or more times with one or more halo. Haloalkyl groups include perhaloalkyl groups, i.e. alkyl groups where all hydrogen atoms are replaced by halo. Examples of haloalkyl groups include, but are not limited to, fluoromethyl, difluoromethyl, trifluoromethyl, 2,2,2-trifluoroethyl, 1-fluoro-2-fluoroethyl, pentafluoroethyl, 3,3,3-trifluoropropyl, heptafluoropropyl, 4,4,4-trifluorobutyl chloromethyl, dichloromethyl, trichloromethyl difluorochloromethyl, dichlorofluoromethyl, 1,2-dichloroethyl, 3,3-dichloropropyl and the like. In some embodiments, the haloalkyl is a fluoroalkyl, i.e. an alkyl group which is substituted one or more times with one or more fluoro.

The term "$C_{y-z}$, haloalkoxy" refers to an haloalkyl group having y to z carbon atoms as defined herein covalently linked to an oxygen atom, i.e. a group of formula —O—$C_{y-z}$ haloalkyl. A $C_{1-6}$ haloalkoxy group thus refers to a haloalkoxy group wherein the haloalkyl moiety has from 1 to 6 C atoms. Examples of haloalkoxy groups include, but are not limited to, trifluoromethoxy, 2-fluoroethoxy, pentafluoroethoxy, 3-chloropropoxy, 3-fluoropropoxy, heptafluoropropoxy, and the like.

The term "heteroaryl", unless otherwise specified, refers to a 5- to 18-membered heterocyclic ring system which is monocyclic or multicyclic (e.g. fused, bridged or spiro rings) and which comprises, in addition to C atoms, from 1 to 6 heteroatoms independently selected from N, O and S, wherein at least one of the rings in the ring system is aromatic and contains at least one of the heteroatoms. Heteroaryl as used herein thus covers fully aromatic ring systems, i.e. where all the ring(s) in the system are aromatic, like imidazolyl, pyridyl, quinolyl, pyrido[2,3-d]pyrimidinyl and the like, and groups in which an heteroaromatic ring(s) is fused to one or more non-aromatic (i.e. saturated or partially unsaturated) carbocyclic or heterocyclic rings, such as 5,6,7,8-tetrahydroquinoline, 1,2,3,4-tetrahydro-1,8-naphthyridine and the like. The heteroatom(s) can be optionally oxidized. Likewise, when the heteroaryl comprises a heteroaromatic ring fused to one or more non-aromatic carbocyclic or heterocyclic rings, one or more ring carbon atoms in the non-aromatic carbocyclic or heterocyclic ring can each be optionally oxidized to form a CO group. The heteroaryl group can be attached to the rest of the molecule through any C or N atom that results in a stable structure. In some embodiments, the point of attachment is on the heteroaromatic ring. In some embodiments, the heteroaryl group has from 1 to 4 heteroatoms. In some embodiments, the heteroaryl group has from 1 to 3 heteroatoms. In some embodiments, the heteroaryl is 5- to 6-membered monocyclic or 9- to 10-membered bicyclic. In some embodiments, the heteroaryl is 5- to 6-membered monocyclic. In some embodiments, the heteroaryl group is fully aromatic. Non-limiting examples of heteroaryl groups include pyridyl, pyrazinyl, pyrimidinyl, pyridazinyl, furyl, thienyl, pyrrolyl, imidazolyl, pyrazolyl, oxazolyl, thiazolyl, isoxazolyl, isothiazolyl, triazolyl, oxadiazolyl, thiadiazolyl, tetrazolyl, triazine, quinolinyl, isoquinolinyl, quinazolinyl, quinoxalinyl, naphthyridinyl, phthalazinyl, indolyl, benzimidazolyl, benzofuranyl, benzothienyl, benzothiazolyl, benzoxazolyl, cinnolinyl, indazolyl, indolizinyl, isoindolyl, pteridinyl, purinyl, furopyridinyl, acridinyl, phenazinyl, 5,6,7,8-tetrahydroquinoline, 1,2,3,4-tetrahydro-1,8-naphthyridine and the like. Heteroaryl groups can be optionally substituted, as indicated elsewhere in the specification, and the substituent(s) may be placed at any available position in the ring system.

The term "heterocyclyl", unless otherwise specified, refers to a 3- to 18-membered partially unsaturated or fully saturated heterocyclic ring system which is monocyclic or multicyclic (e.g. fused, bridged or spiro rings) which comprises, in addition to C atoms, from 1 to 6 heteroatoms independently selected from N, O and S. Nitrogen or sulfur atoms may be optionally oxidized (e.g., —N═O, —S(═O)—, or —S(═O)$_2$—) and additionally one or more of the ring carbon atoms of the heterocyclyl may each be optionally oxidized to form a CO group. "Heterocyclyl" as used herein also includes groups in which a partially unsaturated or fully saturated heterocyclic ring is fused to one or more phenyl rings, as in 1,2,3,4-tetrahydroquinolinyl, benzodioxolyl, carbazolyl or phthalimidyl. The heterocycyl can be attached to the rest of the molecule through any ring C or N atom that results in a stable structure. In some embodiments, the heterocyclyl is 3- to 7-membered monocyclic. Examples of heterocyclyl groups include, but are not limited to, pyrrolidinyl, 2-oxo-pyrrolidinyl, tetrahydrofuranyl, tetrahydrothienyl, tetrahydropyranyl, dihydropyranyl, tetrahydrothiopyranyl, piperidinyl, morpholinyl, thiomorpholinyl, piperazinyl, homopiperazinyl, azetidinyl, oxetanyl, homopiperidinyl, oxepanyl, thiepanyl, 2H-pyranyl, 4H-pyranyl, dioxanyl, 1,3-dioxolanyl, dithianyl, dithiolanyl, dihydropyranyl, dihydrothienyl, dihydrofuranyl, pyrrolinyl, pyrazolinyl, pyrazolidinyl, imidazolinyl, imidazolidinyl, oxazolidinyl, indolinyl, 1-oxoisoindolinyl, decahydroquinolinyl, 1,2,3,4-tetrahydroquinolinyl, 6-azabicyclo[3.3.1]heptanyl, 8-azabicyclo[3.2.1]octanyl, 3-azaspiro[5.5]undecanyl, 7-azaspiro[3.5]nonanyl, carbazolyl, phthalimidyl, tetrahydrothiopyranyl 1,1-dioxide, 2-azaspiro[4.5]decanyl, 2,3-dihydrospiro[indene-1,4'-piperidinyl], and the like. Heterocyclyl groups can be optionally substituted, as indicated elsewhere in the specification, and the substituent(s) may be placed at any available position in the ring system.

The term "optionally substituted" means unsubstituted or substituted. As used herein, the term "substituted" means that a hydrogen atom is removed and replaced by a monovalent substitutent. It is to be understood that substitution at a given atom is limited by valency. Unless defined otherwise (or limited by valency), a group that is optionally substituted with "one or more" substituents may be unsubstituted or may, for example, carry one, two or three (particularly one or two) substituents.

The term "CO" as used herein refers to a carbonyl group.

The term "partially unsaturated" as used herein in relation to a ring refers to a ring that includes at least one double bond between ring atoms but is not fully unsaturated (i.e. aromatic).

The term "saturated" is used interchangeably with "fully saturated" and as used herein in relation to a ring it refers to a ring that does not contain any unsaturation.

The term "fully aromatic" is used interchangeably with "aromatic" and as used herein in relation to a ring it refers to a ring that is fully unsaturated.

A wavy line ⌇ in chemical drawings indicates the point of attachment to the rest of the molecule.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for said R.

The compounds of the invention may contain one or more asymmetric centers and may thus give rise to stereoisomers. All stereoisomers, such as enantiomers, diastereoisomers and mixtures thereof, are intended unless otherwise indicated. Compounds of the present invention that contain asymmetrically substituted carbon atoms can be isolated in optically active form or racemic mixtures. Methods on how to prepare optically active forms from optically inactive starting materials are known in the art, and include for example by resolution of racemic mixtures or by stereoselective synthesis.

The compounds presented herein may, in certain embodiments, exist as tautomers. It should be understood that when compounds have tautomeric forms, all tautomeric forms are intended to be included in the scope of the present invention. A "tautomer" refers to a molecule wherein a proton shift from one atom to another atom of the same molecule is possible. Examples include ketone-enol pairs and annular forms where a proton can occupy two or more positions of a heterocyclic system as for example in 1H- and 3H-imidazole. Tautomeric forms can be in equilibrium or sterically locked into one form by appropriate substitution.

Compounds of the invention include unlabeled forms of the compounds of Formula (I) as well as isotopically labeled forms thereof. Isotopically labeled forms of the compounds are compounds that differ only in the replacement of one or more atoms by a corresponding isotopically enriched atom. Examples of isotopes that can be incorporated into compounds of the invention include for example isotopes of hydrogen, carbon, nitrogen, oxygen, fluorine, chlorine, and iodine, such as $^{2}H$, $^{3}H$, $^{11}C$, $^{13}C$, $^{14}C$, $^{15}N$, $^{18}O$, $^{17}O$, $^{35}S$, $^{18}F$, $^{36}Cl$, and $^{125}I$. Such isotopically labelled compounds are useful for example as probes in biological assays, as analytical tools, or as therapeutic agents.

"Polymorphs" or "crystal forms" refers to crystal structures in which a compound (or a salt or solvate thereof) can crystallize in different crystal packing arrangements, all of which have the same elemental composition. Different crystal forms usually have different X-ray diffraction patterns, infrared spectra, Raman spectra, melting points, differential scanning calorimetry (DSC) spectra, crystal shape, solubility and/or stability, among others. When compounds of the invention exist in different solid forms, all forms thereof, including amorphous forms and crystal forms, are intended to be included in the scope of the present invention.

The terms "compound of the invention", "compound as described herein" and the like are meant to include a compound of Formula (I) (including each and every subgenus of a compound of Formula (I) as described herein and in the claims as well as the compounds described in the Examples), including all stereoisomers, tautomers, isotopically labeled forms and polymorphs thereof.

The present invention also includes salts of the compounds of the invention. Preferably, said salts are pharmaceutically acceptable salts. As used herein, a "pharmaceutically acceptable salt" is intended to mean a salt that retains the biological effectiveness and properties of the parent compound (i.e. the free acid or free base, as applicable) and that is not biologically or otherwise undesirable. Pharmaceutically acceptable salts include salts formed with inorganic or organic bases, and salts formed with inorganic and organic acids. Pharmaceutically acceptable salts are well known in the art. Exemplary pharmaceutically acceptable salts include those salts prepared by reaction of the compounds of the present invention with a mineral or organic acid, such as hydrochlorides, hydrobromides, sulfates, pyrosulfates, bisulfates, sulfites, bisulfites, phosphates, monohydrophosphates, dihydrophosphates, metaphosphates, pyrophosphates, chlorides, bromides, iodides, nitrates, acetates, haloacetates (e.g. trifluoroacetates), propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, ethane-sulfonates, propane-sulfonates, benzenesulfonates, toluenesulfonates, trifluoromethansulfonates, naphthalene-1-sulfonates, naphthalene-2-sulfonates, mandelates, pyruvates, stearates, ascorbates, or salicylates. When the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands such as ammonia, alkylamines, hydroxyalkylamines, lysine, arginine, N-methylglucamine, procaine and the like. The pharmaceutically acceptable salts of the present invention can be prepared from the parent compound which contains a basic or acidic moiety by conventional chemical methods. For example, such salts can be prepared by reacting the free acid or base forms of these compounds with a stoichiometric amount of the appropriate base or acid in a suitable solvent.

Additionally, compounds of the present invention, or salts thereof, may exist in hydrated or unhydrated (anhydrous) form or as solvates with other solvent molecules. "Solvate" as used herein means solvent addition forms that contain either stoichometric or non-stoichometric amounts of solvent. Some compounds have a tendency to trap a fixed molar ratio of solvent molecules in the crystalline solid state, thus forming a solvate. If the solvent is water, the solvate formed is a hydrate. Non-limiting examples of solvates include hydrates and solvates with alcohols (also named alcoholates) such as ethanol (ethanolates). When compounds of the invention (or salts thereof) exist as solvates, all solvates thereof are intended to be included in the scope of the present invention, particularly pharmaceutically acceptable solvates. As used herein a "pharmaceutically acceptable solvate" is a solvate formed with a pharmaceutically acceptable solvent. Pharmaceutically acceptable solvents are well known in the art and include solvents such as water and ethanol.

Compounds of the invention, including salts thereof, can be prepared using a number of synthetic routes, including the general synthetic routes described below, starting from commercially available starting materials, compounds known in the literature, or from readily prepared intermediates, by employing standard synthetic methods and procedures. Standard synthetic methods and procedures for the preparation of organic compounds and functional group transformations and manipulations are known in the art and can be found in standard textbooks such as Smith M. B., "*March's Advanced Organic Chemistry: Reactions, Mechanisms, and Structure*", 7$^{th}$ Edition, Wiley, 2013; Greene T W and Wuts P G M "*Greene's Protective Groups in Organic Synthesis*", 4$^{th}$ edition, Wiley, 2006)

The reaction schemes described below are only meant as illustrative of methods to obtain the compounds of the invention. Other routes known by the ordinary skilled artisan, as well as other reactants and intermediates, can also be used to arrive at the compounds of Formula (I).

In some of the processes described below it may be necessary or advisable to protect reactive or labile groups with conventional protecting groups. Both the nature of these protecting groups and the procedures for their introduction and removal are well known in the art (see for example Greene T W and Wuts P G M, cited supra). Whenever a protecting group is present, a subsequent deprotection step will be required, which can be performed under standard conditions well known in the art, such as those described in the above reference.

Unless otherwise stated, in the methods described below the meanings of the different substituents in each synthetic intermediate and in each compound of Formula (I) are the meanings described above.

In general, the compounds of Formula (I) can be obtained following the procedure shown in Scheme 1 below.

Scheme 1

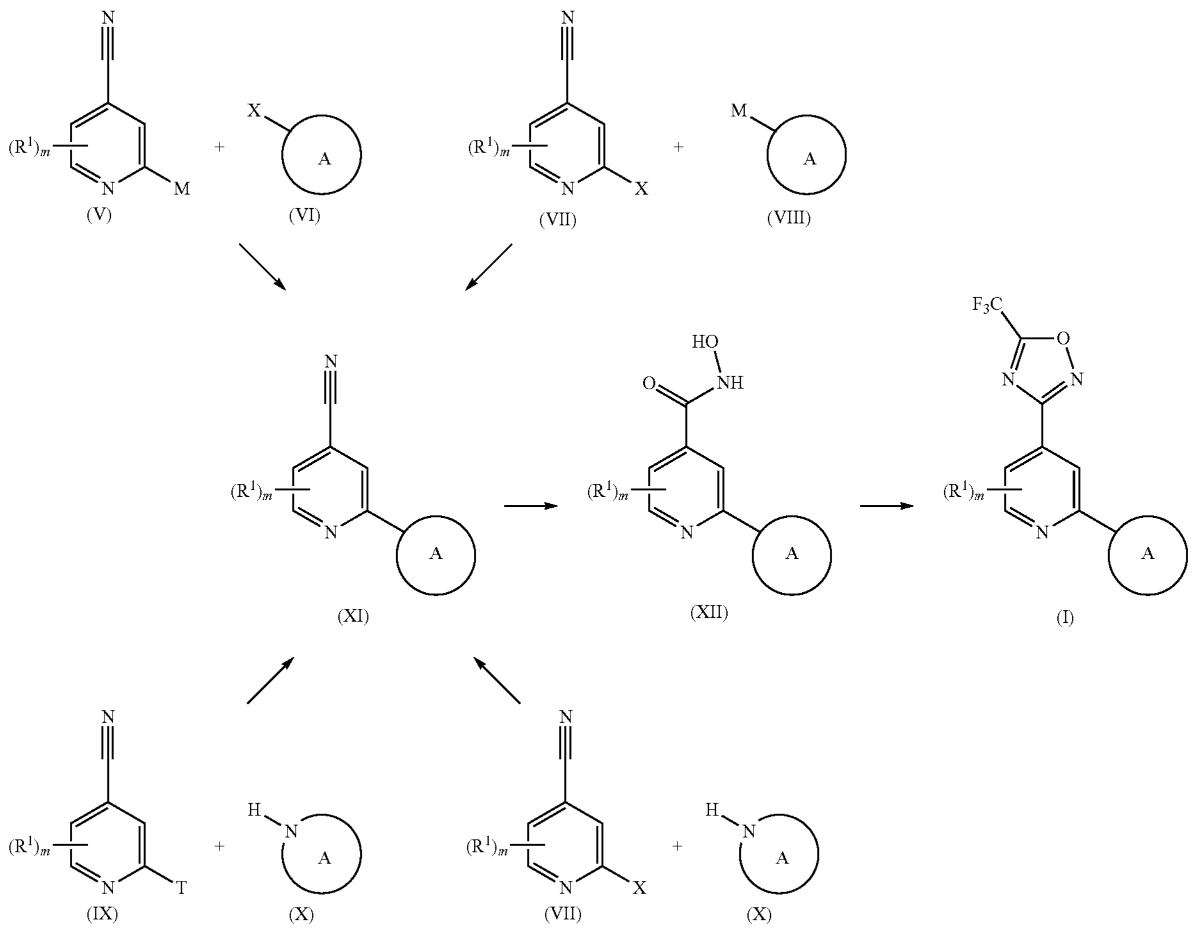

wherein $R^1$, m and ring A have the same meaning described for compound of Formula (I), and M, T and X have the meaning defined below.

Ring A can be attached to the rest of the molecule via a ring C atom or a ring N atom of A. When ring A is attached via a ring C atom, compound of Formula (XI) is obtained via a cross-coupling reaction of a organometallic species (V) or (VIII) with a halide (VI) or (VII).

Several cross-coupling reactions can be used for the coupling of a compound of Formula (V) with a compound of Formula (VI) or a compound of Formula (VII) with a compound of Formula (VIII), including: a Suzuki cross coupling where M is a boronic acid or boron derivative and X is Cl, Br or I; a Stille reaction where M is trialkylstannanyl group and X is Cl, Br or I; a Negishi coupling where M is a zinc halide and X is triflate, Cl, Br or I; and a Hiyama coupling where M is a trialkylsilyl group and X is Cl, Br or I.

When compounds of Formula (XI) are prepared through a Suzuki cross coupling with the intermediates indicated in Scheme 1, the reaction can be performed using a suitable Pd/ligand combination such as XPhos and $Pd_2(dba)_3$ or $Pd(PPh_3)_4$, in the presence of a suitable Cu salt such as $Cu(OAc)_2$ or CuI, in a suitable solvent such as tetrahydrofuran or dimethylformamide, using a suitable base such as potassium carbonate. The temperature of the reaction typically can go from room temperature to 120° C. and the time of reaction typically from 1 h to 48 h. Examples of boronic derivatives include among others diethyl, dimethyl, N-methyliminodiacetic acid (MIDA) derivative and 2,2'-(phenylazanediyl)bis(ethan-1-ol) derivative.

When compounds of Formula (XI) are prepared through a Stille cross coupling with the intermediates indicated in Scheme 1, the reaction can be performed using a suitable Pd/ligand combination such as $Pd(PPh_3)_4$, $Pd(PPh_3)Cl_2$ or $Pd(dppb)Cl_2$ in the presence of a suitable Cu salt such as CuI or CuO, in the presence or absence of CsF, in a suitable solvent such as tetrahydrofuran, dioxane or dimethylformamide. The temperature of the reaction can typically go from room temperature to 120° C. and the time of reaction typically from 1 h to 48 h. The organotin employed can be trimethylstannyl derivative. An intermolecular Stille Kelly reaction can also be used, in which both reagents are halo derivatives and are treated with $(Bu_3Sn)_2$, $Et_4N1$, and a Pd/ligand combination.

When compounds of Formula (XI) are prepared through a Negishi cross coupling with the intermediates indicated in Scheme 1, the reaction can be performed using a suitable Pd/ligand combination such as $PPh_3$ and $Pd_2(dba)_3$, XPhos and $Pd_2(dba)_3$, RuPhos and $Pd_2(dba)_3$ or $Pd(PPh_3)_4$, in a suitable solvent such as tetrahydrofuran, dioxane or dimethylformamide. The temperature of the reaction can typically go from room temperature to 120° C. and the time of reaction typically from 1 h to 48 h.

When compounds of Formula (XI) are prepared through a Hiyama cross coupling with the intermediates indicated in Scheme 1, the reaction can be performed using a suitable Pd/ligand combination such as $PdCl_2(PPh_3)_2$ and $PPh_3$ or $Pd(OAc)_2$ and di(1-adamantyl)-n-butylphosphine in the presence of a suitable Cu salt such as CuI or CuBr, in the presence or absence of tetrabutylammonium fluoride in a suitable solvent such as tetrahydrofuran, dioxane or dimethylformamide. The temperature of the reaction can typically go from room temperature to 120° C. and the time of reaction typically from 1 h to 48 h. When ring A is attached via a ring N atom, compound of Formula (XI) is obtained by reaction of a compound of Formula (IX) and a compound of Formula (X) (wherein the ring N atom in A that will form the bond to the rest of the molecule is in NH form) through a cross coupling reaction or alternatively, between a compound of Formula (VII) and a compound of Formula (X) through a displacement reaction. In the case of a cross-coupling reaction, the Chan-Lam reaction can be used for the coupling of a compound of Formula (IX) with a compound of Formula (X).

This reaction allows carbon-heteroatom bond formation via an oxidative coupling of boronic acids, stannanes or siloxanes with N—H containing compounds in the presence of air. T in compounds of Formula (IX) is a boron, tin or silicon derivative. The reaction is induced by a stoichiometric or catalytic amount of copper salt such as $Cu(OAc)_2$ or CuI, in the presence or absence of a base such as $NEt_3$, pyridine or DMAP in a suitable solvent such as $CH_2Cl_2$, pyridine or DMSO in the presence of air. The temperature of the reaction can typically go from room temperature to 120° C. and the time of reaction typically from 1 h to 48 h. Alternatively, a compound of formula (XI) can be obtained by displacement reaction between a compound of Formula (VII) and a compound of Formula (X), which can be carried out in the presence of a base such as $CsCO_3$, tBuOK, $K_2CO_3$ NaH or pyridine and in the presence or absence of copper derivative such as $Cu_2O$ or CuI in a suitable solvent such as DMF, DMSO or THF. The temperature of the reaction can typically go from room temperature to 120° C. and the time of reaction typically from 1 h to 48 h.

Compounds of Formula (I) are obtained in two steps from a cyano derivative of Formula (XI). In a first step, the cyano derivative of Formula (XI) is transformed into the N'-hydroxyimidamide of Formula (XII) by reaction with hydroxylamine, which is then followed by condensation of (XII) with trifluoroacetic anhydride to give a compound of Formula (I). Addition of hydroxylamine to cyano derivatives (XI) is carried out in a suitable solvent such as EtOH or MeOH, and in the presence of base in the case hydroxylamine chlorhydrate is used.

The temperature of the reaction can typically go from room temperature to 60° C. and the time of reaction typically from 1 h to 48 h. The condensation of N'-hydroxyimidamides (XII) with trifluoroacetic anhydride in a suitable solvent such as $CH_2Cl_2$ or THF gives the corresponding N'-trifluoroacethyloxyimidamide that in the same reaction medium or after the addition of trilfuoroacetic acid yield 1,2,4-oxadiazoles of Formula (I).

Alternatively, compounds of Formula (I) can also be prepared in three steps building the 1,2,4-oxadiazole from cyano derivative (VII) before the cross-coupling or displacement reaction with appropriate ring A derivatives. Reaction of cyano derivative (VII) with hydroxylamine gives intermediate (XIII) that is then condensed with trifluoroacetic anhydride to give a compound of formula (XIV), which is then subjected to cross coupling or displacement reactions with an appropriate ring A derivative to give a compound of Formula (I), as outlined in Scheme 2. When a cross-coupling reaction is used to convert a compound (XIV) to a compound of Formula (I), organometallic species can be generated either from a halo derivative of formula (XIV) or from appropriate ring A derivatives, as in Scheme 1. The reactions outlined in Scheme 2 can be performed under the same reaction conditions described above for Scheme 1.

Scheme 2

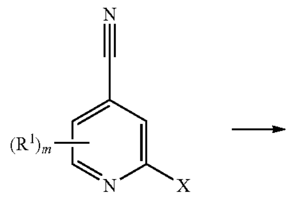

(VII)

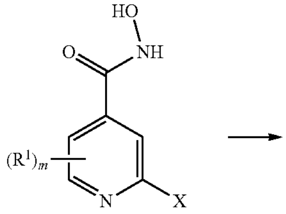

(XIII)

-continued

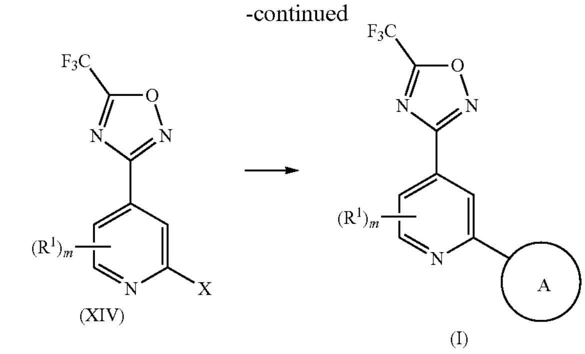

wherein $R^1$, m and ring A have the same meaning described for compound of Formula (I), and X has the meaning defined above.

The compounds of Formula (V), (VI), (VII), (VIII), (IX), and (X) are commercial or can be obtained following standard procedures well known to those skilled in the art of organic chemistry.

Organometallic derivatives of Formula (V), (VIII), (IX) and those derived from compounds of Formula (XIV) can be obtained from compounds of Formula (VII) and (XIV) by transmetallation following standard procedures in the preparation of reagents for Suzuki, Stille Hiyama, Negishi and Chan-Lam couplings, well known to those skilled in the art of organic chemistry. For example, N-methyliminodiacetic acid boronate derivatives can be prepared by reaction of compounds of Formula (VII) and (XIV) with nBuLi in the presence of $B(OiPr)_3$ at −78° C. followed by the addition of N-methyliminodiacetic acid; trimethyltin derivatives can be prepared by reaction of compounds of Formula (VII) and (XIV) with hexamethylditin and Pd $(PPh_3)_4$ in toluene at 110° C. for 16 h; organozinc derivatives can be prepared from compounds of Formula (VII) and (XIV) by treatment with Zn in THF at room temperature for 1 to 6 h; and trimetilsilyl derivatives can be prepared by reaction of compounds of Formula (VII) and (XIV) with nBuLi in the presence of trimethylsylchloride at −78° C. in THF.

Introduction of substituents $R^2$ and $R^3$ onto ring A as well as transformations in $R^2$ and $R^3$ substituents of ring A can be done following standard procedures well known to those skilled in the art of organic chemistry. Said standard procedures include, for example: the substitution of a primary or secondary amines by treatment with an alkylating agent under standard conditions; or by reductive amination, i.e. by treatment with an aldehyde or a ketone in the presence of a reducing agent such as sodium cyanoborohydride or sodium triacetoxyborohydride; the conversion of an amine into an amide by means of activating agents such us dicyclohexyl carbodiimide (DCC), 1-hydroxybenzotriazole (HOBT), N-hydroxysuccinimide (HOSu), 1-ethyl-3-(3'-dimethylamino)carbodiimide (EDC) in the presence of a base, such as, disopropylethylamine, pyridine, thriethylamine, or N-methylmorpholine, in a solvent, such as dimethoxyethane, N,N-dimethylformamide, tetrahydrofuran, dichloromethane or dioxane or alternatively, by reaction with acid chlorides in the presence of a suitable base; the alkylation of an amide by treatment with an alkylating agent under basic conditions; the conversion of an alcohol into an ether under standard conditions; the partial or total oxidation of an alcohol to give a ketone under standard oxidizing conditions; the reduction of a ketone by treatment with a reducing agent such as sodium borohydride; the conversion of an alcohol into a halogen by reaction with $SOCl_2$, $PBr_3$, tetrabutylammonium bromide in the presence of $P_2O_5$, or $PCl_3$; the conversion of halogen into an amine by reaction with an amine, optionally in the presence of a suitable solvent, and preferably heating; and the conversion of a primary amide into a —CN group under standard conditions.

Likewise, any of the aromatic rings of the compounds of the present invention can undergo electrophilic aromatic substitution reactions or nucleophilic aromatic substitution reactions, widely described in the literature.

Some of these interconversion reactions are explained in greater detail in the examples. As it will be obvious to those skilled in the art, these interconversion reactions can be carried out upon a compound of Formula (I), thus generating further compounds of Formula (I), as well as upon any suitable synthesis intermediate thereof.

The salts of a compound of Formula (I) can be obtained during the final isolation and purification of the compounds of the invention or can be prepared by treating a compound of Formula (I) with a sufficient amount of the desired acid (or base) to give the salt in a conventional manner.

Where the processes for the preparation of the compounds of the invention give rise to mixtures of stereoisomers, individual stereoisomers of a compound of Formula (I) can be obtained for example by resolution, starting from a compound of formula (I) obtained as a mixture of stereoisomers, using well known methods such as formation of diastereomeric pairs by salt formation with an optically active acid followed by fractional crystallization and regeneration of the free base, or by chiral preparative chromatography. Alternatively, it is possible to obtain optically pure or enantiomerically enriched synthetic intermediates, which can then be used as such in subsequent steps, at various stages of the synthetic procedures described above, using any known method for chiral resolution. Alternatively, it is possible to obtain optically pure or enantiomerically enriched final compounds (or synthetic intermediates) by using chiral chromatography.

The compounds of the invention inhibit the activity of histone deacetylases. In particular, the compounds of the invention have been found to be potent inhibitors of HDAC6. The activity of the compounds of the invention as HDAC6 inhibitors can be determined using for example the in vitro assays described in the Examples section. In particular, Example 8 describes a method to determine HDAC6 inhibitory activity. The compounds of the invention have been found to be potent HDAC6 inhibitors using the assay described in Example 8. Compounds of the invention have also been shown to inhibit HDAC6 activity in cells, as shown by the results described in Example 9. Selectivity towards HDAC6 compared to other HDAC isoforms can be assayed using methods well known in the art, for example in vitro assays similar to the one described in Example 8 using the corresponding HDAC isoform of interest. Compounds of the invention have been found to exhibit selectivity towards HDAC6 vs HDAC2, as shown by the results in Example 8 against HDAC2 using representative compounds of the invention.

HDAC6 is a class IIb HDAC that can deacetylate substrates, such as tubulin, heat shock protein (Hsp)90 and cortactin. HDAC6 localizes in the cytosol and possesses two catalytic domains and a C-terminal zinc finger domain that can bind free ubiquitin as well mono- and polyubiquitinated proteins (Li et al, FEBS J. 2013 February; 280(3):775-93). The ubiquitin-binding domain in HDAC6 associates with several proteins involved in the control of the ubiquitin, proteasome system, aggresome formation and autophagy. Additionally, the ability of HDAC6 to deacetylate alpha-tubulin affects microtubule-mediated processes such as cell migration, immune synapse formation, viral infection, the degradation of misfolded proteins and of stress granule. HDAC6 has also been shown to deacetylate Hsp90 and modulate its chaperone activity, thus modulating various Hsp90-associated cell signaling pathways such as the control of stress-related response.

Many studies have reported the role of HDAC6 in cancer. For example, inhibition of HDAC6 was shown to reduce growth of multiple myeloma in preclinical models and to enhance the effect of proteasome inhibitors and thalidomide-based Immunomodulatory drugs used as standards of care (Santo et al, Blood. 2012 Mar. 15; 119(11):2579-89; North et al, PLoS One. 2017 Mar. 6; 12(3):e0173507). Inhibition of HDAC6 was also shown to increase the effect of other standard of care drugs such as paclitaxel in ovarian, pancreatic and breast cancer cells (Huang et al, Oncotarget 2017 Jan. 10; 8(2):2694-2707). The antiproliferative activity of HDAC6 inhibitors has also been observed in prostate cancer and melanoma cells (Li et al, Eur J Med Chem. 2015 Jul. 15; 100:270-6; Seidel et al, Biochem Pharmacol. 2016 Jan. 1; 99:31-52). In addition, in vivo efficacy of HDAC6 inhibitors has been reported in colorectal, inflammatory breast cancer, leukemia, lymphoma and ARID1A mutant ovarian xenograft models (Yang et al, J Med Chem. 2016 Feb. 25; 59(4):1455-70; Putcha et al, Breast Cancer Res. 2015 Dec. 8; 17(1):149; Bitler et al, Nat Cell Biol. 2017 August; 19(8):962-973). Similarly, HDAC6 knock down reduces uterine leiomyoma and gastric cancer cell proliferation, while HDAC6 overexpression promotes proliferation and promotes drug-resistance of non-small cell lung cancer cells and glioblastoma cells (Wei et al, Reprod Sci. 2011 August; 18(8):755-62; Park et al, Cancer Lett. 2014 Nov. 1; 354(1):97-106; Wang et al, Oncol Rep. 2016 July; 36(1):589-97; Wang et al, Cancer Lett. 2016 Aug. 28; 379(1):134-42). Furthermore, HDAC6 inhibitors were shown to have anticancer activity by stimulating the immune-response against the tumors in models of melanoma and non-small cell lung cancer when used alone or in combination with immune-checkpoints inhibitors or epigenetic modulators (Knox et al, Abstract 4055, AACR Annual Meeting 2017; Apr. 1-5, 2017; Washington, DC; Woan et al, Mol Oncol. 2015 August; 9(7): 1447-1457; Tavares et al, ACS Med Chem Lett. 2017 Sep. 5; 8(10):1031-1036; Adeegbe et al, Cancer Discov. 2017 August; 7(8):852-867).

HDAC6 has also been widely reported to play a role in inflammatory and autoimmune diseases. Knock out mice for HDAC6 have an increased number of circulating regulatory T cells (Tregs), which are key to the maintenance of immune homeostasis. Likewise, HDAC6 specific inhibitors promote Treg suppressive activity in models of inflammatory bowel disease and graft versus host disease (de Zoeten et al, Mol Cell Biol. 2011 May; 31(10):2066-78). HDAC6 inhibitors were shown to have disease modifying activity in models of inflammation, rheumatoid arthritis and systemic lupus erythematosus (Vishwakarma et al, Int Immunopharmacol. 2013 May; 16(1):72-8; Regna et al, Clin Immunol. 2016 January; 162:58-73). Mice lacking HDAC6 display reduction of autophagy, which ameliorates chronic obstructive pulmonary disease (COPD)-associated cilia dysfunction (Lam et al, J Clin Invest. 2013 December; 123(12):5212-30).

HDAC6 inhibitors have also been reported to be effective to treat ciliopathies. Ciliopathies are genetic diseases associated with defects in ciliary structure or function, and include, among others, polycystic kidney disease, polycystic liver disease, Bardet-Biedl syndrome and retinal degeneration. In a model of polycystic kidney disease, HDAC6 inhibitors prevented cyst formation and improved renal function (Cebotaru et al, Kidney Int. 2016 July; 90(1):90-9). Similarly, in a model of polycystic liver disease, pharmacological inhibition of HDAC6 decreased proliferation of cystic cholangiocytes, and diminished liver cyst development and fibrosis (Gradilone et al, Am J Pathol. 2014 March; 184(3):600-8).

HDAC6 has also been shown to have an important role in diseases of the nervous system. In particular, HDAC6 inhibitors showed efficacy in models of peripheral neuropathies such as Charcot-Marie-Tooth disease and chemotherapy-induced peripheral neuropathy (Benoy et al, Neurotherapeutics. 2017 April; 14(2):417-428; Krukowski et al, Pain. 2017 June; 158(6):1126-1137). In addition, in neuronal culture derived from patients with amyotrophic lateral sclerosis, treatment with HDAC6 inhibitors rescued their defective phenotype (Guo et al, Nat Commun. 2017 Oct. 11; 8(1): 861).

HDAC6 inhibitors have also been reported to be effective to treat several other diseases of the nervous system. For example, reduction or inhibition of HDAC6 has been shown to rescue memory and improve cognition in mouse models of Alzheimer's disease (Govindarajan et al, EMBO Mol Med. 2013 January; 5(1):52-63). Loss or inhibition of HDAC6 suppresses neuritic tau accumulation, thus HDAC6 inhibition could be useful to treat not only Alzheimer's disease but also other human 4-repeat tauopathies such as corticobasal degeneration and progressive supranuclear palsy (Tseng et al, Cell Rep. 2017 Aug. 29; 20(9):2169-2183). Furthermore, in a model of Huntington's disease, HDAC6 inhibition reduces the vulnerability of neurons to mutant huntingtin, thus suggesting a neuroprotective effect of HDAC6 inhibitors in HD (Guedes-Dias et al, Biochim Biophys Acta. 2015 November; 1852(11):2484-93).

HDAC6 has also been reported to play a role in mental and behavioural disorders such as depression. For example, HDAC6 inhibitors stimulated the mouse exploratory behaviors and had a positive effect in anxiolytic and social interaction tests (Jochems et al, Neuropsychopharmacology. 2014 January; 39(2):389-400).

Moreover, several publications underline the important role of HDAC6 in infectious diseases. The use of HDAC6 inhibitors reduced the replication of viruses such as Japanese Encephalitis Virus (JEV), hepatitis C virus (HCV) and Rabies Virus (Lu et al, Int J Mol Sci. 2017 May 1; 18(5); Zan et al, Front Cell Infect Microbiol. 2017 Apr. 26; 7:146; Ai et al, J Med Chem. 2015 Jan. 22; 58(2):785-800). HDAC6 was also shown to facilitate cell entry of influenza A viruses and to control the viral lytic-latency switch of other viruses (Banerjee et al, Science 2014 Oct. 24; 346(6208):473-7). For example, HDAC6 was reported to be involved in the maintenance of HIV latency, thus inhibition of HDAC6 could promote the body clearance of the virus (Huo et al, J Biol Chem. 2011 Mar. 18; 286(11):9280-6). Furthermore, selective HDAC6 inhibitors improved survival and bacterial clearance in models of sepsis (Zhao et al, J Trauma Acute Care Surg. 2016 January; 80(1):34-40).

Several publications have also reported a role of HDAC6 in cardiovascular diseases. Knockout mice for HDAC6 display improved heart condition in mouse models of heart failure. Moreover, HDAC6 null mice are resistant to skeletal muscle wasting considered a life threatening complication in congestive heart failure (Demos-Davies et al, Am J Physiol Heart Circ Physiol. 2014 Jul. 15; 307(2):H252-8). Pharmacological inhibition of HDAC6 was shown to protect against atrial remodeling in connection to atrial fibrillation (Zhang et al, Circulation. 2014 Jan. 21; 129(3):346-58). HDAC6 activity was consistently increased in stressed myocardium, thus suggesting a role for HDAC6 inhibitors in myocardiopathies (Lemon et al, J Mol Cell Cardiol. 2011 July; 51(1):41-50). Selective inhibition of HDAC6 has also been reported to improve survival in a rodent model of hemorrhagic shock (Chang et al, J Trauma Acute Care Surg. 2015 December; 79(6):905-10). Furthermore, inhibition of HDAC6 improved established pulmonary artery hypertension in experimental models and exerts a neuroprotective effect in models of brain ischemia (Boucherat et al, Sci Rep. 2017 Jul. 3; 7(1):4546; Liesz et al, J Neurosci. 2013 Oct. 30; 33(44):17350-62).

The compounds of the invention are thus expected to be useful for treating diseases associated with HDACs, in particular HDAC6. Examples of diseases associated with HDAC6 include, without limitation, the diseases listed below:

Cancers, such as: lung cancer, colon cancer, breast cancer, prostate cancer, liver cancer, brain cancer and others CNS neoplasms, kidney cancer, ovarian cancer, stomach cancer, skin cancer, bone cancer, gastric cancer, pancreatic cancer, cardiac cancer, glioma, glioblastoma, esophageal cancer, hepatocellular carcinoma, bone and joint cancer, papillary renal carcinoma, head and neck squamous cell carcinoma, sarcomas, mesothelioma, leukemias, lymphomas, and myelomas;

Autoimmune or inflammatory diseases, such as: rheumatoid arthritis, osteoarthritis, rheumatoid spondylitis, psoriatic arthritis, infectious arthritis, progressive chronic arthritis, deforming arthritis, traumatic arthritis, gouty arthritis, Reiter's syndrome, polychondritis, acute synovitis and spondylitis, psoriasis, post ischemic perfusion injury, inflammatory bowel disease (e.g. ulcerative colitis or Crohn's disease), eczema, ischemia/reperfusion injury, glomerulonephritis, hemolytic anemia, aplastic anemia, idiopathic thrombocytopenia, neutropenia, chronic thyroiditis, Graves' disease, diabetes type I, scleroderma, diabetes, hepatitis, primary binary cirrhosis, systemic inflammatory response syndrome, postoperative or posttraumatic inflammation, myasthenia gravis, pemphigus, alcoholic liver disease, cystic fibrosis, multiple sclerosis (MS), Addison's disease, Castleman's disease, polyarteritis nodosa, systemic lupus erythematosus, atopic dermatitis, contact dermatitis, chronic renal insufficiency, Stevens-Johnson syndrome, idiopathic sprue, sarcoidosis, Guillain-Barre syndrome, uveitis, conjunctivitis, keratoconjunctivitis, otitis media, periodontal disease, pulmonary interstitial fibrosis, acute respiratory distress syndrome, asthma, bronchitis, rhinitis, sinusitis, pancreatitis, inflammatory bone disease, meningitis, cystitis, pharyngolaryngitis, pneumoconiosis, pulmonary insufficiency syndrome, pulmonary emphysema, chronic obstructive pulmonary disease (COPD), pulmonary fibrosis, silicosis, chronic inflammatory pulmonary disease, or peritoneal fibrosis;

Transplant rejection, including host versus graft disease, graft versus host disease and allograft rejection. Infectious diseases, including influenza, viral encephalitis, HIV, hepatitis of viral origin, pneumonia and sepsis. Ciliopathies, such as polycystic kidney disease, polycystic kidney disease, Alstrom syndrome, Bardet-Biedl syndrome, some forms of retinal degeneration, Joubert syndrome, Meckel-Gruber syndrome, nephronophthisis, orofaciodigital syndrome 1, Senior-Loken syndrome, primary ciliary dyskinesia (Kartagener Syndrome), orasphyxiating thoracic dysplasia (Jeune), Marden-Walker syndrome, or isomerism;

Diseases of the nervous system, such as Wilson's disease, prion disease, Parkinson's disease, Huntington's disease, amyotrophic lateral sclerosis, amyloidosis, Alzheimer's disease, Alexander's disease, Pick's Disease, spinal muscular dystrophy, Lewy body dementia, chemotherapy-induced cognitive dysfunction, mitochondrial encephalomyopathies and gut dysmotility syndromes, motor neurogenesis disease (MND), ataxia syndromes including Friedreich's ataxia and spinocerebellar ataxia (SCA), spinal cord injury, olivopontocerebellar atrophy, multiple system atrophy, progressive supranuclear palsy, synucleinopathies, Down Syndrome, corticodentatonigral degeneration, progressive familial myoclonic epilepsy, strionigral degeneration, torsion dystonia, familial tremor, Gilles de la Tourette syndrome, Shy-Drager syndrome and Hallervorden-Spatz disease, as well as peripheral neuropathies such as Charcot-Marie Tooth Disease, peripheral neuropathy induced by chemotherapeutic agents (e.g. platinum-based chemoterapeutic, taxane, vincristine, bortezomib, etc.) and the like;

Mental and behavioral disorders, including psychotic disorders and schizophrenia spectrum disorders such as schizotypal (personality) disorder, delusional disorder, brief psychotic disorder, schizophreniform disorder, schizophrenia, schizoaffective disorder, substance/medication-induced psychotic disorder, and psychotic disorder due to another medical condition; bipolar disorders such as bipolar I disorder, bipolar II disorder, cyclothymic disorder, substance/medication-induced bipolar and related disorder; depressive disorders, such as disruptive mood dysregulation disorder, major depressive disorder, single and recurrent episodes, persistent depressive disorder (dysthymia), premenstrual dysphoric disorder, substance/medication-induced depressive disorder, and depressive disorder due to another medical condition; anxiety disorders, such as separation anxiety disorder, selective mutism, specific phobia, social anxiety disorder (social phobia), panic disorder, agoraphobia, generalized anxiety disorder and the like;

Cardiovascular diseases such as heart failure, myocardiopathy, atrial fibrillation, pulmonary artery hypertension, hemorrhagic shock, stroke, ischemic heart disease, myocarditis and valvular disease; Muscle Atrophy; and Cachexia.

For the uses and methods of treatment described herein, any of the compounds of the invention, including any of the embodiments thereof, may be used.

Accordingly, the invention further provides a compound of Formula (I), or pharmaceutically acceptable salt thereof, for use as a medicament.

The present invention further provides a compound of Formula (I), or a pharmaceutically acceptable salt thereof, for use in the treatment of a disease associated with HDAC6.

The present invention further provides the use of a compound of Formula (I), or a pharmaceutically acceptable salt thereof, for the manufacture of a medicament for the treatment of a disease associated with HDAC6.

The present invention further provides the use of a compound of Formula (I), or a pharmaceutically acceptable salt thereof, for treating a disease associated with HDAC6.

The present invention further provides a compound of Formula (I), or a pharmaceutically acceptable salt thereof, for use as a HDAC6 inhibitor.

The present invention further provides a method for treating a disease associated with HDAC6, comprising administering a therapeutically effective amount of a compound of Formula (I), or a pharmaceutically acceptable salt thereof, to a patient in need thereof.

The present invention further provides a method of inhibiting HDAC6 activity, comprising administering to a patient in need of said treatment an amount of a compound of Formula (I), or a pharmaceutically acceptable salt thereof, sufficient to inhibit HDAC6 activity.

The present invention further provides a compound of Formula (I), or a pharmaceutically acceptable salt thereof, for use in the treatment of a disease selected from cancer, an autoimmune or inflammatory disease, transplant rejection, a ciliopathy, a disease of the nervous system, a mental or behavioral disorder, an infectious disease, a cardiovascular disease, muscle atrophy and cachexia.

The present invention further provides the use of a compound of Formula (I), or a pharmaceutically acceptable salt thereof, for the manufacture of a medicament for the treatment of a disease selected from cancer, an autoimmune or inflammatory disease, transplant rejection, a ciliopathy, a disease of the nervous system, a mental or behavioral disorder, an infectious disease, a cardiovascular disease, muscle atrophy and cachexia.

The present invention further provides the use of a compound of Formula (I), or a pharmaceutically acceptable salt thereof, for treating a disease selected from cancer, an autoimmune or inflammatory disease, transplant rejection, a ciliopathy, a disease of the nervous system, a mental or behavioral disorder, an infectious disease, a cardiovascular disease, muscle atrophy and cachexia.

The present invention further provides a method for treating a disease selected from cancer, an autoimmune or inflammatory disease, transplant rejection, a ciliopathy, a disease of the nervous system, a mental or behavioral disorder, an infectious disease, a cardiovascular disease, muscle atrophy and cachexia, comprising administering a therapeutically effective amount of a compound of Formula (I), or a pharmaceutically acceptable salt thereof, to a patient in need thereof.

The present invention further provides a method of inhibiting HDAC6 activity in a sample (e.g. a biological sample), comprising contacting said sample (e.g. said biological sample) with a compound of Formula (I), or pharmaceutically acceptable salt thereof.

The present invention further provides the use of a compound of Formula (I), or a pharmaceutically acceptable salt thereof, as a HDAC6 inhibitor in research, particularly as a research tool compound for inhibiting HDAC6. Accordingly, the invention relates to the in vitro use of a compound of Formula (I), or a pharmaceutically acceptable salt thereof, as a HDAC6 inhibitor and, in particular, to the in vitro use of a compound of Formula (I), or a pharmaceutically acceptable salt thereof, as a research tool compound acting as a HDAC6 inhibitor. The invention likewise relates to a method, particularly an in vitro method, of inhibiting HDAC6, the method comprising applying a compound of Formula (I), or a pharmaceutically acceptable salt thereof, to a sample (e.g., a biological sample). It is to be understood that the term "in vitro" is used in this specific context in the sense of "outside a living human or animal body", which includes, in particular, experiments performed with cells, cellular or subcellular extracts, and/or biological molecules in an artificial environment such as an aqueous solution or a culture medium which may be provided, e.g., in a flask, a test tube, a Petri dish, a microtiter plate, etc.

Unless otherwise stated, any description of a method of treatment includes use of the compounds to provide such treatment as is described herein, as well as use of the compounds to prepare a medicament to treat such condition.

Any reference to a compound of Formula (I) herein includes a reference to any of the compounds of Formula (IIa), (IIb), (IIIa), (IIIb), (IVa), (IVa-1), (IVb) and (IVb-1), and to any embodiments thereof as described herein.

The term "disease associated HDAC6" and the like refer to any disease or condition in which HDAC6 plays a role, and/or where the disease or condition is associated with expression or activity of a HDAC6, and/or diseases or conditions the course of which can be influenced by modulating HDAC6. Diseases associated with HDAC6 include, without limitation, the diseases and conditions as described herein. Preferably, the disease associated with HDAC is a disease selected from cancer, an autoimmune or inflammatory disease, transplant rejection, a ciliopathy, a disease of the nervous system, a mental or behavioral disorder, an infectious disease, a cardiovascular disease, muscle atrophy and cachexia.

As used herein, the term "subject" or "patient" or "individual" refers to any animals, including mammals, preferably mice, rats, other rodents, rabbits, dogs, cats, swine, cattle, sheep, horses, or primates, and most preferably humans (e.g., a male human or a female human).

As used herein, the term "biological sample" includes, without limitation, a cell, cell cultures or extracts thereof; biopsied material obtained from an animal, e.g. a human, or extracts thereof; and blood, saliva, urine, feces, or any other body fluids or extracts thereof.

As used herein, the term "therapeutically effective amount" refers to the amount of active compound that elicits the biological or medicinal response that is being sought in subject (preferably a human). Accordingly, a therapeutically effective amount of a compound may be an amount which is sufficient to treat a disease or disorder, delay the onset or progression of a disease or disorder, and/or alleviate one or more symptoms of the disease or disorder, when administered to a subject suffering from said disease or disorder. The precise effective amount for a subject will depend upon a variety of factors such as the subject's body weight, size and health, the nature and extent of the condition to be treated, and the therapeutic or combination of therapeutics selected for administration. Therapeutically effective amounts for a given situation can be determined by routine experimentation that is within the skill and judgement of the clinician.

For any compound, the therapeutically effective amount can be estimated initially either in in vitro assays, e.g. cell culture assays, or in animal models, e.g. mice, rats or dogs. The animal model may also be used to determine the appropriate concentration range and route of administration. Such information can then be used to determine useful doses and routes for administration in humans. Therapeutic efficacy and toxicity may be determined by standard procedures in cell cultures or experimental animals, e.g. ED50 and LD50 values can be determined and the ratio between toxic and therapeutic effects, also known as therapeutic index, may be calculated and used to determine suitable doses for use in humans.

As used herein, unless otherwise stated, the term "treating" and "treatment" in relation to a disease, disorder or condition refers to the management and care of a patient for the purpose of combating a disease, disorder or condition, such as to reverse, alleviate, or inhibit the process of the disease, disorder or condition to which such term applies, or one or more symptoms of such disease, disorder or condition, and includes the administration of a compound of the invention (or a pharmaceutically acceptable salt thereof) for alleviating the symptoms or complications. Preferably, treatment is ameliorating.

While it is possible that a compound of the invention may be administered for use in therapy directly as such, it is typically administered in the form of a pharmaceutical composition. These compositions comprise a compound of the invention (or a pharmaceutically acceptable salt thereof) as active pharmaceutical ingredient together with one or more pharmaceutically acceptable carriers. For the purposes of the invention, a carrier is suitable for use in the pharmaceutical compositions described herein if it is compatible with the other ingredients of the composition and not deleterious to the recipient of the composition. A “pharmaceutically acceptable carrier” includes non-API (API refers to Active Pharmaceutical Ingredient) substances, such as disintegrators, binders, fillers, lubricants and the like, used in formulating pharmaceutical products and regarded as safe for administering to subjects (particularly humans) according to established governmental standards, including those promulgated by the United States Food and Drug Administration and the European Medical Agency. Pharmaceutically acceptable carriers are well known to those skilled in the art and are selected on the basis of the chosen type of formulation and route of administration, according to standard pharmaceutical practice as described for example in *Remington: The Science and Practice of Pharmacy* 22nd edition, edited by Loyd V Allen Jr, Pharmaceutical Press, Philadelphia, 2012).

Accordingly, provided herein is a pharmaceutical composition comprising a compound of Formula (I) (including any of its subgenus of Formula (IIa), (IIb), (IIIa), (IIIb), (IVa), (IVa-1), (IVb) and (IVb-1), and any embodiments thereof as described herein), or a pharmaceutically acceptable salt thereof, and one or more pharmaceutically acceptable carriers.

Pharmaceutical compositions can be prepared in a manner well known in the pharmaceutical art, and can be administered by a variety of routes, for example via oral, parenteral, pulmonary or topical route. Parenteral administration includes intravenous, intraarterial, subcutaneous, intraperitoneal or intramuscular. Parenteral administration can be in the form of a single bolus dose, or may be, for example, by a continuous perfusion pump. Pulmonary administration includes e.g. by inhalation or insufflation of powders or aerosols, including by nebulizer. Topical administration includes transdermal, epidermal, ophthalmic and to mucous membranes including intranasal, vaginal and rectal delivery.

The compositions can be formulated as to provide quick (immediate), sustained or delayed release of the active ingredient after administration to the patient by using methods known in the art.

Examples of pharmaceutically acceptable excipients include lactose, dextrose, sucrose, sorbitol, mannitol, staches, gum acacia, calcium phosphate, alginates, tragacanth, gelatin, calcium silicate, microcrystalline cellulose, polyvinylpyrrolidone, cellulose, water, and methyl cellulose. The pharmaceutical compositions can additionally include further pharmaceutically acceptable excipients including: lubricating agents such as talc, magnesium stearate and mineral oil; wetting agents; emulsifying and suspending agents; preserving agents such as methyl- and propylhydroxybenzoates; sweetening agents; flavouring agents; and colouring agents.

Suitable oral dosage forms include, for examples, tablets, pills, sachets or capsules of hard or soft gelatin or any other suitable material. For example, the active compound can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, corn starch), and sweetening or flavoring agents (e.g., glucose, sucrose, saccharin, methyl salicylate, and peppermint). They can then be compressed into tablets or enclosed in capsules using conventional techniques. The capsules and tablets can also be coated with various coatings known in the art to modify the flavors, tastes, colors, and shapes of the capsules and tablets. In addition, liquid carriers such as fatty oil can also be included in capsules. Oral formulations can also be in the form of suspensions, solutions, syrups and the like. If desired, conventional agents for modifying flavors, tastes, color and the like can be added.

Pharmaceutical compositions suitable for parenteral administration include sterile aqueous solutions or suspensions, or can be alternatively prepared in lyophilized form for extemporaneous preparation of a solution or suspension using a sterile aqueous carrier prior to use. In such formulations, diluents or pharmaceutically acceptable carriers such as sterile water and physiological saline buffer can be used. Other conventional solvents, pH buffers, stabilizers, anti-bacterial agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Compositions for administration by inhalation or insufflation include solutions and suspensions in pharmaceutically acceptable aqueous or organic solvents, or mixtures thereof, and powders. The liquid or solid compostions may include suitable pharmaceutically acceptable excipients as described above. Such compositions may be administered by the oral or nasal respiratory route for local or systemic effect. Compositions can be nebulized by use of a suitable gas. Nebulized solutions may be breathed directly from the nebulizing device or the nebulizing device may be attached to a face mask or the breathing chamber. Solutions, suspensions and powder compositions can be administered orally or nasally from devices which deliver the formulation in an appropriate manner.

Pharmaceutical compositions for topical administration may include transdermal patches, ointments, lotions, creams, gels, drops, suppositories, sprays, liquids and powders. Topical formulations can contain one or more conventional carriers. For example, ointments can contain water and one or more hydrophobic carriers selected from liquid paraffin, polyoxyethylene alkyl ether, propylene glycol, white vaseline and the like. Carrier compositions of creams can be based on water in combination with glycerol and one or more other components such as cetylstearyl alcohol, glycerin monostearate and the like. Gels can be formulated using isopropyl alcohol and water, suitably in combination with other excipients such as glycerol, hydroxyethyl cellulose and the like.

The pharmaceutical compositions, like oral and parenteral compositions, can be formulated in unit dosage forms for ease of administration and uniformity of dosage. As used herein, “unit dosage forms” refers to physically discrete units suitable as unitary dosages for administration to subjects, each unit containing a predetermined quantity of active ingredient calculated to produce the desired therapeutic effect, in association with one or more suitable pharmaceutical carriers.

In therapeutic applications, pharmaceutical compositions are to be administered in a manner appropriate to the disease to be treated, as determined by a person skilled in the medical arts. An appropriate dose and suitable duration and frequency of administration will be determined by such factors as the condition of the patient, the type and severity of the disease, the particular form of the active ingredient, the method of administration, among others. In general, an appropriate dose and administration regimen provides the pharmaceutical composition in an amount sufficient to provide therapeutic benefit, for example an improved clinical outcome, such as more frequent complete or partial remissions, or longer disease-free and/or overall survival, or lessening of symptoms severity, or any other objectively identifiable improvement as noted by the clinical. Effective doses may generally be assessed or extrapolated using experimental models like dose-response curves derived from in vitro or animal model test systems.

The pharmaceutical compositions of the invention can be included in a container, pack or dispenser together with instructions for administration.

The compounds of the invention can be administered as a single active agent or may also be used or administered in combination with one or more additional therapeutically active agents, e.g. drugs useful in the treatment of a disease selected from cancers, autoimmune or inflammatory diseases, transplant rejection, ciliopathies, diseases of the nervous system, mental or behavioral disorders, infectious diseases, cardiovascular diseases, muscle atrophy and cachexia. Combination therapy includes administration of a single pharmaceutical dosage formulation which contains a compound of the invention and one or more additional therapeutically active agents, as well as administration of the compound of the invention and each additional therapeutically active agent in its own separate pharmaceutical dosage formulation for separate administration. If administered separately, the administration can be simultaneous, sequential or separate, and the compound of the invention and the additional therapeutic agent(s) can be administered via the same administration route or using different administration routes, for example one compound can be administered orally and the other intravenously. Moreover, as explained above, the compounds of the invention can also be used in monotherapy, particularly in the monotherapeutic treatment of a disease selected from cancer, an autoimmune or inflammatory disease, transplant rejection, a ciliopathy, a disease of the nervous system, a mental or behavioral disorder, an infectious disease, a cardiovascular disease, muscle atrophy, and cachexia.

EXAMPLES

The following abbreviations have been used in the examples:

AcN: acetonitrile
AcOH: acetic acid
aq: aqueous,
Boc: tert-butyloxycarbonyl
n-BuOH: n-butanol
DCM: Dichloromethane
DIAD: Diisopropyl azodicarboxylate
DIPEA: N,N-Diisopropylethylamine,
DMF: N,N-dimethylformamide
EtOAc: ethyl acetate
EtOH: ethanol
FA: Formic acid
HPLC: high performance liquid chromatography
LC-MS: liquid chromatography-mass spectroscopy
MeI: Iodomethane
MeOH: methanol
$PPh_3$: triphenylphosphine
$Pd(PPh_3)_4$: tetrakis(triphenylphosphine) palladium (0)
$Pd(PPh_3)_2Cl_2$: Bis(triphenylphosphine)palladium chloride
Pet ether: petroleum ether,
pTSA: p-Toluenesulfonic acid monohydrate
rt (or RT): room temperature
Rt: retention time,
TBAB: Tetrabutylammonium bromide
TEA: triethylamine
TFA: Trifluoroacetic acid
THF: tetrahydrofurane
THP: tetrahydropyran
$T_3P$: Propylphosphonic anhydride solution≥50 wt. % in ethyl acetate One of the following methods was used for the determination by LC-MS:

Method 1: Column: KINETEX-1.7u XB-C18 100A (50 mm×2.1 mm, 1.7 μm); Mobile Phase: A: 0.05% Formic Acid in Water B: 0.05% Formic Acid in Acetonitrile; Gradient: Time/% A: 0/97, 0.3/97, 3.2/2, 4.8/2, 5/97, 5.10/97 Column Temp: 35° C.; Flow Rate: 0.6 mL/min Method 2: Column: Aquity UPLC BEH C18 (50 mm×2.1 mm, 1.7 μm); Mobile Phase: B: 0.1% Formic Acid in Water A: 0.1% Formic Acid in Acetonitrile; Gradient: Time/% B: 0/97, 0.3/97, 3.2/2, 4/2, 4.01/97; Column Temp: 35° C.; Flow Rate: 0.6 mL/min;

Method 3: Column: Aquity UPLC BEH C18 (50 mm×2.1 mm, 1.7 μm); Mobile Phase: B: 0.1% Formic Acid in Water, A: 0.1% Formic Acid in Acetonitrile; Gradient: Time/% B: 0/97, 0.3/97, 3.0/2, 4.5/2, 4.51/97; Column Temp: 35° C.; Flow Rate: 0.6 mL/min.

Method 4: Column: Aquity UPLC BEH C18 (50 mm×2.1 mm, 1.7 μm); Mobile Phase: B: 0.1% Formic Acid in Water A: 0.1% Formic Acid in Acetonitrile; Gradient: Time/% B: 0/97, 0.3/97, 2.2/2, 3.30/2, 4.5/2, 4.51/97; Column Temp: 35° C.; Flow Rate: 0.6 mL/min;

Method 5: Column—AQUITY UPLC BEH C18 (50 mm×2.1 mm, 1.7 μm); Mobile Phase: A: 0.1% FA in Water, B: 0.1% FA in Acetonitrile: T % A of: 0/90, 1/10, 2.20/10, 2.30/90, 2.60/90 Flow-0.8 mL/min, Temp:50° C.

Method 6: Column—AQUITY UPLC BEH C18 (50 mm×2.1 mm, 1.7 μm); Mobile phase-A: 0.1% FA in Water, B: 0.1% FA in Acetonitrile T % A of: 0/95, 0.3/95, 2.0/5, 3.5/5, 3.6/95, 4.2/95 Flow-0.6 mL/min, Temp: 40° C.

Method 7: Column: Aquity UPLC BEH C18 (50 mm×2.1 mm, 1.7 □m); Mobile Phase: A: 0.05% Formic Acid in Acetonitrile, B: 0.05% Formic Acid in Water; Gradient: Time/% B: 0/97, 0.3/97, 3.2/2, 3.8/2, 4.3/97, 4.5/97; Column Temp: 35° C.; Flow Rate: 0.6 mL/min Method 8: Column: Aquity UPLC BEH C18 (50 mm×2.1 mm, 1.7 μm); Mobile Phase: A: 0.1% Formic Acid in water, B: 0.1% Formic Acid in Acetonitrile; Gradient: Time/% B: 0/97, 0.3/97, 2.7/2, 3.5/2, 3.51/97, Column Temp: 35° C.; Flow Rate: 0.6 mL/min;

Method 9: Column—AQUITY UPLC BEH C18 (50 mm×2.1 mm, 1.7 μm); Mobile phase-A: 0.1% FA in Water, B: 0.1% FA in Acetonitrile; T % A of: 0/97 0.3/97, 3.0/2, 4.0/2, 4.2/97, 4.50/97 Flow-0.6 mL/min, Temp: 35° C.

Method 10: Column: Aquity UPLC BEH C18 (50 mm×2.1 mm, 1.7 μm); Mobile Phase: A: 0.1% Formic Acid in Water, B: 0.1% Formic Acid in Acetonitrile; Gradient: Time/% A: 0/97, 0.3/97, 3.0/2, 4.0/2, 4.3/97, 4.50/97; Column Temp: 35° C.; Flow Rate: 0.6 mL/min Method 11: Column: Aquity UPLC BEH C18 (50 mm×2.1 mm, 1.7 μm); Mobile Phase: A: 0.1% Formic Acid in Water, B: 0.1% Formic Acid in Acetonitrile; Gradient: Time/% B: 0/5, 0.3/95, 2.0/95, 3.7/95, 4.2/5, 5.7/5; Column Temp: 40° C.; Flow Rate: 0.5 mL/min Method 12: Column—AQUITY UPLC BEH C18 (50 mm×2.1 mm, 1.7 μm); Mobile phase-A: 0.1% FA in Water, B: 0.1% FA in Acetonitrile; T % A of: 0/98 0.2/98, 1.8/2, 2.4/2, 2.60/98, 3.0/98. Flow-0.8 mL/min, Temp: 50°

Method 13: Column: YMC TRAIT C18; Mobile Phase: A: Acetonitrile, B: 0.01 M Ammonium Bicarbonate in Aq; Gradient: A=40%, B=60%. Flow Rate: 25.0 mL/min.

Method 14: Column: XBridge BEH C18 (50 mm×2.1 mm, 2.5 μm); Mobile Phase: A: 0.01 M Ammonium Formate in water; B: AcN; Gradient: Time/% B: 0/5, 3/100, 3.5/100, 3.8/5, 4.3/5; Flow Rate: 0.7 mL/min. Temp: 40° C.

Method 15: Column: XBridge BEH C18 (50 mm×3.0 mm, 2.5 μm); Mobile Phase: A: 0.01 M Ammonium Formate in water: AcN (95:5), B: 0.01 M Ammonium Formate in water:AcN (5:95); Gradient: Time/% B: 0/2, 4/98, 4.5/98, 5/2, 5.5/2, 6.5/2; Flow Rate: 1.0 mL/min Method 16: Column: XBridge BEH C18 (50 mm×3.0 mm, 2.5 μm); Mobile Phase: A: 0.01 M Ammonium Formate in water: AcN (95:5), B: 0.01 M Ammonium Formate in water:AcN (5:95); Gradient: Time/% B: 0/2, 2/2, 7/98, 7.5/98, 8.5/2, 10/2; Flow Rate: 1.0 mL/min;

Method 17: Column: Aquity UPLC BEH C18 (50 mm×2.1 mm, 1.7 μm); Mobile Phase: A: 0.01 M Ammonium Bicarbonate in Water, B: Acetonitrile; Gradient: Time/% B: 0/3; 1.0/3; 7.0/100; 7.5/100; 9.0/3; 10.0/3.Column Temp: 35° C.; Flow Rate: 0.5 mL/min;

Method 18: Column: XBridge BEH C18 (50 mm×2.10 mm, 2.5 μm); Mobile Phase: A: 0.01 M Ammonium Formate in water: AcN (95:5), B: Acetonitrile; Gradient: Time/% B: 0/5; 1.0/5; 7/100; 7.5/100; 9/5, 10/5 Column Temp: 40° C.; Flow Rate: 0.7 mL/min;

Method 19: Column: XBridge BEH C18 (50 mm×3.0 mm, 2.5 μm); Mobile Phase A: 0.01 M Ammonium Formate in water: AcN (95:5), B: 0.01 M Ammonium Formate in water:AcN (5:95); Gradient: Time/% B: 0/2, 1/2, 4/98, 4.5/98, 5.5/2, 6.5/2; Flow Rate: 1.0 mL/min;

Method 20: Column: Aquity UPLC BEH C18 (50 mm×2.1 mm, 1.7 μm); Mobile Phase: A: 0.1% Formic Acid in Water, B: 0.1% Formic Acid in Acetonitrile; Gradient: Time/% A: 0/97, 1.0/97, 7.0/0, 7.5/0, 9.0/97; Column Temp: 35° C.; Flow Rate: 0.5 mL/min Method 21: Column: Aquity UPLC BEH C18 (50 mm×2.1 mm, 1.7 μm); Mobile Phase: A: 0.1% Formic Acid in Water, B: 0.1% Formic Acid in Acetonitrile; Gradient: Time/% A: 0/5, 0.1/5, 2.7/100, 3.5/100, 3.8/5; 4.3/5 Column Temp: 40° C.; Flow Rate: 0.7 mL/min Method 22: Column: XBridge BEH C18 (50 mm×2.1 mm, 2.5 μm); Mobile Phase A: 0.01 M Ammonium Formate in water: AcN (95:5), B: 0.01 M Ammonium Formate in water:AcN (5:95); Gradient: Time/% B: 0/2, 1/2, 7/100, 7.5/100, 9/2, 10/2; Flow Rate: 0.7 mL/min;

Method 23: Column: Aquity UPLC BEH C18 (50 mm×2.1 mm, 2.5 μm); Mobile Phase A: 0.01 M Ammonium Acetate in water; B: AcN; Gradient: Time/% B: 0/5, 0.2/5, 7/100, 8/100, 8.5/5, 11/5; Column Temp: 40° C.; Flow Rate: 0.5 mL/min;

Method 24: Column: Luna Omega 3 μm PS C18 100A; Mobile Phase A: 0.01 M Ammonium Formate in water: AcN (95:5); B: 0.01 M Ammonium Formate in water: AcN (5:95); Gradient: Time/% B: 0/2, 1/2, 4/98, 4.5/98, 5.5/2, 6.5/2; Flow Rate: 1.0 mL/min;

Method 25: Column—AQUITY UPLC BEH C18 (50 mm×2.1 mm, 1.7 μm); Mobile phase-A: 0.1% FA in Water, B: 0.1% FA in Acetonitrile T % A of: 0/95, 0.3/95, 2.0/5, 3.5/5, 3.6/95, 4.4/95 Flow-0.6 mL/min, Temp: 40° C.

Method 26: Column: Aquity UPLC BEH C18 (50 mm×2.1 mm, 1.7 μm); Mobile Phase A: 0.01 M Ammonium Acetate in water; B: AcN; Gradient: Time/% A: 0/5, 0.1/5, 2.4/100, 3.8/100, 4.0/5; 4.5/5 Column Temp: 50° C.; Flow Rate: 0.5 mL/min Method 27: Column: Luna Omega 3 μm PS C18 100A); Mobile Phase A: 0.01 M Ammonium Formate in water: AcN (95:5), B: 0.01 M Ammonium Formate in water: AcN (5:95); Gradient: Time/% B: 0/2, 1/2, 7/100, 7.5/100, 9/2, 10/2; Flow Rate: 1.0 mL/min.

Reference Example 1

2-(Trimethylstannyl)isonicotinonitrile

To a stirred solution of 2-bromoisoniconitrile (2 g, 10.92 mmol) in toluene (20 mL), hexamethylditin (4.6 g, 14.20 mmol), and $Pd(PPh_3)_4$ (1.2 g, 1.09 mmol) were added at rt. The resulting solution was degassed with nitrogen for 10 min and heated to 110° C. for 16 h. The reaction mixture was evaporated under reduced pressure and the crude compound was purified by flash column chromatography on neutral alumina using 50% EtOAc in petroleum ether to afford the title compound (1.5 g, 51.7%).

LC-MS (method 1): Rt=1.93 min; m/z=269.08 ($M+H^+$)

Reference Example 2

5-Bromo-1-butyl-1H-pyrrolo[2,3-c]pyridine

To a stirred suspension of 60% NaH (0.146 g, 6.091 mmol) in DMF (20 mL), 5-bromo-1H-pyrrolo[2,3-c]pyridine (0.8 g, 4.06 mmol) was added at °0 C and stirred for 15 min. Then, 1-bromo butane (0.66 g, 4.873 mmol) was added to the reaction mixture at °0 C The resulting mixture was allowed to warm to rt and stirred for 16 h. The reaction mixture was quenched with water and extracted EtOAc and the organic layer was dried over anhydrous $Na_2SO_4$, and it was concentrated under reduced pressure. The crude compound was purified by flash column chromatography using 10% EtOAc in pet ether as an eluent to afford the title compound (0.78 g, 67%).

LC-MS (method 2): $R_t$=2.27 min; m/z=253.17 ($M+H^+$).

Following a similar procedure to that described in reference example 2, but using in each case the corresponding starting materials, the following compounds were obtained:

| Reference example | Compound name | Starting material | HPLC method | $R_t$ (min) | m/z |
|---|---|---|---|---|---|
| 2a | 5-Bromo-1-propyl-1H-pyrrolo[2,3-c]pyridine | 1-Iodopropane | 3 | 2.23 | 239.06 $(M + H^+)$ |
| 2b | 5-Bromo-1-(2-methoxyethyl)-1H-pyrrolo[2,3-c]pyridine (*) | 1-Bromo-2-methoxy ethane | 15 | 3.30 | 255.21 $(M + H^+)$ |

(*) 0.02 eq of NaI were added.

Reference Example 3

5-Bromo-1-butyl-N,N-dimethyl-1H-pyrrolo[2,3-c]pyridine-2-carboxamide

Step a. 5-Bromo-N,N-dimethyl-1H-pyrrolo[2,3-c]pyridine-2-carboxamide

To a stirred solution of 5-bromo-1H-pyrrolo[2,3-c]pyridine-2-carboxylic acid (500 mg, 2.07 mmol) in DMF, dimethyl amine hydrochloride (168 mg, 2.07 mmol), TEA (1.49 g, 10.37 mmol) and $T_3P$ (1.97 g, 6.21 mmol) were added at 0° C. The resulting mixture was allowed to stir at rt for 16 h. The reaction mixture was diluted with water and extracted with EtOAc. The combined organic layers were dried over anhydrous $Na_2SO_4$, filtered and concentrated under reduced pressure. The crude compound was purified by silica gel column chromatography and eluted at 5% MeOH in DCM to afford the title compound (450 mg, 78%).

LC-MS (method 4): $R_t$=1.75 min; m/z=270.15 $(M+H^++2)$.

Step b. 5-Bromo-1-butyl-N,N-dimethyl-1H-pyrrolo[2,3-c]pyridine-2-carboxamide To a stirred solution of the compound obtained in the previous section, step a (1.4 g, 5.24 mmol) in DMF, 60% NaH (1.04 g, 26.21 mmol) was added at 0° C. The reaction mixture was stirred for 15 minutes at the same temperature and then butyl iodide (1.92 g, 10.48 mmol) was added. The suspension was stirred at rt for 16 h. The reaction mixture was cooled at 0° C., quenched with water and extracted with EtOAc. The separated organic layer was dried over anhydrous $Na_2SO_4$, filtered and concentrated under reduced pressure. The crude compound was purified by silica gel column chromatography and eluted at 5% MeOH in DCM to afford the title compound (1.0 g, 59.8%)

LC-MS (method 5): $R_t$=1.10 min; m/z=325.36 $(M+H^+)$.

Following a similar procedure to that described in reference example 3, but using in each case the corresponding starting material, the following compounds were obtained:

| Reference example | Compound name | Starting material | HPLC method | $R_t$ (min) | m/z |
|---|---|---|---|---|---|
| 3a | 5-Bromo-N,N,1-trimethyl-1H-pyrrolo[2,3-c]pyridine-2-carboxamide | Dimethyl amine hydrochloride (step a) and iodomethane (step b) | 6 | 1.62 | 282.10 $(M + H^+)$ |
| 3b | 5-Bromo-1-butyl-N-ethyl-1H-pyrrolo[2,3-c]pyridine-2-carboxamide | Ethyl amine hydrochloride (step a) and butyl iodide (step b) | 6 | 2.12 | 322.21 $(M - H^+)$ |
| 3c | 5-Bromo-1-butyl-N,N-diethyl-1H-pyrrolo[2,3-c]pyridine-2-carboxamide | Diethyl amine hydrochloride (step a) and butyl iodide (step b) | 6 | 2.26 | 352.28 $(M + H^+)$ |

Reference Example 4

3-((6-Bromopyridin-3-yl)oxy)-N,N-diethylpropan-1-amine

To a stirred solution of 6-bromopyridin-3-ol (5.0 g, 28.73 mmol) in THF (50 mL), $PPh_3$ (15.0 g, 57.47 mmol), DIAD (8.7 g, 43.10 mmol) and 3-(diethylamino)propan-1-ol (5.64 g, 43.10 mmol) were added at 0° C. The reaction mixture was allowed to stir at rt for 16 h. The reaction mixture was diluted with water (100 mL) and extracted with EtOAc (2×100 mL). The combined organic layer was dried over anhydrous $Na_2SO_4$, filtered and the filtrate was concentrated. The crude compound was purified by flash column chromatography using 100-200 silica gel and eluted with 40% EtOAc/pet ether to afford the title compound (3.1 g, 38%) as a gummy liquid.

LC-MS (method 7): $R_t$=1.50 min; m/z=287.18 $(M+H^+)$.

Reference Example 5

1-(5-Bromo-1-butyl-1H-pyrrolo[2,3-c]pyridin-3-yl)-N,N-dimethylmethanamine

To a stirred solution of reference example 2 (500 mg, 1.97 mmol) in n-BuOH (20 mL), 37% formaldehyde aqueous solution (37%) (0.78 mL, 9.88 mmol), and dimethyl amine hydrochloride (805 mg, 9.88 mmol) were added. The reaction mixture was stirred at 120° C. for 16 h and then it was cooled to rt. The organic solvent was evaporated under reduced pressure to get a residue that was diluted with 1N NaOH aqueous solution and extracted with 10% MeOH/DCM (2×50 mL). The crude residue was evaporated to get a crude compound that was purified by column chromatography on 230-400 silica with 85% EtOAc/pet ether along with 0.5 mL of TEA to afford 400 mg (65%) of the title compound as a gummy solid.

LC-MS (method 5): $R_t$=0.77 min; m/z=312.12 $(M+H^++2)$.

Following a similar procedure to that described in reference example 5, but using in each case the corresponding starting materials, the following compounds were obtained:

| Reference example | Compound name | Starting material | HPLC method | $R_t$ (min) | m/z |
|---|---|---|---|---|---|
| 5a | 5-Bromo-3-(piperidin-1-ylmethyl)-1-propyl-1H-pyrrolo[2,3-c]pyridine | Piperidine and reference example 2a | 6 | 1.46 | 336.24 (M + $H^+$) |
| 5b | 4-((5-Bromo-1-propyl-1H-pyrrolo[2,3-c]pyridin-3-yl)methyl)morpholine | Morpholine and reference example 2a | 6 | 1.35 | 338.21 (M + $H^+$) |
| 5c | 1-(5-Bromo-1-propyl-1H-pyrrolo[2,3-c]pyridin-3-yl)-N,N-dimethylmethanamine | Dimethyl amine hydrochloride and reference example 2a | 6 | 1.33 | 296.20 (M + $H^+$) |

Reference Example 6

2-Bromo-5-(3-(4,4-difluoropiperidin-1-yl)propoxy) pyridine

Step a. 2-Bromo-5-(3-chloropropoxy)pyridine

To a stirred solution of 6-bromopyridin-3-ol (3 g, 17.2 mmol) in DMF (50 mL), $K_2CO_3$ (7.1 g, 51.6 mmol) was added and stirred at rt for 15 minutes. It was cooled to 0° C. and 1-bromo-3-chloropropane (4 g, 25.8 mmol) was added. The resulting mixture was stirred at rt for 16 h. The reaction mixture was diluted with ice cold water and extracted with EtOAc (3×100 mL), washed with water (2×80 mL) and then brine (50 mL). The organic layer was dried over anhydrous $Na_2SO_4$, filtered and concentrated under reduced pressure to afford the title compound (2.8 g, 64%) as a yellow gummy liquid.

LC-MS (method 6): $R_t$=2.04 min; m/z=250.01 (M+$H^+$).

Step b. 2-Bromo-5-(3-(4,4-difluoropiperidin-1-yl) propoxy)pyridine

To a solution of the compound obtained in the previous section, step a (2 g, 7.98 mmol) in acetonitrile, 4,4-difluoropiperidine hydrochloride (1.88 g, 11.97 mmol), $K_2CO_3$ (3.3 g, 23.95 mmol), and NaI (1.19 g, 7.98 mmol) were added at rt. The resulting mixture was stirred at 70° C. for 24 h and then it was cooled to rt. The reaction mixture was poured into ice water (30 mL) and extracted with EtOAc (2×80 mL): The organic layer was dried over anhydrous $Na_2SO_4$, filtered and concentrated under reduced pressure. The crude residue was washed with n-pentane and dried to afford 1.5 g (56%) of the title compound as a gummy liquid.

LC-MS (method 5): $R_t$=0.66 min; m/z=335.15 (M+$H^+$).

Following a similar procedure to that described in reference example 6, but using the corresponding starting material, the following compound was obtained:

| Reference example | Compound name | Starting material | HPLC method | $R_t$ (min) | m/z |
|---|---|---|---|---|---|
| 6a | 4-(3-((6-Bromopyridin-3-yl)oxy)propyl)morpholine | Morpholine | 6 | 1.17 | 301.11 (M + $H^+$) |
| 6b | 3-(6-Bromopyridin-3-yloxy)-N,N-dimethylpropan-1-amine | Demethyl amine hydrochloride | 15 | 1.77 | 259.34 (M + $H^+$) |
| 6c | 2-((3-((6-Bromopyridin-3-yl)oxy)propyl)(methyl)amino)ethan-1-ol | 2-(Methylamino) ethanol | 14 | 1.43 | 289.0 (M + $H^+$) |

Reference Example 7

N-(6-Bromopyridin-3-yl)-N-butyl-3-methoxypropanamide

Step a. 6-Bromo-N-butylpyridin-3-amine (2) (C2134-130)

To a stirred solution of 6-bromopyridin-3-amine (10 g, 57 mmol) in MeOH (100 mL), butyraldehyde (4.9 g, 69.36 mmol) was added and stirred for 16 h at rt. It was cooled to 0° C. and $NaBH_3CN$ (7.2 g, 115.6 mmol) was added. The resulting mixture was stirred at rt for 16 h. The reaction mixture was poured into cold water (100 mL), extracted with EtOAc (2×200 mL) and washed with brine solution (150 mL). The organic layers were dried over anhydrous $Na_2SO_4$, filtered and concentrated under reduced pressure to get a crude compound that was purified by column chromatography with 13% EtOAc/pet-ether to afford 7 g (52%) of the title compound.

LC-MS (method 4): $R_t$=2.31 min; m/z=229.16 (M+$H^+$).

Step b. N-(6-Bromopyridin-3-yl)-N-butyl-3-methoxypropanamide

To a stirred solution of the compound obtained in the previous section, step a (1500 mg, 6.54 mmol, 1.0 equiv) in DCM, 3-methoxypropanoic acid (1020 mg, 9.84 mmol), TEA (3.30 g, 32.75 mmolv) and $T_3P$ (8.3 g, 26.18 mmol) were added at 0° C. The reaction mixture was allowed to stir at rt for 16 h. The reaction mixture was diluted with water and extracted with EtOAc. The combined organic layers were dried over anhydrous $Na_2SO_4$, filtered and concentrated under reduced pressure. The crude compound was purified by silica gel column chromatography and eluted at 30% EtOAc in pet ether to afford (1450 mg, 70%) of the title compound.

LC-MS (method 10): $R_t$=2.40 min; m/z=315.12 (M+$H^+$).

Reference Example 8

6-Bromo-N-(cyclopropylmethyl)-N-methylpyridin-3-amine

To a stirred solution of 6-bromo-N-methylpyridin-3-amine (1200 mg, 6.44 mmol) in DMF, 60% NaH (1030 mg, 25.76 mmol) was added at 0° C. and stirred at rt for 15 minutes. It was cooled at 0° C., and (bromomethyl)cyclopropane (1738 mg, 12.88 mmol) was added. It was allowed to stir at rt for 1 h. The reaction mixture was cooled to 0° C., quenched with water and extracted with EtOAc. The separated organic layer was washed with water and brine solution and dried over anhydrous $Na_2SO_4$, filtered and concentrated under reduced pressure. The crude compound was purified by column chromatography and eluted at 15% EtOAc in pet ether to afford the title compound (1.0 g, 64.2%) as a yellow gummy;

LC-MS (method 5): $R_t$=1.20 min; m/z=240.97 (M+$H^+$).

Reference Example 9

Tert-butyl (6-bromopyridin-3-yl)(3-(diethylamino)propyl)carbamate

Step a. 3-Chloro-N,N-diethylpropan-1-amine hydrochloride

To a stirred solution 3-(diethylamino)propan-1-ol (1 g, 7.63 mmol) in DCM (10 mL) was added $SOCl_2$ (1.1 mL, 15.26 mmol) at 0° C. and the resulting mixture was stirred at rt for 3 h. The reaction was concentrated under reduced pressure to afford the title compound (1 g, 88%).

Step b. Tert-butyl (6-bromopyridin-3-yl)(3-(diethylamino)propyl)carbamate

To a stirred suspension of 60% NaH (0.15 g, 6.598 mmol) in DMF (50 mL), a solution of tert-butyl (6-bromopyridin-3-yl)carbamate (1.2 g, 4.399 mmol) in DMF (10 mL) at 0° C. was added. The resulting mixture was stirred for 15 min, and then the compound obtained in the previous section, step a, was added (0.785 g, 5.274 mmol) to the reaction mixture at 0° C. The resulting mixture was stirred at rt for 16 h. The reaction mixture was quenched with ice cold water and extracted with EtOAc. The organic layer was concentrated under reduced pressure and the obtained crude compound was purified by flash column chromatography using 100% EtOAc as an eluent to obtain the title compound (0.9 g, 53)

LC-MS (method 13): $R_t$=1.55 min; m/z=388.09 (M+$H^+$+2).

Reference Example 10

6-Bromo-N-(3-(4,4-difluoropiperidin-1-yl)propyl)-N-methylpyridin-3-amine

Step a. Tert-butyl (6-bromopyridin-3-yl)(3-chloropropyl)carbamate

To a stirred solution of tert-butyl 6-bromopyridin-3-ylcarbamate (2.0 g, 7.352 mmol) in DMF (20 mL), 60% NaH (0.529 g, 22.05 mmol) was added at 0° C. and stirred at rt for 15 minutes. Then, 1-bromo-3-chloropropane (2.308 g, 14.705 mmol) was added and the resulting mixture was allowed to stir at rt for 16 h. The reaction mixture was cooled to 0° C., quenched with ice-water and extracted with EtOAc. The organic layers were washed with water and brine solution, dried over anhydrous $Na_2SO_4$, filtered and concentrated under reduced pressure. The crude compound was purified by silica gel column chromatography and eluted at 8% EtOAc in pet ether to afford the title compound (2.0 g, LCMS-75%) as a brown colour gummy;

LC-MS (method 5): $R_t$=1.31 min; m/z=349.20 (M+$H^+$).

Step b Tert-butyl (6-bromopyridin-3-yl)(3-(4,4-difluoropiperidin-1-yl)propyl)carbamate To a stirred solution of 4,4-difluoropiperidine hydrochloride (1.815 g, 11.49 mmol) in AcN (30 mL), NaI (1.027 g, 6.896 mmol) and $K_2CO_3$ (2.379 g, 17.24 mmol) were added. The reaction mixture was stirred for 10 minutes, the compound obtained in the previous section, step a (2.0 g, 5.747 mmol) was added and heated to 90° C. for 16 h. The reaction mixture was filtered through a celite pad and it was washed with 10% MeOH in DCM. The filtrated solution was concentrated under reduced pressure and the crude compound was purified by silica gel column chromatography using 25% EtOAc in pet ether as eluent to afford the title compound (1.1 g, 44%) as an off-white solid;

LC-MS (method 5): $R_t$=0.86 min; m/z=434.35 (M+$H^+$).

Step c. 6-Bromo-N-(3-(4,4-difluoropiperidin-1-yl)propyl)pyridin-3-amine

To a stirred solution of the compound obtained in the previous section, step b (1.4 g, 3.22 mmol) in DCM (10 mL), TFA (3.0 ml) was added at 0° C. and it was allowed to stir at rt for 3 h. The reaction mixture was concentrated under reduced pressure. The crude residue was diluted with water, basified to pH-8 using saturated $NaHCO_3$ aqueous solution and extracted with EtOAc. The organic layers were washed with water and brine solution. The organic layers were dried over anhydrous $Na_2SO_4$, filtered and concentrated under reduced pressure to afford the title compound (1.01 g, 94%) as an off white solid;

LC-MS (method 6): $R_t$=1.40 min; m/z=334.11 (M+$H^+$).

Step d. 6-Bromo-N-(3-(4,4-difluoropiperidin-1-yl)propyl)-N-methylpyridin-3-amine To a stirred solution of the compound obtained in the previous section, step c, (3.0 g, 9.0 mmol) in formic acid (40 mL), paraformaldehyde (2.70 g, 90.09 mmol) was added and heated at 100° C. for 16 h. The reaction mixture was concentrated under reduced pressure: The crude residue was dissolved in water and basified to pH-8 using saturated $NaHCO_3$ aqueous solution and extracted with EtOAc (3×50 mL). The separated organic layers were dried over anhydrous $Na_2SO_4$, filtered and concentrated under reduced pressure The crude compound was purified by silica gel column chromatography and eluted at 20% EtOAc in pet ether to afford the title compound (2.5 g, 79%) as an off-white solid.

LC-MS (method 6): $R_t$=1.55 min; m/z=348.13 (M+$H^+$).

Reference Example 11

3-(2-Bromopyrimidin-5-yloxy)-N,N-diethylpropan-1-amine

Step a. 2-Bromopyrimidin-5-ol

To a stirred solution of 2-chloropyrimidin-5-ol (2 g, 15.3 mmol) in AcOH (6 mL), HBr (47% aqueous solution) (6 mL) was added at 0° C. and it was stirred at rt for 15 minutes. The resulting mixture was stirred at 100° C. for 24 h. The solvents were evaporated under vacuum and then poured into ice cold water and extracted with EtOAc (2×100 mL). The organic layer was dried over anhydrous $Na_2SO_4$, filtered and concentrated under reduced pressure to get a crude residue that was purified by column chromatography on 100-200 silica with 30% of EtOAc/pet ether to afford the title compound (1.5 g, 55%) as an off white solid.

LC-MS (method 6): $R_t$=0.94 min; m/z=175.03 (M+$H^+$).

Step b. 2-Bromo-5-(3-chloropropoxy)pyrimidine

To a stirred solution of the compound obtained in the previous section, step a (1.5 g, 8.6 mmol) in DMF, $K_2CO_3$ (3.5 g, 25.8 mmol) and 1-bromo-3-chloropropane (2) (2 g, 12.9 mmol) were added. The resulting mixture was stirred at rt overnight. The reaction mixture was diluted with water, extracted with EtOAc (2×100 mL). The organic layer was dried over $Na_2SO_4$, and evaporated under reduced pressure to afford 1.8 g (83%) of a crude compound that was used for the next step without any further purification.

LC-MS (method 6): $R_t$=1.89 min; m/z=251.08 (M+$H^+$).

Step c. 3-(2-Bromopyrimidin-5-yloxy)-N,N-diethyl-propan-1-amine

To a stirred solution of the compound obtained in the previous section, step b (1.8 g, 7.2 mmol) in AcN, $K_2CO_3$ (2.9 g, 21.6 mmol) and NaI (1.07 g, 7.2 mmol) were added. The resulting mixture was stirred at rt for 15 minutes and diethyl amine hydrochloride (2.6 g, 36 mmol) was added at rt. It was stirred at 70° C. for 16 h. The reaction mixture was diluted with ice cold water and extracted with EtOAc (3×100 mL). The organic layer was dried over anhydrous $Na_2SO_4$, filtered and concentrated under reduced pressure to afford the title compound (1.2 g, 58%) as a brown gummy liquid.

LC-MS (method 6): $R_t$=1.08 min; m/z=288.18 (M+$H^+$).

Reference Example 12

$N^1$-(6-Bromopyridin-3-yl)-$N^3$,$N^3$-diethyl-$N^1$-methylpropane-1,3-diamine

Step a. $N^7$-(6-Bromopyridin-3-yl)-$N^3$,$N^3$-diethylpropane-1,3-diamine

To a stirred solution of reference example 9 (1.2 g, 3.1 mmol) in DCM (20 ml), TFA (3.5 ml) was added and allowed to stir at rt for 8 h. The reaction mixture was concentrated to dryness to get a crude residue that was purified by column chromatography and eluted at 10% MeOH/DCM to afford 0.9 g (100%) of the title compound.

LC-MS (method 6): $R_t$=1.27 min; m/z=286.13 (M+$H^+$).

Step b. $N^1$-(6-Bromopyridin-3-yl)-$N^3$,$N^3$-diethyl-$N^1$-methylpropane-1,3-diamine To a stirred solution of the compound obtained in the previous section, step a (800 mg, 2.795 mmol) in formic acid (10 mL), paraformaldehyde (839 mg, 27.95 mmol) at 0° C. was added slowly and allowed to stir at 95° C. for 16 h. The reaction mixture was concentrated under reduced pressure and the residue was dissolved in water. The aqueous layer was basified using saturated NaOH aqueous solution, and concentrated under reduced pressure. The obtained crude residue was purified by column chromatography and eluted at 10% MeOH/DCM to afford the title compound (700 mg, 67.3%).

LC-MS (method 6): $R_t$=1.37 min; m/z=300.16 (M+$H^+$).

Reference 13

3-(6-Bromopyridin-3-yloxy)-N-methylpropan-1-amine

In a sealed tube, to a stirred solution of the compound obtained in reference example 6, step a (1 g, 4 mmol) in AcN, $K_2CO_3$ (1.6 g, 12 mmol) and NaI (300 mg, 2 mmol) were added at 0° C. and stirred at rt for 15 minutes. Then, a solution of 33% methylamine in EtOH, (0.6 mL, 6 mmol) was added at 0° C. The resulting mixture was stirred at 60° C. for 16 h. It was diluted with ice cold water and extracted with EtOAc. The organic layer was dried over anhydrous $Na_2SO_4$, filtered and concentrated under reduced pressure to get a crude residue that was purified by column chromatography on 230-400 silica with 2% MeOH/DCM as eluent to afford the title compound (750 mg, 76%) as a gummy liquid.

LC-MS (method 14): $R_t$=1.07 min; m/z=245.01 (M+$H^+$).

Reference 14

6-Bromo-1-(tetrahydro-2H-pyran-4-yl)-1H-pyrrolo[3,2-c]pyridine

To a stirred solution of 6-bromo-1H-pyrrolo[3,2-c]pyridine (1 g, 3.36 mmol) in DMF (20 mL), tetrahydro-2H-pyran-4-yl methanesulfonate (1.51 g, 8.38 mmol), and $Cs_2CO_3$ (5.46 g, 16.8 mmol) were added at 0° C. The resulting mixture was stirred at 100° C. for 16 h. The reaction mixture was diluted with EtOAc and washed with water. The organic layer was dried over anhydrous $Na_2SO_4$, filtered and concentrate under reduced pressure. The crude residue was purified by column chromatography and eluted at 10% MeOH in DCM to afford the title compound (0.33 g, 35%) as an off white solid.

LC-MS (method 6): $R_t$=1.73 min; m/z=281.07 (M+$H^+$).

Following a similar procedure to that described in reference example 14, but using in the corresponding starting material, the following compound was obtained:

| Reference example | Compound name | Starting material | HPLC method | $R_t$ (min) | m/z |
|---|---|---|---|---|---|
| 14a | 6-Bromo-1-((tetrahydro-2H-pyran-4-yl)methyl)-1H-pyrrolo[3,2-c]pyridine | (Tetrahydro-2H-pyran-4-yl)methyl methanesulfonate | 14 | 2.05 | 295.0 (M + H+) |

Reference Example 15

3-((6-Bromopyridin-3-yl)oxy)-N-ethyl-N-phenethyl-propan-1-amine

Step a. 3-((6-Bromopyridin-3-yl)oxy)propan-1-ol

To a stirred suspension of 6-bromopyridin-3-ol (5.0, 28.73 mmol) in DMF (40 mL), $K_2CO_3$ (11.90 g, 86.20 mmol) and 3-bromopropanol (4.39 g, 31.60 mmol) were added at rt and stirred for 16 h. The reaction mixture was quenched with ice cold water (150 mL) and extracted with ethyl acetate (2×60 mL). The combined organic layers were washed with water (100 mL) followed by brine solution (100 mL) and dried over anhydrous $Na_2SO_4$ and filtered. The solution filtrated was concentrated under reduced pressure and the resulting crude compound was purified by flash column chromatography using 30% of ethyl acetate in pet ether as the eluent to afford the title compound (3.50 g, 53%) as color less liquid.

LC-MS (method 5): $R_t$=0.82 min; m/z=232.05 (M+H$^+$).

Step b. 2-Bromo-5-(3-bromopropoxy)pyridine

To a solution of the compound obtained in the previous section, step a, (3.50 g, 15.08 mmol) in DCM (50 mL), $PPh_3$ (11.0 g, 30.17 mmol) and $CBr_4$ (9.98 g, 30.17 mmol) were added at 0° C. The resulting mixture was stirred at room temperature for 6 h. The solvent was removed under reduced pressure and the crude residue was purified by silica gel column using 10% EtOAc in pet ether as an eluent to afford the title compound (2.50 g, 56%) as color less liquid.

LC-MS (method 5): $R_t$=1.19 min; m/z=293.99 (M+H$^-$).

Step c. 3-((6-Bromopyridin-3-yl)oxy)-N-phenethyl-propan-1-amine

To a solution of the compound obtained in the previous section, step b, (2.50 g, 8.47 mmol) and 2-phenylethanamine (1.54 g, 12.71 mmol) in AcN (50 mL), NaI (1.27 g, 8.47 mmol) and $K_2CO_3$ (3.50 g, 25.42 mmol) were added. The resulting mixture was heated at 60° C. for 16 h. The reaction mixture was tempered, filtered and the filtrate was concentrated under reduced pressure: The crude residue was purified by grace reverse phase column chromatography using 35% AcN in 0.1% aq formic acid as eluent to afford the title compound (1.50 g, 53%) as color less liquid.

LC-MS (method 5): $R_t$=0.81 min; m/z=335.20 (M+H$^+$).

Step d. 3-((6-Bromopyridin-3-yl)oxy)-N-ethyl-N-phenethylpropan-1-amine

To a solution of the compound obtained in the previous section, step c, (1.50 g, 4.47 mmol) in DMF (20 mL), $K_2CO_3$ (1.85 g, 13.43 mmol) and ethyl iodide (1.04 g, 6.71 mmol) were added and stirred at room temperature for 16 h. The reaction mixture was quenched with ice cold water (150 mL) and extracted with ethyl acetate (2×60 mL). The combined organic layers were washed with water (100 mL) followed by brine solution (100 mL) and dried over anhydrous $Na_2SO_4$ and filtered. The solution filtrated was concentrated under reduced pressure and the resulting crude compound was purified by grace reverse phase column using 40% of Acetonitrile in 0.1% aq. Formic acid an eluent to afford the title compound (1.10 g, 68%) as color less liquid.

LC-MS (method 6): $R_t$=1.62 min; m/z=363.29 (M+H$^+$).

Reference Example 16

N-(6-Bromopyridin-3-yl)-2-phenylacetamide

To a stirred solution of 6-bromopyridin-3-amine (2.0 g, 11.56 mmol) in DCM (50 mL), 2-phenylacetic acid (2.04 g, 15.02 mmol), and TEA (4.60 g, 46.24 mmol) were added, followed by the addition of $T_3P$ (9.19 g, 28.90 mmol) at 0° C. The resulting mixture was stirred at rt for 16 h. The reaction mixture was washed with saturated $NaHCO_3$ aqueous solution (100 mL). The organic layer was dried over anhydrous $Na_2SO_4$ and filtered. The filtered solution was concentrated under reduced pressure and the resulting crude compound was purified by flash column chromatography using 25% ethyl acetate in pet ether as eluent to afford the title compound (2.30 g, 68%) as an off-white solid.

LC-MS (method 1): $R_t$=2.46 min; m/z=291.08 (M+H$^+$).

Following a similar procedure to that described in reference example 16, but using in each case the corresponding starting material, the following compound were obtained:

| Reference example | Compound name | Starting material | HPLC method | $R_t$ (min) | m/z |
|---|---|---|---|---|---|
| 16a | N-(6-Bromopyridin-3-yl)-1-methylpiperidine-4-carboxamide | 1-Methylpiperidine-4-carboxylic acid and 6-bromopyridin-3-amine | 2 | 1.04 | 300.15 (M + H+) |
| 16b | N-(2-Bromopyridin-4-yl)-2-cyclobutylacetamide | 2-Cyclobutylacetic acid and 6-bromopyridin-4-amine | 6 | 1.99 | 269.10 (M + H+) |
| 16c | Tert-butyl 3-(2-bromoisonicotinamido)piperidine-1-carboxylate (*) | 2-Bromoisonicotinic acid and tert-butyl 3-aminopiperidine-1-carboxylate | 6 | 2.18 | 384.29 (M + H+) |
| 16d | 2-Bromo-N-((1-methylpiperidin-4-yl)methyl)isonicotinamide | 2-Bromoisonicotinic acid I and (1-methylpiperidin-4-yl)methanamine | 6 | 1.28 | 312.25 (M + H+) |
| 16e | 6-Bromo-N-((1-methylpiperidin-4-yl)methyl)nicotinamide (**) | 6-Bromonicotinic acid and (1-methylpiperidin-4-yl)methanamine | 19 | 1.89 | 312.33 (M + H+) |

(*) using THF instead of DCM.
(**) using DMF instead of DCM

Reference Example 17

2-Bromo-4-(2-(4,4-difluoropiperidin-1-yl)ethoxy) pyridine

Step a. 2-((2-Bromopyridin-4-yl)oxy)ethan-1-ol

To a stirred solution of 2-bromopyridin-4-ol (2.0 g, 11.5 mmol) in DMF, $K_2CO_3$ (3.96 g, 28.75 mmol) was added at rt. 2-Bromoethanol (2.15 g, 17.25 mmol) was added slowly at 0° C. Then it was stirred at 70° C. for 12 h. The reaction mixture was quenched with ice cold water and extracted with DCM. The organic layer was washed with saturated $NaHCO_3$ aqueous solution, followed by brine solution and dried over anhydrous $Na_2SO_4$ and filtered. The filtered solution was concentrated under reduced pressure and the resulting crude compound was purified by flash column chromatography (100-200) silica gel using 20% EtOAc/Pet ether as a eluent to afford the title compound (1.2 g, 47.8%) as a pale yellow liquid.

LC-MS (method 14): $R_t$=1.26 min; m/z=220.0 ($M+H^+2$).

Step b. 2-Bromo-4-(2-bromoethoxy)pyridine

To a stirred solution of the compound obtained in the previous section, step a (1.1 g, 5.0 mmol) in DCM, $PPh_3$ (1.57 g, 1.2 eq) and $CBr_4$ (3.31 g, 10 mmol) were added at 0° C. It was stirred at rt for 12 h. The reaction mixture was quenched with ice cold water and extracted with DCM. The organic layer was washed with saturated $NaHCO_3$ aqueous solution, followed by brine solution and dried over anhydrous $Na_2SO_4$ and filtered. The solution filtrated was concentrated under reduced pressure and the resulting crude compound was purified by flash column chromatography (230-400) silica gel using 10% EtOAc/Pet ether as a eluent to afford the title compound (0.9 g, 64%) as a pale yellow liquid.

LC-MS (method 14): $R_t$=2.18 min; m/z=281.9 ($M+H^+$).

Step c. 2-Bromo-4-(2-(4,4-difluoropiperidin-1-yl) ethoxy)pyridine

To a stirred solution of the compound obtained in the previous section, step b (400 mg, 1.42 mmol) in AcN, $K_2CO_3$ (0.58 g, 4.26 mmol), NaI (0.1 g, 0.71 mmol) and difluoropiperidine hydrochloride (0.25 g, 2.13 mmol) were added at rt and then heated at 80° C. for 12 h. Organic solvents were evaporated to dryness. The obtained crude residue was dissolved in water and DCM. The combined organic layers were washed with water followed by brine solution and dried over anhydrous $Na_2SO_4$ and filtered. The filtered solution was concentrated under reduced pressure and the resulting crude compound was purified by flash column chromatography (230-400) silica gel using 50% EtOAc/Pet ether as a eluent to afford the title compound (0.350 g, 76.7%) as a pale yellow liquid.

LC-MS (method 15): $R_t$=2.91 min; m/z=321.30 ($M+H^+$).

Following a similar procedure to that described in reference example 17, but using the corresponding starting material, the following compound was obtained:

| Reference example | Compound name | Starting material | HPLC method | $R_t$ (min) | m/z |
|---|---|---|---|---|---|
| 17a | 4-(2-((2-Bromopyridin-4-yl)oxy)ethyl)morpholine | Morpholine | 14 | 1.45 | 289.0 ($M + H^+ + 2$) |

Reference Example 18

4-(4,4,5,5-Tetramethyl-1,3,2-dioxaborolan-2-yl)-1-((2-(trimethylsilyl)ethoxy)methyl)-1H-pyrazole To a stirred solution of 4-(4,4,5,5-tetramethyl-1,3,2-dioxaborolan-2-yl)-1H-pyrazole (2 g, 10.3 mmol) in DMF (30 mL), (2-(chloromethoxy)ethyl)trimethylsilane (2 g, 12.3 mmol), and $Cs_2CO_3$ (10 g, 30.9 mmol) were added. The resulting mixture was stirred at rt for 3 h. Solvents were evaporated and the crude residue was diluted with ice cold water and extracted with EtOAc. The combined organic layers were dried over anhydrous $Na_2SO_4$ and filtered. The filtered solution was concentrated under reduced pressure and the resulting crude compound was purified by flash column chromatography using 20-30% EtOAc/Pet ether to get the title compound (1.5 g, 44%) as pale yellow gummy.

LC-MS (method 14): $R_t$=3.08 min; m/z=325.2 ($M+H^+$.

Reference Example 19

5-Bromo-1-propyl-3-(1-((2-(trimethylsilyl)ethoxy) methyl)-1H-pyrazol-4-yl)1H-pyrrolo[2,3-c]pyridine Step a. 5-Bromo-3-iodo-1H-pyrrolo[2,3-c]pyridine To a stirred solution of 5-bromo-1H-pyrrolo[2,3-c]pyridine (1 g, 5.1 mmol) in DMF, KOH (0.86 g, 15.3 mmol) was added. It was stirred at rt for 20 minutes and then, iodine (1.54 g, 6.12 mmol) was added. The resulting mixture was stirred at rt for 16 h. The reaction mixture was evaporated under vacuum to get a crude residue. Crushed ice was added to the obtained crude residue and the precipitated solid was filtered, dried, and washed with diethylether to get 1 g (60%) of a crude compound that was used for the next step without any further purification.

LC-MS (method 6): $R_t$=1.94 min; m/z=323.01 ($M+H^+$).

Step b. 5-Bromo-3-iodo-1-propyl-1H-pyrrolo[2,3-c] pyridine

To a stirred solution of the compound obtained in the previous section, step a (1 g, 3.1 mmol) in DMF, NaH (60%) (0.371 g, 9.2 mmol) was added at 0° C. After 15 minutes, bromopropane (0.45 g, 3.72 mmol) was added slowly and stirred at rt for 3 h. To the reaction mixture, crushed ice was added, and the precipitated solid was filtered, dried, and washed with diethyl ether and n-pentane to get 900 mg (79%) of a crude compound that was used for the next step without any further purification.

LC-MS (method 6): $R_t$=2.28 min; m/z=365.01 (M+H$^+$).

Step c. 5-Bromo-1-propyl-3-(1-((2-(trimethylsilyl) ethoxy)methyl)-1H-pyrazol-4-yl)-1H-pyrrolo[2,3-c] pyridine To a stirred solution of the compound obtained in the previous section, step b (500 mg, 1.4 mmol) in) in a DMF/water 1:1 mixture, reference example 18 (0.545 g, 1.7 mmol), and $Cs_2CO_3$ (1.36 g, 4.2 mmol) were added. The resulting solution was degassed with nitrogen for 15 minutes, then $PdCl_2$dppf (0.1 g, 0.14 mmol) was added and stirred at 90° C. for 16 h. The reaction mixture was evaporated under vacuum to get a crude residue that was diluted with cold water and extracted with EtOAc. The combined organic layers were dried over anhydrous $Na_2SO_4$ and filtered. The filtered solution was concentrated under reduced pressure and the resulting crude compound was purified by flash column chromatography using 20-30% EtOAc/Pet ether to get the title compound (380 mg, 63%) as pale brown gummy.

LC-MS (method 6): $R_t$=2.39 min; m/z=435.34 (M+H$^+$).

Following a similar procedure to that described in reference example 19, but using the corresponding starting material, the following compound was obtained:

| Reference example | Compound name | Starting material | HPLC method | $R_t$ (min) | m/z |
|---|---|---|---|---|---|
| 19a | 5-Bromo-1-methyl-3-(1-((2-(trimethylsilyl)ethoxy)methyl)-1H-pyrazol-4-yl)-1H-pyrrolo[2,3-c]pyridine | Iodomethane | 6 | 2.25 | 407.32 (M + H$^+$). |
| 19b | 5-Bromo-1-(2-methoxyethyl)-3-(1-((2-(trimethylsilyl)ethoxy)methyl)-1H-pyrazol-4-yl)-1H-pyrrolo[2,3-c]pyridine | 1-Bromo-2-methoxyethane | 6 | 2.27 | 451.31 (M + H$^+$). |

Reference Example 20

N-(2-Bromopyridin-4-yl)-2-(4,4-difluoropiperidin-1-yl)acetamide

Step a. N-(2-Bromopyridin-4-yl)-2-chloroacetamide

To a stirred solution of 2-bromopyridin-4-amine (2 g, 11.5 mmol) in DCM (40 mL), DIPEA (4 mL, 23 mmol) and chloroacetyl chloride (1.85 mL, 23 mmol) were added at 0° C. It was stirred at rt for 3 h. The reaction mixture was diluted with EtOAc and washed with water. The organic layer was dried over anhydrous $Na_2SO_4$, filtered and concentrated under reduced pressure. The crude compound was purified by column chromatography and eluted at 20% EtOAc in pet ether to afford the title compound (2.2 g, 76.5%) as an off yellow solid.

LC-MS (method 6): $R_t$=1.70 min; m/z=249.02 (M+H$^+$).

Step b. N-(2-Bromopyridin-4-yl)-2-(4,4-difluoropiperidin-1-yl)acetamide

To a stirred solution of the compound obtained in the previous section, step a (2.1 g, 8.4 mmol) in AcN (50 mL), $K_2CO_3$ (3.5 g, 25.2 mmol), NaI (1.62 g, 10.9 mmol), and 4,4-difluoropiperidine hydrochloride (1.52 g, 12.6 mmol) were added at 0° C. It was stirred at rt for 16 h. The reaction mixture was filtered through a celite pad and washed with EtOAc (50 mL). The organic layer was dried over anhydrous $Na_2SO_4$, filtered and concentrated under reduced pressure to afford a crude compound that was used for the next step without any further purification (1.5 g, 53.4%)

LC-MS (method 6): $R_t$=1.42 min; m/z=336.16 (M+H$^+$+2).

Reference Example 21

2-Bromo-N(2-(4,4-difluoropiperidin-1-yl)ethyl)pyridin-4-amine

To a stirred solution of reference example 20 (1.0 g, 2.97 mmol) in THF (40 mL), $LiAlH_4$ (0.135 g, 3.56 mmol) was added at 0° C. It was stirred at rt for 3 h. The reaction mixture was poured into crushed ice water and diluted with EtOAc. The resulting mixture was filtered through a celite pad and concentrated under reduced pressure to afford a crude compound that was used for the next step without any further purification (0.5 g, 52.6

LC-MS (method 19): $R_t$=3.44 min; m/z=320.31 (M+H$^+$).

Reference Example 22

5-Bromo-3-(piperidin-1-ylmethyl)-1H-pyrazolo[3,4-c]pyridine

Following a similar procedure to that described in reference example 5, but using 5-bromo-1H-pyrazolo[3,4-c]pyridine instead of reference example 2, the desired compound was obtained.

LC-MS (method 6): $R_t$=1.12 min; m/z=295.18 (M+H$^+$),

Reference Example 23

6-Bromo-1-(2-(4,4-difluoropiperidin-1-yl)ethyl)-1H-pyrrolo[3,2-c]pyridine

Step a. 6-Bromo-1-(2-bromoethyl)-1H-pyrrolo[3,2-c]pyridine

To a stirred 40% NaOH aqueous solution (15 mL), 6-bromo-1H-pyrrolo[3,2-c]pyridine (1 g, 5.07 mmol), TBAB (163 mg, 0.50 mmol) and 1,2-dibromoethane (15 mL) were added. The resulting mixture was stirred at 80° C. for 12 h. The reaction mixture was quenched with water and extracted EtOAc. The organic layer was dried over anhydrous $Na_2SO_4$, concentrated under reduced pressure to get a crude compound that was used for the next step without any further purification (1.8 g).

LC-MS (method 6): $R_t$=1.77 min; m/z=304.80 (M+H$^+$).

Step b. 6-Bromo-1-(2-(4,4-difluoropiperidin-1-yl)ethyl)-1H-pyrrolo[3,2-c]pyridine To a stirred solution of the compound obtained in the previous section, step a (1 g, 3.2 mmol) in AcN (50 mL) was added 4,4-difluoropiperidine hydrochloride (780 mg, 5 mmol), $K_2CO_3$ (1.3 g, 9.6 mmol). The resulting suspension was stirred at 70° C. for 16 h. The reaction mixture was poured into cold water and extracted with EtOAc (2×80 mL). The organic layer was dried and concentrated to get a crude compound that was purified by flash column chromatography in 230-400 silica gel 28% EtOAc/pet ether as an eluent to afford the title compound (650 mg, 59%) as an off white solid.

LC-MS (method 6): $R_t$=1.26 min; m/z=344.26 (M+H$^+$).

Reference Example 24

N-(2-Bromopyridin-4-yl)-3-phenylpropanamide

To a stirred solution of 2-bromopyridin-4-amine (500 mg, 2.9 mmol) in THE (20 mL), 3-phenylpropanoyl chloride (585 mg, 3.5 mmol) and DIPEA (1.5 mL, 8.7 mmol) were added and it was stirred at rt for 16 h. The reaction mixture was poured to into ice water (50 ml) and extracted with EtOAc (2×100 mL). The organic layer was dried over anhydrous $Na_2SO_4$, filtered to obtain a crude residue that was triturated in n-pentane and dried to afford the title compound (880, 36%) as a gummy solid.

LC-MS (method 14): $R_t$=2.27 min; m/z=305.0 (M+H$^+$).

Reference Example 25

6-Bromo-1-(pyridin-4-ylmethyl)-1H-pyrrolo[3,2-c]pyridine

To a stirred solution of 6-bromo-1H-pyrrolo[3,2-c]pyridine (1 g, 5.07 mmol) in DMF (25 mL), $Cs_2CO_3$ (4.95 g, 15.21 mmol) and 4-(bromomethyl)pyridine hydrobromide (1.92 g, 7.60 mmol) were added. The resulting suspension was allowed to stir at rt, and then heated to 50° C. for 16 h. The reaction mixture was poured into ice water and extracted with EtOAc (2×120 mL). The organic layer was washed with water and brine solution, dried over anhydrous $Na_2SO_4$, and filtered. The resulting solution was concentrated under reduced pressure to get a crude residue that was purified by flash column chromatography in 230-400 silica gel 70% EtOAc/pet ether as an eluent to afford the title compound (800 mg, 57.7%) of the title compound as a light brown solid.

LC-MS (method 15): $R_t$=2.33 min; m/z=288.27 (M+H$^+$).

Following a similar procedure to that described in reference example 25, but using in each case the corresponding starting materials, the following compounds were obtained:

| Reference example | Compound name | Starting material | HPLC method | $R_t$ (min) | m/z |
|---|---|---|---|---|---|
| 25a | 6-Bromo-1-(2-methoxyethyl)-1H-pyrrolo[3,2-c]pyridine | 6-Bromo-1H-pyrrolo[3,2-c]pyridine and 1-bromo-2-methoxyethane | 6 | 1.50 | 255.0 (M + H$^+$) |
| 25b | 6-Bromo-1-(pyridin-3-ylmethyl)-1H-pyrrolo[3,2-c]pyridine | 6-Bromo-1H-pyrrolo[3,2-c]pyridine and 3-(bromomethyl)pyridine | 21 | 1.26 | 288.0 (M + H$^+$) |
| 25c | 6-Bromo-1-(pyridin-2-ylmethyl)-1H-pyrrolo[3,2-c]pyridine | 6-Bromo-1H-pyrrolo[3,2-c]pyridine and 2-(bromomethyl)pyridine hydrobromide | 6 | 1.56 | 287.9 (M + H$^+$) |
| 25d | 5-Bromo-1-(2-methoxyethyl)-1H-pyrazolo[3,4-c]pyridine | 5-Bromo-1H-pyrazolo[3,4-c]pyridine and 1-bromo-2-methoxyethane | 19 | 3.28 | 256.2 (M + H$^+$) |
| 25e | 5-Bromo-2-(2-methoxyethyl)-2H-pyrazolo[3,4-c]pyridine | 5-Bromo-1H-pyrazolo[3,4-c]pyridine and 1-bromo-2-methoxyethane | 19 | 3.08 | 256.2 (M + H$^+$) |
| 25f | 6-Bromo-1-((1-methyl-1H-pyrazol-4-yl)methyl)-1H-pyrrolo[3,2-c]pyridine | 6-Bromo-1H-pyrrolo[3,2-c]pyridine and 4-(chloromethyl)-1-methyl-1H-pyrazole | 6 | 1.51 | 291.10 (M + H$^+$) |

Reference Example 26

3-Bromo-1-(tetrahydro-2H-pyran-2-yl)-1H-pyrazolo [4,3-b]pyridine

To a stirred solution of 3-bromo-1H-pyrazolo[4,3-b]pyridine (200 mg, 1.01 mmol) in DMF (5 mL), 3,4-dihydro-2H-pyran (127 mg, 1.51 mmol) and a catalytic amount of pTSA were added at rt. The resulting solution was stirred at 85° C. for 24 h. The reaction was cooled to rt, diluted with water and extracted with EtOAc. The organic layer was washed with water and brine solution, dried over anhydrous $Na_2SO_4$, and filtered. The resulting solution was concentrated under reduced pressure to get crude a residue that was purified by flash column chromatography to afford the title compound (150 mg, 52.8%).

LC-MS (method 1): $R_t$=2.24 min; m/z=282.30 ($M+H^+$).

Reference Example 27

5-(3-(1H-Pyrazol-1-yl)propoxy)-2-bromopyridine

To a stirred solution of 1H-pyrazole (378 mg, 5.55 mmol) in) in DMF (10 mL), 60% NaH (666 mg, 16.6 mmol) was added at 0° C. and it was stirred at rt for 15 min. Then, the compound obtained in reference example 6, section a, (1.25 g, 6.1 mmol) was added (slowly). It was stirred at rt for 3 h. It was purified by silica gel column chromatography using 30-80% EtOAc/Pet ether to afford the title compound (1.2 g, 70%) as off-white solid.

LC-MS (method 14): $R_t$=2.09 min; m/z=282.0 ($M+H^+$).

Reference Example 28

6-Bromo-1-(1-(2,2,2-trifluoroethyl)piperidin-4-yl)-1H-pyrrolo[3,2-c]pyridine

Step a. Tert-butyl 4-(6-bromo-1H-pyrrolo[3,2-c] pyridin-1-yl)piperidine-1-carboxylate To a stirred solution of tert-butyl 4-(methylsulfonyloxy) piperidine-1-carboxylate in DMF (30 mL), $Cs_2CO_3$ (3.08 g. 9.5 mmol) and 6-bromo-1H-pyrrolo[3,2-c]pyridine (372 mg, 1.9 mmol) were added at rt. The reaction mixture was stirred at 90° C. for 12 h. The reaction mixture was quenched with ice water and extracted with DCM. The organic layer was dried over anhydrous $Na_2SO_4$, and it was concentrated under reduced pressure. The crude compound was purified by flash column chromatography using 20% EtOAc in pet ether as an eluent to afford the title compound (0.60 g, 44%).

LC-MS (method 14): $R_t$=2.65 min; m/z=380.0 ($M+H^+$).

Step b. 6-Bromo-1-(piperidin-4-yl)-1H-pyrrolo[3,2-c]pyridine hydrochloride

To a stirred solution the compound obtained in the previous section, step a, (0.6 g, 1.6 mmol) in dioxane (25 mL), 4M HCl in dioxane (0.2 mL) was added. The resulting mixture was stirred at rt for 3 h. Organic solvents were removed under vacuum, and the crude residue was triturated with diethyl ether. It was filtered under reduced pressure to afford 400 mg (89%) of the title compound LC-MS (method 14): $R_t$=1.23 min; m/z=280.0 ($M+H^+$).

Step c. 6-Bromo-1-(1-(2,2,2-trifluoroethyl)piperidin-4-yl)-1H-pyrrolo[3,2-c]pyridine To a stirred solution the compound obtained in the previous section, step b, (200 mg, 0.7 mmol) in acetone (15 ml), $K_2CO_3$ (0.483 mg, 3.5 mmol) and 2,2,2-trifluoroethyltrifluoromethanesulfonate (450 mg, 1.4 mmol) were added at rt. It was stirred at 55° C. overnight. Organic solvents were removed under vacuum. The crude residue was extracted with DCM/water. Then combined organic layer was concentrated under reduced pressure to afford the title compound (150 mg. 58%) as an off white solid.

LC-MS (method 6): $R_t$=2.07 min; m/z=362.24 ($M+H^+$).

Reference Example 29

5-Bromo-1-butyl-3-(1-methyl-1,2,3,6-tetrahydropyridin-4-yl)-1H-pyrrolo[2,3-c]pyridine Step a. 5-Bromo-3-(1-methyl-1,2,3,6-tetrahydropyridin-4-yl)-1H-pyrrolo[2,3-c]pyridine To a stirred solution of 5-bromo-1H-pyrrolo[2,3-c]pyridine (1.0 g, 5.07 mmol) in MeOH (20 mL), powder KOH (1.13 g, 20.28 mmol) was added. The resulting mixture was stirred at rt for 10 minutes. Then, 1-methylpiperidin-4-one (1.14 g, 10.14 mmol) was added and it was refluxed for 16 h. The reaction mixture was quenched with water and extracted with 10% MeOH in DMC. The separated organic layer was dried over anhydrous $Na_2SO_4$, filtered and concentrated under reduced pressure to afford 800 mg (54%) of the title compound.

LC-MS (method 6): $R_t$=0.95 min; m/z=290.20 ($M-H^+$).

Step b. 5-Bromo-1-butyl-3-(1-methyl-1,2,3,6-tetrahydropyridin-4-yl)-1H-pyrrolo[2,3-c]pyridine To a stirred solution the compound obtained in the previous section, step a (800 mg, 2.74 mmol) in DMF (10 mL), NaH (60%) (325 mg, 8.22 mmol) were added at 0° C. and it was stirred for 15 min. Then, iodobutane (1.0 g, 5.48 mmol) was added and reaction mixture was stirred at rt for 16 h. The reaction mixture was quenched with water and extracted with EtOAc and the organic layer was dried over anhydrous $Na_2SO_4$, and it was concentrated under reduced pressure. The crude compound was purified by flash column chromatography using 25-30% EtOAc in pet ether as an eluent to afford the title compound (400 mg, 42%).

LC-MS (method 6): $R_t$=1.66 min; m/z=348.29 ($M+H^+$).

Reference Example 30

N,N-Dimethyl-3-(6-(trimethylstannyl)pyridin-3-yloxy)propan-1-amine)

To a stirred solution of reference example 6b (500 mg, 1.92 mmol) in toluene (20 mL), hexamethylditin (695 mg, 2.12 mmol), and $Pd(PPh_3)_4$ (223 mg, 0.192 mmol) were added at rt. The resulting solution was degassed with nitrogen for 10 min and heated to 110° C. for 16 h. The reaction mixture was evaporated under reduced pressure and the crude compound was purified by flash column chromatography on neutral alumina using 10% EtOAc in petroleum ether to afford the title compound (390 mg, 58%).

LC-MS (method 21): $R_t$=2.02 min; m/z=345.0 ($M+H^+$)

Reference Example 31

3-(2-Bromopyridin-4-yl)-5-(trifluoromethyl)-1,2,4-oxadiazole

Step a. 2-Bromo-N-hydroxyisonicotinimidamide

To a stirred solution of 2-bromoisonicotinonitrile (3 g, 16.4 mmol) in EtOH/MeOH (1:1) (50 mL), a 50% solution of $NH_2OH·HCl$ (2.2 g, 32.8 mmol) in $NaHCO_3$ (2.7 g, 32.8 mmol) was added. The resulting solution was heated to 60° C., for 3 h. The reaction mixture was evaporated under reduced pressure and poured into ice water (20 mL) and extracted with EtOAc (2×150 mL). The organic layer was dried over anhydrous $Na_2SO_4$, and filtered. to afford a crude compound that was used for the next step without any further purification.

LC-MS (method 21): $R_t$=0.97 min; m/z=214.90 (M+H$^+$)

Step b. 3-(2-Bromopyridin-4-yl)-5-(trifluoromethyl)-1,2,4-oxadiazole

To a stirred solution the compound obtained in the previous section, step a (3.4 mg, 15.7 mmol) in THE (20 mL), trifluroacetic anhydride (4.94 g, 23.5 mmol) was added. The resulting solution was heated at 50° C. for 2 h. The reaction mixture was evaporated under vacuum, poured into ice water (30 mL) and extracted with EtOAc (2×50 mL). The organic layer was dried over anhydrous $Na_2SO_4$, filtered and the filtrated solution was concentrated to get a crude residue that was purified by flash column chromatography on silica using 25% EtOAc in petroleum ether to afford the title compound (3.2 g, 69%) as af white solid.

LC-MS (method 15): $R_t$=4.15 min; m/z=293.51 (M+H$^+$).

Reference Example 32

3-Bromo-1-(2-methoxyethyl)-1H-pyrazolo[4,3-b]pyridine

To a stirred solution of 3-bromo-1H-pyrazolo[4,3-b]pyridine (500 mg, 2.52 mmol) in DMF, NaH (60%) (201 mg, 5.04 mmol) was added at 0° C. and it was stirred for 15 min. Then, 1-bromo-2-methoxyethane (420 mg, 3.02 mmol) was added and the reaction mixture was stirred at rt for 2 h. The reaction mixture was quenched with water and extracted with EtOAc. The organic layer was dried over anhydrous $Na_2SO_4$, and it was concentrated under reduced pressure. The crude compound was purified by flash column chromatography on 230-400 silica using 45% EtOAc in pet ether as an eluent to afford the title compound (430 mg, 66%) as a gummy solid.

LC-MS (method 24): $R_t$=2.63 min; m/z=258.01 (M+2H$^+$).

Following a similar procedure to that described in reference example 32, but using in each case the corresponding starting materials, the following compounds were obtained:

| Reference example | Compound name | Starting material | HPLC method | $R_t$ (min) | m/z |
|---|---|---|---|---|---|
| 32a | 3-Bromo-1-ethyl-1H-pyrazolo[4,3-b]pyridine | 3-Bromo-1H-pyrazolo[4,3-b]pyridine and ethyl iodide | 25 | 1.70 | 226.04 (M + H$^+$) |
| 32b | 3-Bromo-1-methyl-1H-pyrazolo[4,3-b]pyridine | 3-Bromo-1H-pyrazolo[4,3-b]pyridine and methyl iodide | 6 | 1.54 | 212.05 (M + H$^+$) |

Reference Example 33

3-Bromo-1-(2-(1-methyl-1H-imidazol-2-yl)ethyl)-1H-pyrazolo[4,3-b]pyridine

To a stirred solution of 3-bromo-1H-pyrazolo[4,3-b]pyridine (800 mg, 4.03 mmol), in acetonitrile (10 mL) $Cs_2CO_3$ (3940 mg, 12.09 mmol), 2-(2-chloroethyl)-1-methyl-1H-imidazole (640 mg, 4.43 mmol) and NaI (303 mg, 2.02 mmol), were added at RT. The reaction mixture was heated at 90° C. overnight. The crude reaction was filtered through a celite pad, washed with EtOAc (50 mL), and the solution was evaporated to dryness. The crude compound was purified twice by column chromatography reverse phase with 10 mM Ammonium acetate/Acetonitrile to afford to afford the title compound (430 mg, 35%) as a gummy solid.

LC-MS (method 26): $R_t$=1.99 min; m/z=306.0 (M+H$^+$).

Reference Example 34

1-Methyl-3-(trimethylstannyl)-1H-pyrazolo[4,3-b]pyridine

Following a similar procedure to that described in reference example 30, but using reference example 32b, instead of reference example 6b, the desired compound was obtained.

Example 1

3-(2-(1-Butyl-1H-pyrrolo[2,3-c]pyridin-5-yl)pyridin-4-yl)-5-(trifluoromethyl)-1,2,4-oxadiazole

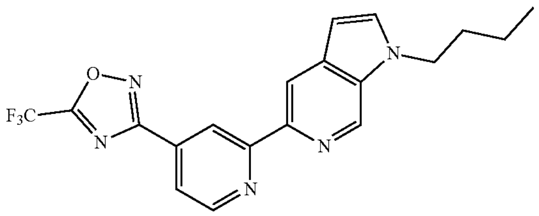 [SMILES: CCCCn1ccc2cc(-c3cc(-c4noc(C(F)(F)F)n4)ccn3)ncc21]

Step a. 2-(1-Butyl-1H-pyrrolo[2,3-c]pyridin-5-yl) isonicotinonitrile

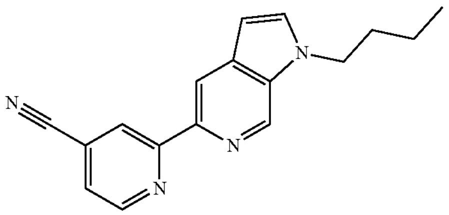 [SMILES: CCCCn1ccc2cc(-c3cc(C#N)ccn3)ncc21]

To a stirred solution of reference example 2 (800 mg, 3.16 mmol) in 1, 4-dioxane (5 mL), reference example 1 (928 mg, 3.47 mmol), CsF (948 mg, 6.32 mmol) and CuI (119 mg, 0.63 mmol) were added. The resulting solution was degassed with nitrogen for 5 minutes, and then Pd $(PPh_3)_4$ (358 mg, 0.31 equiv) was added. The reaction mixture was again degassed for another 5 min, and then heated at 110° C., for 16 h. The crude reaction was filtered through celite pad, washed with EtOAc (50 mL), and the filtrated solution was evaporated to dryness. The crude compound was purified by flash column chromatography in 230-400 silica gel 20% of EtOAc/pet-ether to afford the title compound (500 mg, 57%) as a light yellow solid.

LC-MS (method 6): $R_t$=1.66 min; m/z=277.54 (M+H$^+$).

Step b. 2-(1-Butyl-1H-pyrrolo[2,3-c]pyridin-5-yl)-N-hydroxyisonicotinimidamide

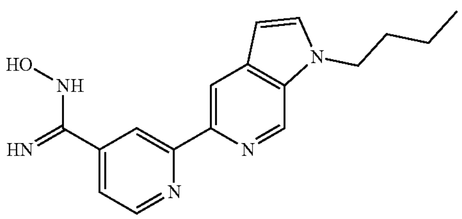 [SMILES: CCCCn1ccc2cc(-c3cc(C(=N)NO)ccn3)ncc21]

To a stirred solution the compound obtained in the previous section, step a (300 mg, 1.08 mmol) in EtOH/MeOH (1:1) (10 mL), 50% $NH_2OH{\cdot}HCl$ aqueous solution (300 mg, 2.16 mmol) was added. The resulting solution was heated to 60° C. for 5 h. The reaction mixture was evaporated under vacuum, poured into ice water (20 mL) and extracted with EtOAc (2×80 mL). The organic layer was dried over anhydrous $Na_2SO_4$, filtered and the filtrated solution was concentrated to get the title compound (320 mg, 95%), as a gummy solid.

LC-MS (method 6): $R_t$=1.47 min; m/z=310.27 (M+H$^+$).

Step c. 3-(2-(1-Butyl-1H-pyrrolo[2,3c]pyridin-5-yl)pyridin-4-yl)-5-(trifluoromethyl)-1,2,4-oxadiazole

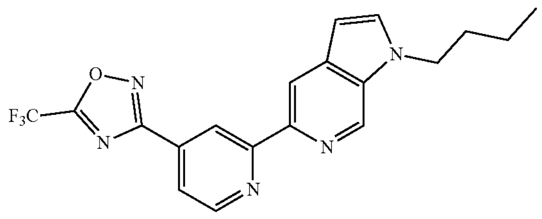 [SMILES: CCCCn1ccc2cc(-c3cc(-c4noc(C(F)(F)F)n4)ccn3)ncc21]

To a stirred solution the compound obtained in the previous section, step b (300 mg, 0.97 mmol) in THF (10 mL), trifluroacetic anhydride (243 mg, 1.16 mmol) was added. The resulting solution was heated at 50° C. for 4 h. The reaction mixture was evaporated under vacuum, poured into ice water (20 mL) and extracted with EtOAc (2×80 mL). The organic layer was dried over anhydrous $Na_2SO_4$, filtered and the filtrated solution was concentrated to get a crude residue that was purified by prep HPLC to afford the title compound (70 mg, 18.6%) as an off white solid.

LC-MS (method 6): $R_t$=2.00 min; m/z=388.28 (M+H$^+$).

Preparative HPLC Conditions: Column/dimensions: PRONTOSIL C18 (20×250 mm), 10.0 µm, Mobile phase: 0.1% FA in water: Acetonitrile (A:B); Gradient (Time/% B): 0/20, 1/20, 10/80, 10.1/98, 14/98, 14.1/20, 17/20, Flow rate: 20 ml/min Following a similar procedure to that described in example 1, but using in each case the corresponding starting materials, the following compounds were obtained:

| Example | Compound name | Starting material | HPLC method | $R_t$ (min) | m/z |
|---|---|---|---|---|---|
| 1a | 3-(2-(1-Propyl-1H-pyrrolo[2,3-c]pyridin-5-yl)pyridin-4-yl)-5-(trifluoromethyl)-1,2,4-oxadiazole | Reference example 2a | 15 | 4.25 | 374.29 (M + H$^+$) |

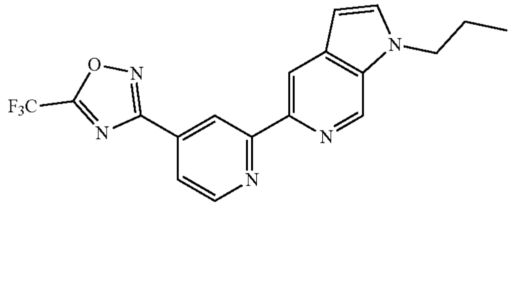 [SMILES: CCCn1ccc2cc(-c3cc(-c4noc(C(F)(F)F)n4)ccn3)ncc21]

-continued

| Example | Compound name | Starting material | HPLC method | $R_t$ (min) | m/z |
|---|---|---|---|---|---|
| 1b | 1-Butyl-N,N-dimethyl-5-(4-(5-(trifluoromethyl)-1,2,4-oxadiazol-3-yl)pyridin-2-yl)-1H-pyrrolo[2,3-c]pyridine-2-carboxamide 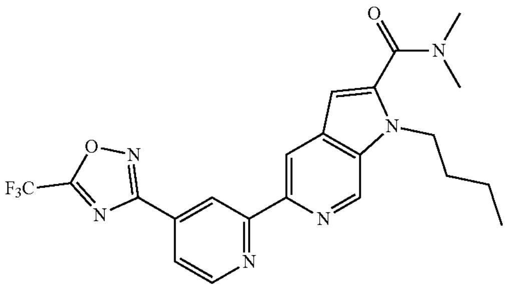 [SMILES: CCCCn1c(C(=O)N(C)C)cc2cc(-c3cc(-c4noc(C(F)(F)F)n4)ccn3)ncc21] | Reference example 3 | 15 | 3.96 | 459.38 (M + $H^+$) |
| 1c | N,N-Diethyl-3-((4'-(5-(trifluoromethyl)-1,2,4-oxadiazol-3-yl)-[2,2'-bipyridin]-5-yl)oxy)propan-1-amine (obtained as hemiformate salt) 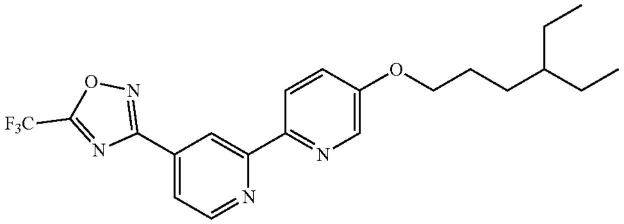 [SMILES: CCC(CC)CCCOc1ccc(-c2cc(-c3noc(C(F)(F)F)n3)ccn2)nc1] | Reference example 4 | 6 | 1.84 | 422.41 (M + $H^+$) |
| 1d | 1-Butyl-N-ethyl-5-(4-(5-(trifluoromethyl)-1,2,4-oxadiazol-3-yl)pyridin-2-yl)-1H-pyrrolo[2,3-c]pyridine-2-carboxamide 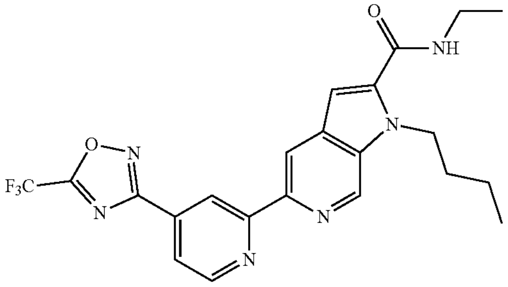 [SMILES: CCCCn1c(C(=O)NCC)cc2cc(-c3cc(-c4noc(C(F)(F)F)n4)ccn3)ncc21] | Reference example 3b | 16 | 6.74 | 459.41 (M + $H^+$) |
| 1e | 4-(3-((4'-(5-(Trifluoromethyl)-1,2,4-oxadiazol-3-yl)-[2,2'-bipyridin]-5-yl)oxy)propyl)morpholine (obtained as hemitrifluoroacetate salt) 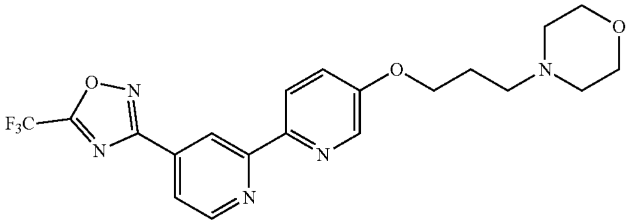 [SMILES: FC(F)(F)c1nc(-c2ccnc(-c3ccc(OCCCN4CCOCC4)cn3)c2)no1] | Reference example 6b | 15 | 3.35 | 436.19 (M + $H^+$) |

-continued

| Example | Compound name | Starting material | HPLC method | $R_t$ (min) | m/z |
|---|---|---|---|---|---|
| 1f | 3-(5'-(3-(4,4-Difluoropiperidin-1-yl)propoxy)-[2,2'-bipyridin]-4-yl)-5-(trifluoromethyl)-1,2,4-oxadiazole (obtained as diformate salt) 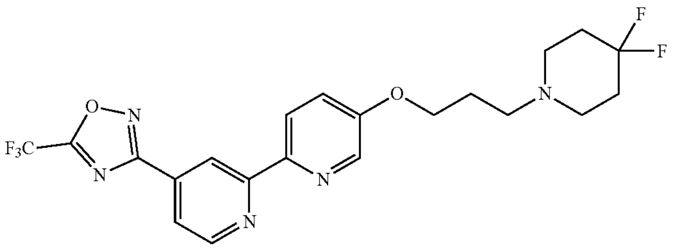 [SMILES: FC1(F)CCN(CCCOc2ccc(-c3cc(-c4noc(C(F)(F)F)n4)ccn3)nc2)CC1] | Reference example 6 | 16 | 6.82 | 470.26 (M + $H^+$) |
| 1g | 3-(2-(3-(Piperidin-1-ylmethyl)-1-propyl-1H-pyrrolo[2,3-c]pyridin-5-yl)pyridin-4-yl)-5-(trifluoromethyl)-1,2,4-oxadiazole (obtained as trifluoroacetate salt) 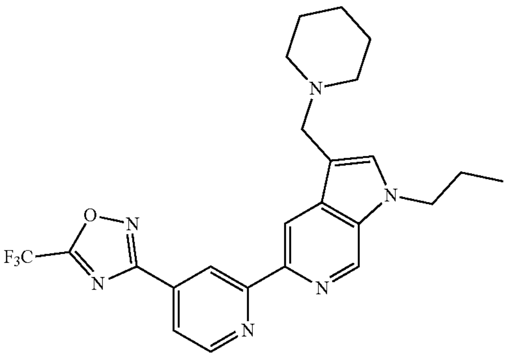 [SMILES: CCCn1cc(CN2CCCCC2)c2cc(-c3cc(-c4noc(C(F)(F)F)n4)ccn3)ncc21] | Reference example 5a | 14 | 2.48 | 471.1 (M + $H^+$) |
| 1h | 4-((1-Propyl-5-(4-(5-(trifluoromethyl)-1,2,4-oxadiazol-3-yl)pyridin-2-yl)-1H-pyrrolo[2,3-c]pyridin-3-yl)methyl)morpholine 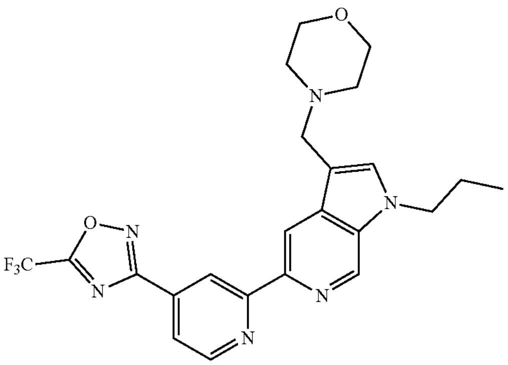 [SMILES: CCCn1cc(CN2CCOCC2)c2cc(-c3cc(-c4noc(C(F)(F)F)n4)ccn3)ncc21] | Reference example 5b | 14 | 2.79 | 473.2 (M + $H^+$) |

-continued

| Example | Compound name | Starting material | HPLC method | $R_t$ (min) | m/z |
|---|---|---|---|---|---|
| 1i | N-Butyl-3-methoxy-N-(4'-(5-(trifluoromethyl)-1,2,4-oxadiazol-3-yl)-[2,2'-bipyridin]-5-yl)propanamide 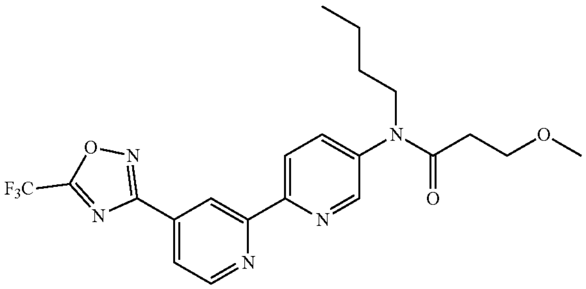 [SMILES: CCCCN(C(=O)CCOC)c1ccc(-c2cc(-c3noc(C(F)(F)F)n3)ccn2)nc1] | Reference example 7 | 16 | 6.63 | 450.37 (M + H$^+$) |
| 1j | N-(Cyclopropylmethyl)-N-methyl-4'-(5-(trifluoromethyl)-1,2,4-oxadiazol-3-yl)-[2,2'-bipyridin]-5-amine 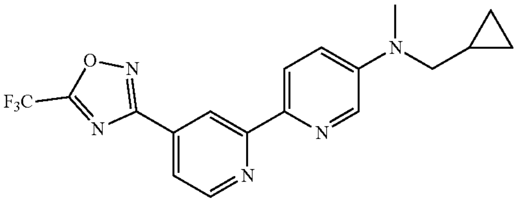 [SMILES: CN(CC1CC1)c1ccc(-c2cc(-c3noc(C(F)(F)F)n3)ccn2)nc1] | Reference example 8 | 16 | 7.05 | 376.33 (M + H$^+$) |
| 1k | $N^1$,$N^1$-Diethyl-$N^3$-(4'-(5-(trifluoromethyl)-1,2,4-oxadiazol-3-yl)-[2,2'-bipyridin]-5-yl)propane-1,3-diamine (**) 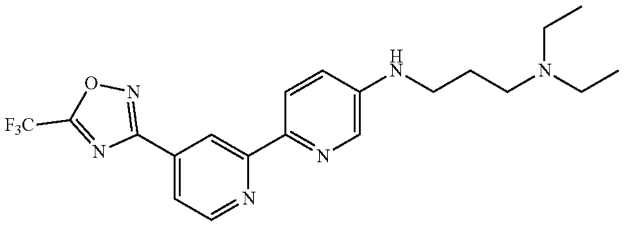 [SMILES: CCN(CC)CCCNc1ccc(-c2cc(-c3noc(C(F)(F)F)n3)ccn2)nc1] | Reference example 9 | 6 | 1.69 | 421.39 (M + H$^+$) |
| 1l | N-(3-(4,4-Difluoropiperidin-1-yl)propyl)-N-methyl-4'-(5-(trifluoromethyl)-1,2,4-oxadiazol-3-yl)-[2,2'-bipyridin]-5-amine 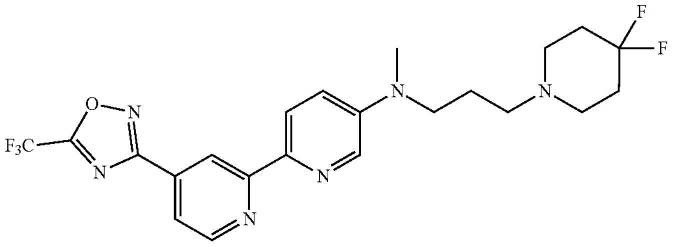 [SMILES: CN(CCCN1CCC(F)(F)CC1)c1ccc(-c2cc(-c3noc(C(F)(F)F)n3)ccn2)nc1] | Reference example 10 | 16 | 6.88 | 483.42 (M + H$^+$) |

-continued

| Example | Compound name | Starting material | HPLC method | $R_t$ (min) | m/z |
|---|---|---|---|---|---|
| 1m | N,N-Diethyl-3-(2-(4-(5-(trifluoromethyl)-1,2,4-oxadiazol-3-yl)pyridin-2-yl)pyrimidin-5-yloxy)propan-1-amine (obtained as hemiformate salt) 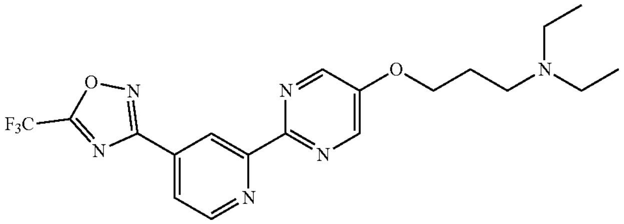 [SMILES: CCN(CC)CCCOc1cnc(-c2cc(-c3noc(C(F)(F)F)n3)ccn2)nc1] | Reference example 11 | 15 | 2.53 | 423.22 (M + $H^+$) |
| 1n | $N^1$,$N^1$-Diethyl-$N^3$-methyl-$N^3$-(4'-(5-(trifluoromethyl)-1,2,4-oxadiazol-3-yl)-2,2'-bipyridin-5-yl)propane-1,3-diamine (obtained as formate salt) 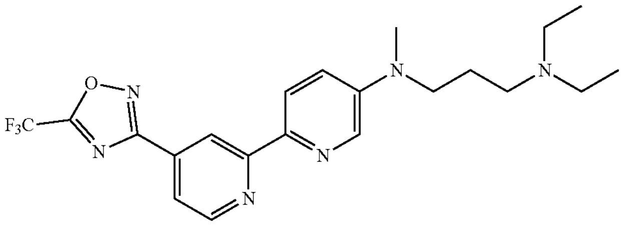 [SMILES: CCN(CC)CCCN(C)c1ccc(-c2cc(-c3noc(C(F)(F)F)n3)ccn2)nc1] | Reference example 12 | 6 | 2.08 | 435.40 (M + $H^+$) |
| 1o | 3-(2-(1-(Tetrahydro-2H-pyran-4-yl)-1H-pyrrolo[3,2-c]pyridin-6-yl)pyridin-4-yl)-5-(trifluoromethyl)-1,2,4-oxadiazole 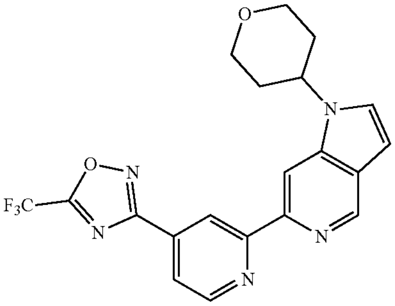 [SMILES: FC(F)(F)c1nc(-c2ccnc(-c3cc4c(ccn4C4CCOCC4)cn3)c2)no1] | Reference example 14 | 6 | 1.76 | 416.33 (M + $H^+$) |
| 1p | N-Ethyl-N-phenethyl-3-((4'-(5-(trifluoromethyl)-1,2,4-oxadiazol-3-yl)-[2,2'-bipyridin]-5-yl)oxy)propan-1-amine 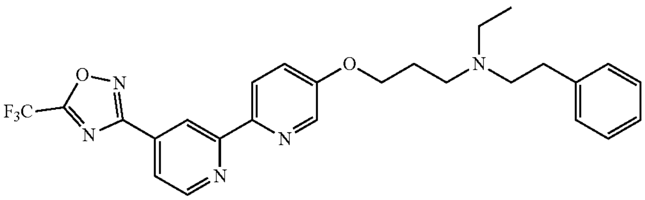 [SMILES: CCN(CCCOc1ccc(-c2cc(-c3noc(C(F)(F)F)n3)ccn2)nc1)CCc1ccccc1] | Reference example 15 | 6 | 2.12 | 498.48 (M + $H^+$) |

-continued

| Example | Compound name | Starting material | HPLC method | $R_t$ (min) | m/z |
|---|---|---|---|---|---|
| 1q | 2-Phenyl-N-(4'-(5-(trifluoromethyl)-1,2,4-oxadiazol-3-yl)-[2,2'-bipyridin]-5-yl)acetamide | Reference example 16 | 16 | 6.38 | 426.35 (M + $H^+$) |
| | 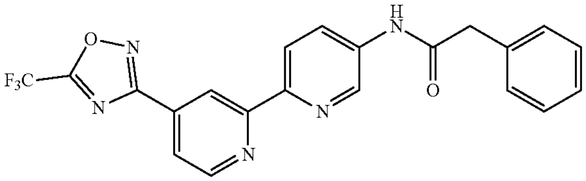 [SMILES: O=C(Cc1ccccc1)Nc1ccc(-c2cc(-c3noc(C(F)(F)F)n3)ccn2)nc1] | | | | |
| 1r | 3-(2-(1-((Tetrahydro-2H-pyran-4-yl)methyl)-1H-pyrrolo[3,2-c]pyridin-6-yl)pyridin-4-yl)-5-(trifluoromethyl)-1,2,4-oxadiazole | Reference example 14a | 16 | 6.33 | 430.38 (M + $H^+$) |
| | 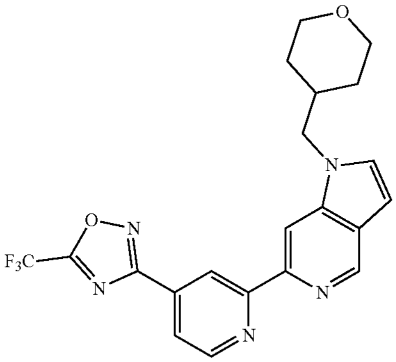 [SMILES: FC(F)(F)c1nc(-c2ccnc(-c3cc4c(ccn4CC4CCOCC4)cn3)c2)no1] | | | | |
| 1s | 3-(4'-(2-(4,4-Difluoropiperidin-1-yl)ethoxy)-[2,2'-bipyridin]-4-yl)-5-(trifluoromethyl)-1,2,4-oxadiazole | Reference example 17 | 16 | 5.56 | 456.16 (M + $H^+$) |
| | 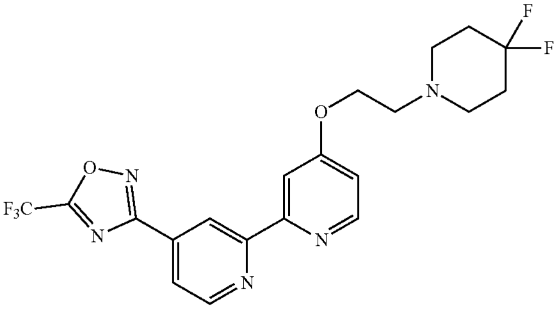 [SMILES: FC1(F)CCN(CCOc2ccnc(-c3cc(-c4noc(C(F)(F)F)n4)ccn3)c2)CC1] | | | | |
| 1t | 4-(2-((4'-(5-(Trifluoromethyl)-1,2,4-oxadiazol-3-yl)-[2,2'-bipyridin]-4-yl)oxy)ethyl)morpholine | Reference example 17a | 16 | 5.71 | 422.14 (M + $H^+$) |
| | 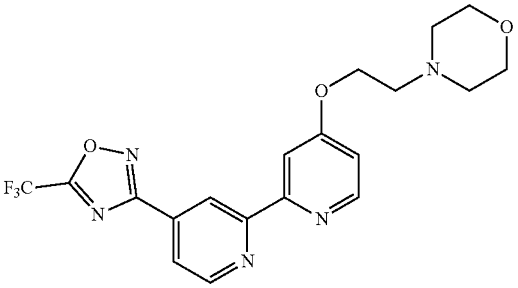 [SMILES: FC(F)(F)c1nc(-c2ccnc(-c3cc(OCCN4CCOCC4)ccn3)c2)no1] | | | | |

-continued

| Example | Compound name | Starting material | HPLC method | $R_t$ (min) | m/z |
|---|---|---|---|---|---|
| 1u | N,N,1-Trimethyl-5-(4-(5-(trifluoromethyl)-1,2,4-oxadiazol-3-yl)pyridin-2-yl)-1H-pyrrolo[2,3-c]pyridine-2-carboxamide (obtained as ditrifluoroacetate salt)<br>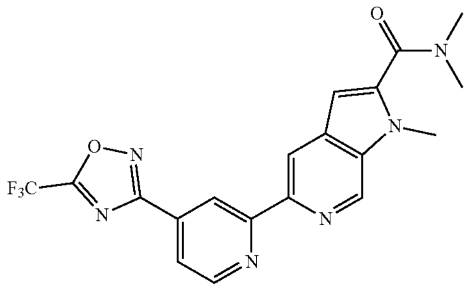 [SMILES: CN(C)C(=O)c1cc2cc(-c3cc(-c4noc(C(F)(F)F)n4)ccn3)ncc2n1C] | Reference example 3a | 16 | 5.84 | 417.37 (M + H$^+$) |
| 1v | 3-(2-(1-Propyl-3-(1H-pyrazol-4-yl)-1H-pyrrolo[2,3-c]pyridin-5-yl)pyridin-4-yl)-5-(trifluoromethyl)-1,2,4-oxadiazole<br>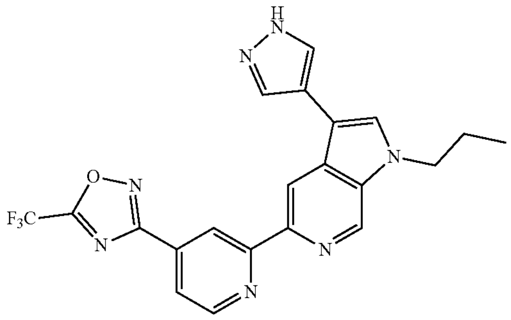 [SMILES: CCCn1cc(-c2cn[nH]c2)c2cc(-c3cc(-c4noc(C(F)(F)F)n4)ccn3)ncc21] | Reference example 19 | 15 | 3.69 | 440.32 (M + H$^+$) |
| 1w | 1-Butyl-N,N-diethyl-5-(4-(5-(trifluoromethyl)-1,2,4-oxadiazol-3-yl)pyridin-2-yl)-1H-pyrrolo[2,3-c]pyridine-2-carboxamide<br>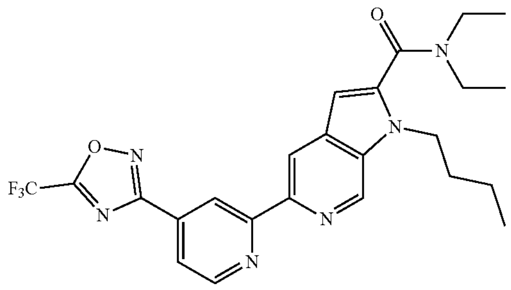 [SMILES: CCCCn1c(C(=O)N(CC)CC)cc2cc(-c3cc(-c4noc(C(F)(F)F)n4)ccn3)ncc21] | Reference example 3c | 18 | 6.15 | 487.2 (M + H$^+$) |
| 1x | 3-(2-(1-(2-Methoxyethyl)-1H-pyrrolo[2,3-c]pyridin-5-yl)pyridin-4-yl)-5-(trifluoromethyl)-1,2,4-oxadiazole<br>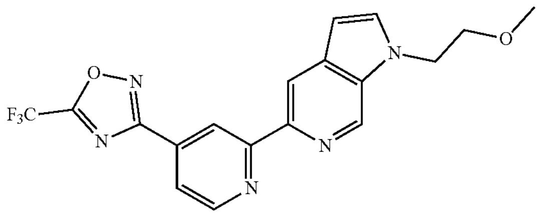 [SMILES: COCCn1ccc2cc(-c3cc(-c4noc(C(F)(F)F)n4)ccn3)ncc21] | Reference example 2b | 16 | 6.30 | 390.32 (M + H$^+$) |

-continued

| Example | Compound name | Starting material | HPLC method | $R_t$ (min) | m/z |
|---|---|---|---|---|---|
| 1y | 2-(4,4-Difluoropiperidin-1-yl)-N-(4'-(5-(trifluoromethyl)-1,2,4-oxadiazol-3-yl)-[2,2'-bipyridin]-4-yl)acetamide 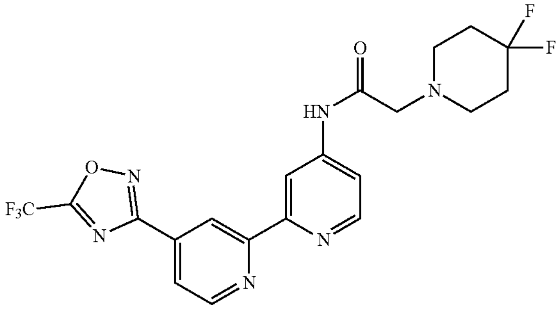 [SMILES: O=C(CN1CCC(F)(F)CC1)Nc1ccnc(-c2cc(-c3noc(C(F)(F)F)n3)ccn2)c1] | Reference example 20 | 18 | 5.39 | 469.1 (M + $H^+$) |
| 1z | N-(2-(4,4-Difluoropiperidin-1-yl)ethyl)-4'-(5-(trifluoromethyl)-1,2,4-oxadiazol-3-yl)-[2,2'-bipyridin]-4-amine (obtained as pentatrifluoroacetate salt) 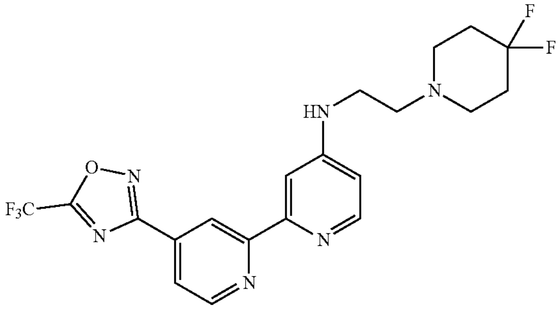 [SMILES: FC1(F)CCN(CCNc2ccnc(-c3cc(-c4noc(C(F)(F)F)n4)ccn3)c2)CC1] | Reference example 21 | 16 | 5.90 | 455.39 (M + $H^+$) |
| 1aa | 3-(2-(3-(Piperidin-1-ylmethyl)-1H-pyrazolo[3,4-c]pyridin-5-yl)pyridin-4-yl)-5-(trifluoromethyl)-1,2,4-oxadiazole (obtained as sesquitrifluoroacetate salt) 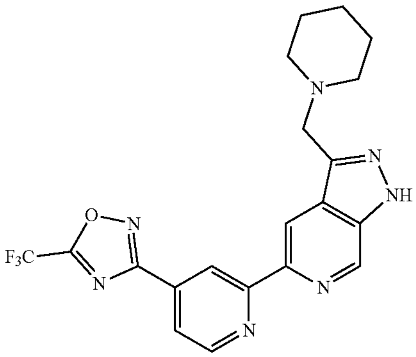 [SMILES: FC(F)(F)c1nc(-c2ccnc(-c3cc4c(CN5CCCCC5)n[nH]c4cn3)c2)no1] | Reference example 22 | 18 | 4.32 | 430.1 (M + $H^+$) |

-continued

| Example | Compound name | Starting material | HPLC method | $R_t$ (min) | m/z |
|---|---|---|---|---|---|
| 1ab | 3-(2-(1-(2-(4,4-Difluoropiperidin-1-yl)ethyl)-1H-pyrrolo[3,2-c]pyridin-6-yl)pyridin-4-yl)-5-(trifluoromethyl)-1,2,4-oxadiazole 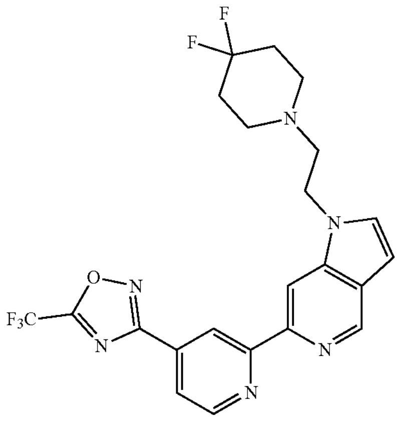 [SMILES: FC1(F)CCN(CCn2ccc3cnc(-c4cc(-c5noc(C(F)(F)F)n5)ccn4)cc32)CC1] | Reference example 23 | 16 | 6.77 | 479.42 (M + $H^+$) |
| 1ac | 1-Methyl-N-(4'-(5-(trifluoromethyl)-1,2,4-oxadiazol-3-yl)-[2,2'-bipyridin]-5-yl)piperidine-4-carboxamide (obtained as hemiformate salt) 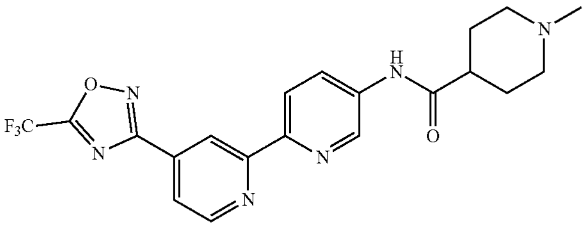 [SMILES: CN1CCC(C(=O)Nc2ccc(-c3cc(-c4noc(C(F)(F)F)n4)ccn3)nc2)CC1] | Reference example 16a | 6 | 1.75 | 433.40 (M + $H^+$) |
| 1ad | 3-Phenyl-N-(4'-(5-(trifluoromethyl)-1,2,4-oxadiazol-3-yl)-[2,2'-bipyridin]-4-yl)propanamide 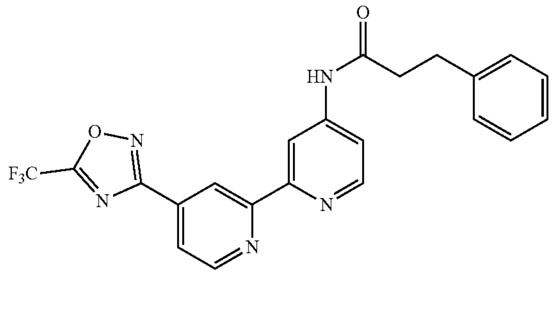 [SMILES: O=C(CCc1ccccc1)Nc1ccnc(-c2cc(-c3noc(C(F)(F)F)n3)ccn2)c1] | Reference example 24 | 18 | 5.60 | 440.1 (M + $H^+$) |

-continued

| Example | Compound name | Starting material | HPLC method | $R_t$ (min) | m/z |
|---|---|---|---|---|---|
| 1ae | 2-Cyclobutyl-N-(4'-(5-(trifluoromethyl)-1,2,4-oxadiazol-3-yl)-[2,2'-bipyridin]-4-yl)acetamide (obtained as hemitrifluoroacetate salt) 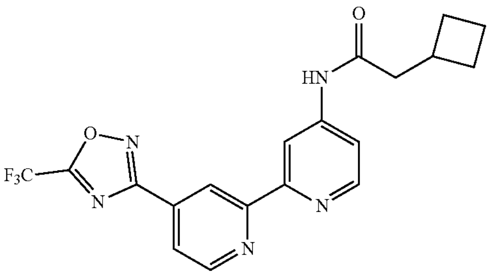 [SMILES: O=C(CC1CCC1)Nc1ccnc(-c2cc(-c3noc(C(F)(F)F)n3)ccn2)c1] | Reference example 16b | 18 | 5.49 | 404.01 (M + H$^+$) |
| 1af | N-(Piperidin-3-yl)-4'-(5-(trifluoromethyl)-1,2,4-oxadiazol-3-yl)-[2,2'-bipyridine]-4-carboxamide (*) 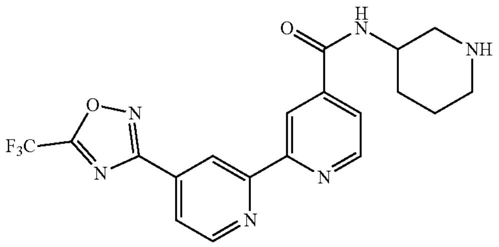 [SMILES: O=C(NC1CCCNC1)c1ccnc(-c2cc(-c3noc(C(F)(F)F)n3)ccn2)c1] | Reference example 16c | 18 | 3.90 | 419.1 (M + H$^+$) |
| 1ag | 3-(5'-(3-(1H-Pyrazol-1-yl)propoxy)-[2,2'-bipyridin]-4-yl)-5-(trifluoromethyl)-1,2,4-oxadiazole 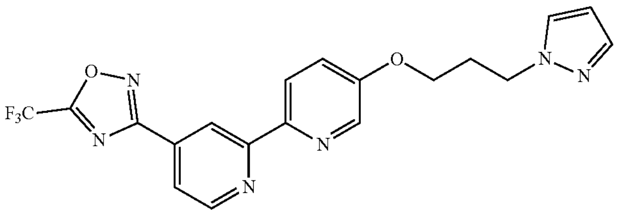 [SMILES: FC(F)(F)c1nc(-c2ccnc(-c3ccc(OCCCn4cccn4)cn3)c2)no1] | Reference example 27 | 16 | 6.34 | 417.20 (M + H$^+$) |
| 1ah | (1-Propyl-5-(4-(5-(trifluoromethyl)-1,2,4-oxadiazol-3-yl)pyridin-2-yl)-1H-pyrrolo[2,3-c]pyridin-3-yl)methanol (obtained as sesquitrifluoroacetate salt) 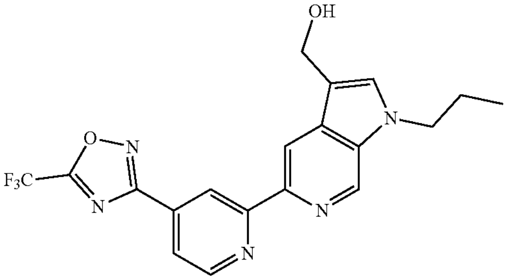 [SMILES: CCCn1cc(CO)c2cc(-c3cc(-c4noc(C(F)(F)F)n4)ccn3)ncc21] | Reference example 5c | 6 | 1.73 | 404.36 (M + H$^+$) |

-continued

| Example | Compound name | Starting material | HPLC method | $R_t$ (min) | m/z |
|---|---|---|---|---|---|
| 1ai | 3-(2-(3-(Methoxymethyl)-1-propyl-1H-pyrrolo[2,3-c]pyridin-5-yl)pyridin-4-yl)-5-(trifluoromethyl)-1,2,4-oxadiazole 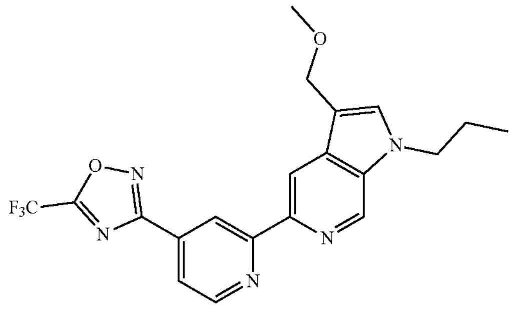 [SMILES: CCCn1cc(COC)c2cc(-c3cc(-c4noc(C(F)(F)F)n4)ccn3)ncc21] | Reference example 5c | 15 | 4.10 | 418.34 (M + $H^+$) |
| 1aj | (1-butyl-5-(4-(5-(trifluoromethyl)-1,2,4-oxadiazol-3-yl)pyridin-2-yl)-1H-pyrrolo[2,3-c]pyridin-3-yl)methanol 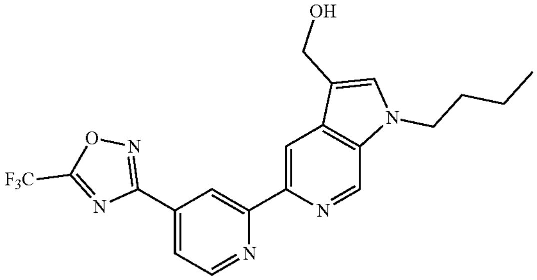 [SMILES: CCCCn1cc(CO)c2cc(-c3cc(-c4noc(C(F)(F)F)n4)ccn3)ncc21] | Reference example 5 | 6 | 1.80 | 418.27 (M + $H^+$) |
| 1ak | 3-(2-(1H-Pyrrolo[3,2-c]pyridin-6-yl)pyridin-4-yl)-5-(trifluoromethyl)-1,2,4-oxadiazole (obtained as hemiformate salt) 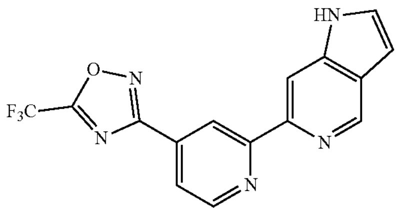 [SMILES: FC(F)(F)c1nc(-c2ccnc(-c3cc4[nH]ccc4cn3)c2)no1] | Reference example 25 | 16 | 5.80 | 332.24 (M + $H^+$) |
| 1al | 3-(2-(1-(Pyridin-4-ylmethyl)-1H-pyrrolo[3,2-c]pyridin-6-yl)pyridin-4-yl)-5-(trifluoromethyl)-1,2,4-oxadiazole (obtained as tritrifluoroacetate salt) 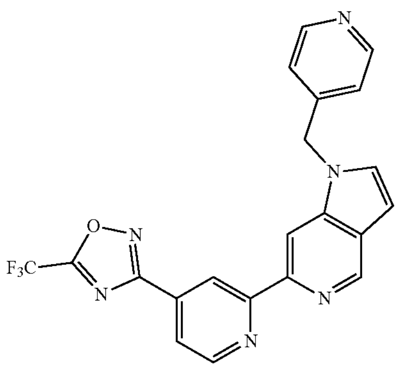 [SMILES: FC(F)(F)c1nc(-c2ccnc(-c3cc4c(ccn4Cc4ccncc4)cn3)c2)no1] | Reference example 25 | 6 | 1.57 | 423.33 (M + $H^+$) |

-continued

| Example | Compound name | Starting material | HPLC method | $R_t$ (min) | m/z |
|---|---|---|---|---|---|
| 1am | N-((1-Methylpiperidin-4-yl)methyl)-4'-(5-(trifluoromethyl)-1,2,4-oxadiazol-3-yl)-[2,2'-bipyridine]-4-carboxamide (obtained as hemipentatrifluoroacetate salt) 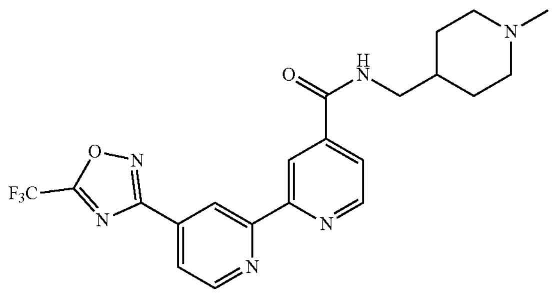 [SMILES: CN1CCC(CNC(=O)c2ccnc(-c3cc(-c4noc(C(F)(F)F)n4)ccn3)c2)CC1] | Reference example 16d | 16 | 5.10 | 447.39 (M + $H^+$) |
| 1an | N-((1-Methylpiperidin-4-yl)methyl)-4'-(5-(trifluoromethyl)-1,2,4-oxadiazol-3-yl)-[2,2'-bipyridine]-5-carboxamide (obtained as hemipentacetate salt) 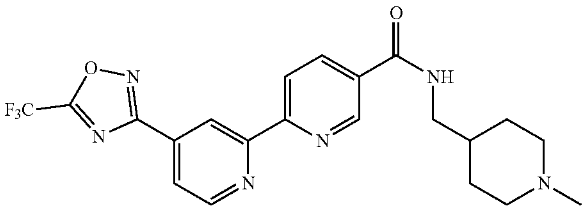 [SMILES: CN1CCC(CNC(=O)c2ccc(-c3cc(-c4noc(C(F)(F)F)n4)ccn3)nc2)CC1] | Reference example 16e | 18 | 4.32 | 447.1 (M + $H^+$) |
| 1ao | 3-(2-(1-(1-(2,2,2-Trifluoroethyl)piperidin-4-yl)-1H-pyrrolo[3,2-c]pyridin-6-yl)pyridin-4-yl)-5-(trifluoromethyl)-1,2,4-oxadiazole 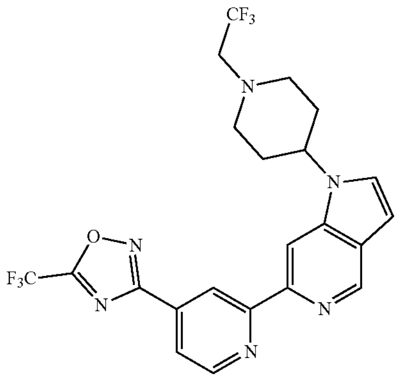 [SMILES: FC(F)(F)CN1CCC(n2ccc3cnc(-c4cc(-c5noc(C(F)(F)F)n5)ccn4)cc32)CC1] | Reference example 28 | 6 | 1.97 | 497.34 (M + $H^+$) |

-continued

| Example | Compound name | Starting material | HPLC method | $R_t$ (min) | m/z |
|---|---|---|---|---|---|
| 1ap | 3-(2-(1-Methyl-3-(1H-pyrazol-4-yl)-1H-pyrrolo[2,3-c]pyridin-5-yl)pyridin-4-yl)-5-(trifluoromethyl)-1,2,4-oxadiazole 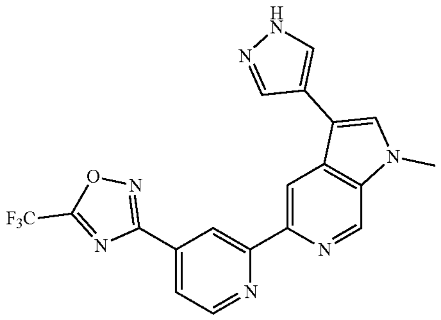 [SMILES: Cn1cc(-c2cn[nH]c2)c2cc(-c3cc(-c4noc(C(F)(F)F)n4)ccn3)ncc21] | Reference example 19a | 18 | 3.96 | 412.1 (M + $H^+$) |
| 1aq | 3-(2-(1-Butyl-3-(1-methyl-1,2,3,6-tetrahydropyridin-4-yl)-1H-pyrrolo[2,3-c]pyridin-5-yl)pyridin-4-yl)-5-(trifluoromethyl)-1,2,4-oxadiazole 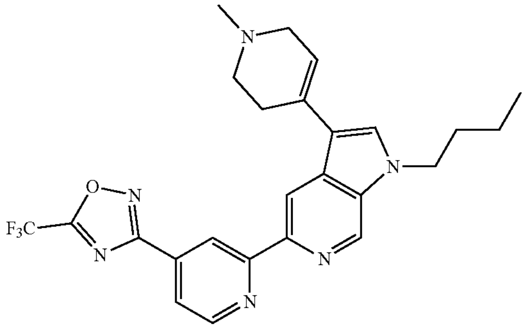 [SMILES: CCCCn1cc(C2=CCN(C)CC2)c2cc(-c3cc(-c4noc(C(F)(F)F)n4)ccn3)ncc21] | Reference example 29 | 16 | 6.42 | 483.41 (M + $H^+$) |
| 1ar | 1-(2-Methoxyethyl)-N,N-dimethyl-5-(4-(5-(trifluoromethyl)-1,2,4-oxadiazol-3-yi)pyridin-2-yl)-1H-pyrrolo[2,3-c]pyridine-2-carboxamide 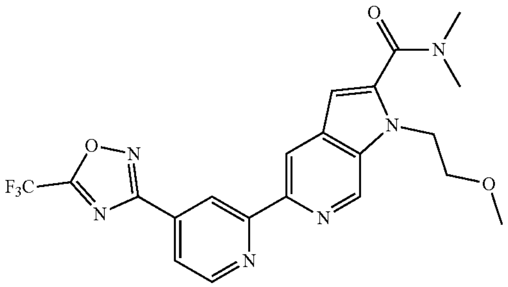 [SMILES: COCCn1c(C(=O)N(C)C)cc2cc(-c3cc(-c4noc(C(F)(F)F)n4)ccn3)ncc21] | Reference example 3d | 20 | 4.17 | 461.28 (M + $H^+$) |

-continued

| Example | Compound name | Starting material | HPLC method | $R_t$ (min) | m/z |
|---|---|---|---|---|---|
| 1as | 3-(2-(1-(2-Methoxyethyl)-3-(1H-pyrazol-4-yl)-1H-pyrrolo[2,3-c]pyridin-5-yl)pyridin-4-yl)-5-(trifluoromethyl)-1,2,4-oxadiazole (obtained as hemiformate salt) 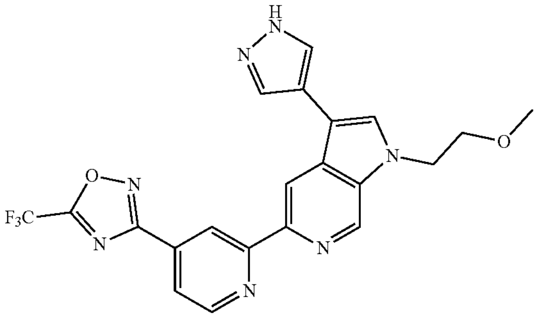 [SMILES: COCCn1cc(-c2cn[nH]c2)c2cc(-c3cc(-c4noc(C(F)(F)F)n4)ccn3)ncc21] | Reference example 19d | 18 | 4.27 | 456.1 (M + $H^+$) |
| 1at | 3-(2-(1-Methyl-1H-pyrrolo[2,3-c]pyridin-5-yl)pyridin-4-yl)-5-(trifluoromethyl)-1,2,4-oxadiazole (obtained as hemiformate hemitrifluoroacetate salt) 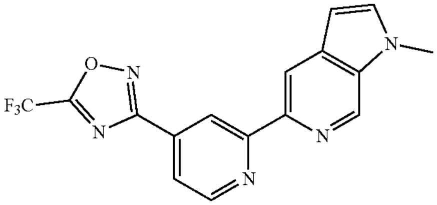 [SMILES: Cn1ccc2cc(-c3cc(-c4noc(C(F)(F)F)n4)ccn3)ncc21] | 5-Bromo-1-methyl-1H-pyrrolo[2,3-c]pyridine | 20 | 3.87 | 346.1 (M + $H^+$) |
| 1au | 3-(2-(1-(2-Methoxyethyl)-1H-pyrrolo[3,2-c]pyridin-6-yl)pyridin-4-yl)-5-(trifluoromethyl)-1,2,4-oxadiazole 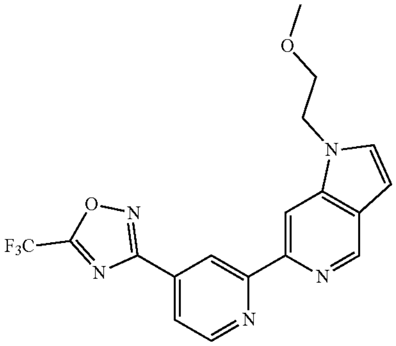 [SMILES: COCCn1ccc2cnc(-c3cc(-c4noc(C(F)(F)F)n4)ccn3)cc21] | Reference example 25a | 20 | 3.96 | 390.26 (M + $H^+$) |

-continued

| Example | Compound name | Starting material | HPLC method | $R_t$ (min) | m/z |
|---|---|---|---|---|---|
| 1av | 3-(2-(1-(Pyridin-3-ylmethyl)-1H-pyrrolo[3,2-c]pyridin-6-yl)pyridin-4-yl)-5-(trifluoromethyl)-1,2,4-oxadiazole | Reference example 25b | 18 | 3.75 | 423.1 (M + H$^+$) |
| | 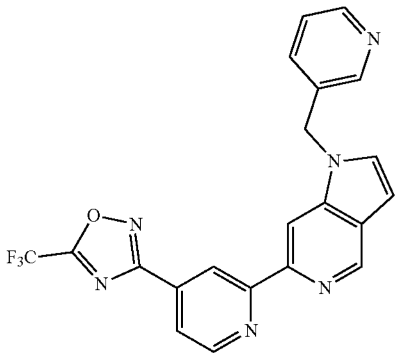 [SMILES: FC(F)(F)c1nc(-c2ccnc(-c3cc4c(ccn4Cc4cccnc4)cn3)c2)no1] | | | | |
| 1aw | 3-(2-(1-(Pyridin-2-ylmethyl)-1H-pyrrolo[3,2-c]pyridin-6-yl)pyridin-4-yl)-5-(trifluoromethyl)-1,2,4-oxadiazole | Reference example 25c | 18 | 3.75 | 423.1 (M + H$^+$) |
| | 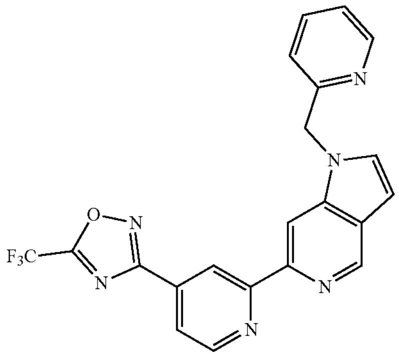 [SMILES: FC(F)(F)c1nc(-c2ccnc(-c3cc4c(ccn4Cc4ccccn4)cn3)c2)no1] | | | | |
| 1ax | 2-(Methyl(3-((4'-(5-(trifluoromethyl)-1,2,4-oxadiazol-3-yl)-[2,2'-bipyridin]-5-yl)oxy)propyl)amino)ethan-1-ol (obtained as formate salt) | Reference example 6c | 22 | 4.38 | 424.38 (M + H$^+$) |
| | 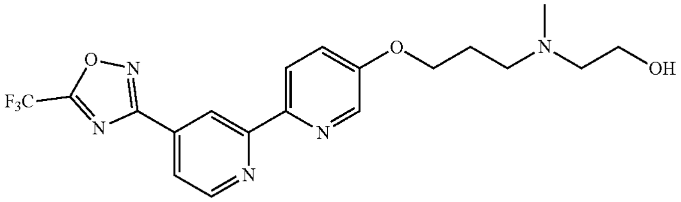 [SMILES: CN(CCO)CCCOc1ccc(-c2cc(-c3noc(C(F)(F)F)n3)ccn2)nc1] | | | | |
| 1ay | 3-(2-(1-(2-Methoxyethyl)-1H-pyrazolo[3,4-c]pyridin-5-yl)pyridin-4-yl)-5-(trifluoromethyl)-1,2,4-oxadiazole | Reference example 25d | 23 | 5.39 | 390.9 (M + H$^+$) |
| | 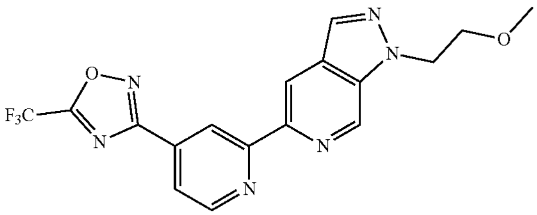 [SMILES: COCCn1ncc2cc(-c3cc(-c4noc(C(F)(F)F)n4)ccn3)ncc21] | | | | |

-continued

| Example | Compound name | Starting material | HPLC method | $R_t$ (min) | m/z |
|---|---|---|---|---|---|
| 1az | 3-(2-(2-(2-Methoxyethyl)-2H-pyrazolo[3,4-c]pyridin-5-yl)pyridin-4-yl)-5-(trifluoromethyl)-1,2,4-oxadiazole | Reference example 25e | 20 | 4.50 | 391.18 (M + H$^+$) |
| | 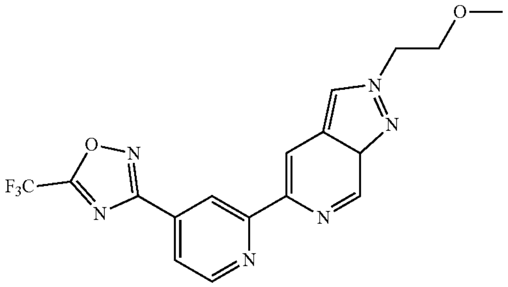 | | | | |
| 1aaa | 3-(2-(1-(2-Methoxyethyl)-1H-pyrazolo[4,3-b]pyridin-3-yl)pyridin-4-yl)-5-(trifluoromethyl)-1,2,4-oxadiazole | Reference example 32 | 27 | 4.65 | 391.27 (M + H$^+$) |
| | 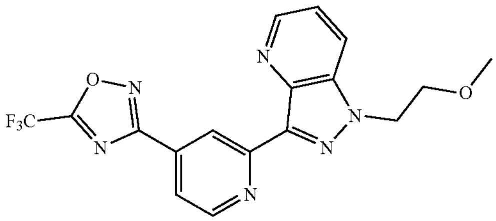 [SMILES: COCCn1nc(-c2cc(-c3noc(C(F)(F)F)n3)ccn2)c2ncccc21] | | | | |
| 1aab | 3-(2-(1-Ethyl-1H-pyrazolo[4,3-b]pyridin-3-yl)pyridin-4-yl)-5-(trifluoromethyl)-1,2,4-oxadiazole | Reference example 32a | 27 | 4.83 | 361.24 (M + H$^+$) |
| | 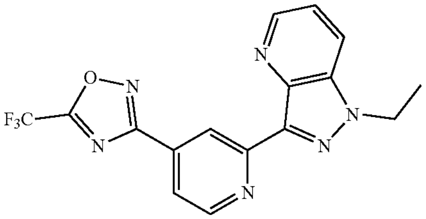 [SMILES: CCn1nc(-c2cc(-c3noc(C(F)(F)F)n3)ccn2)c2ncccc21] | | | | |
| 1aac | 3-(2-(1-(2-(1-Methyl-1H-imidazol-2-yl)ethyl)-1H-pyrazolo[4,3-b]pyridin-3-yl]pyridin-4-yl)-5-(trifluoromethyl)-1,2,3-oxadiazole | Reference example 33 | 27 | 4.27 | 441.25 (M + H$^+$) |
| | 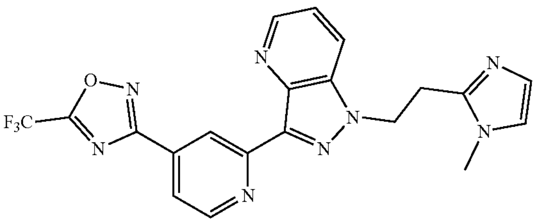 [SMILES: Cn1ccnc1CCn1nc(-c2cc(-c3noc(C(F)(F)F)n3)ccn2)c2ncccc21] | | | | |

-continued

| Example | Compound name | Starting material | HPLC method | $R_t$ (min) | m/z |
|---|---|---|---|---|---|
| 1aad | 3-(2-(1-((1-Methyl-1H-pyrazol-4-yl)methyl)-1H-pyrrolo[3,2-c]pyridin-6-yl)pyridin-4-yl)-5-(trifluoromethyl)-1,2,4-oxadiazole | Reference example 25f | 6 | 1.74 | 426.31 ($M + H^+$) |
| | 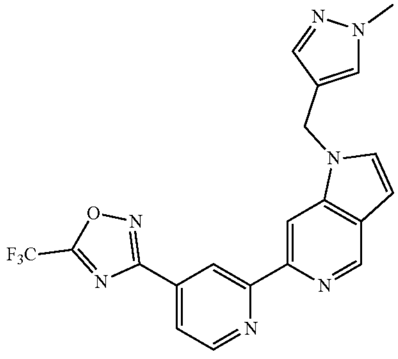 [SMILES: Cn1cc(Cn2ccc3cnc(-c4cc(-c5noc(C(F)(F)F)n5)ccn4)cc32)cn1] | | | | |

(*) TFA was added for complete Boc deprotection (**) obtained with 0.7 equiv of TFA and 0.3 equiv of formic acid

Example 2

N-Methyl-3-((4'-(5-(trifluoromethyl)-1,2,4-oxadiazol-3-yl)-[2,2'-bipyridin]-5-yl)oxy)propan-1-amine (as Formate Salt)

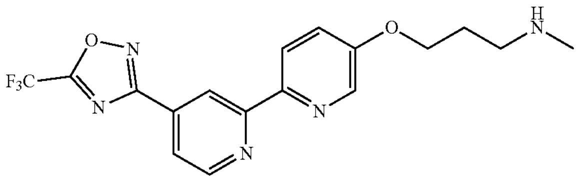 [SMILES: CNCCCOc1ccc(-c2cc(-c3noc(C(F)(F)F)n3)ccn2)nc1]

Step a. 5'-(3-(Methylamino)propoxy)-[2,2'-bipyridine]-4-carbonitrile

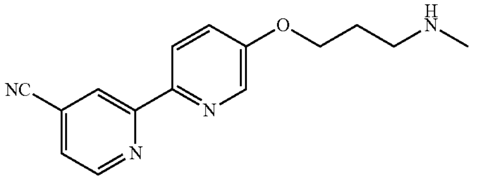 [SMILES: CNCCCOc1ccc(-c2cc(C#N)ccn2)nc1]

To a stirred solution of reference example 13 (250 mg, 1.01 mmol) in 1, 4-dioxane (20 mL), reference example 1 (16) (299 mg, 1.12 mmol), CsF (308 mg, 2.03 mmol) and CuI (38 mg, 0.20 mmol) wee added. The resulting solution was degassed with nitrogen for 15 minutes, then $Pd(PPh_3)_4$ (117 mg, 0.1 mmol) was added and heated at 110° C. for 16 h. The reaction was filtered through celite pad, washed with EtOAc (50 mL). The filtrated solution was evaporated to dryness. The crude residue was purified by column chromatography on 230-400 silica with 90% EtOAc/pet ether as eluent to afford the title compound (180 mg, 65%) as a gummy solid.

LC-MS (method 14): $R_t$=1.45 min; m/z=269.1 ($M+H^+$).

Step b. Tert-butyl (3-((4'-cyano-[2,2'-bipyridin]-5-yl)oxy)propyl)(methyl) carbamate

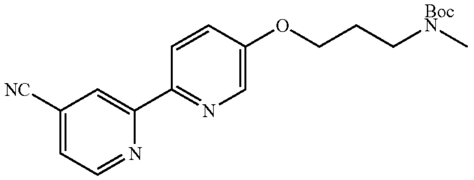 [SMILES: CN(CCCOc1ccc(-c2cc(C#N)ccn2)nc1)C(=O)OC(C)(C)C]

To a stirred solution of the compound obtained in the previous section, step a (180 mg, 0.67 mmol) in acetonitrile (10 mL), Boc anhydride (219 mg, 1.0 mmol), and TEA (0.27 mL, 2.01 mmol), were added. The resulting mixture was stirred rt for 16 h. The reaction mixture was evaporated under vacuum to afford a crude compound that was used for the next step without any further purification (200 mg, 80%)

LC-MS (method 15): $R_t$=3.75 min; m/z=369.08 ($M+H^+$).

Step c. Tert-butyl (3-((4'-(N-hydroxycarbamimidoyl)-[2,2'-bipyridin]-5-yl)oxy)propyl)(methyl) carbamate

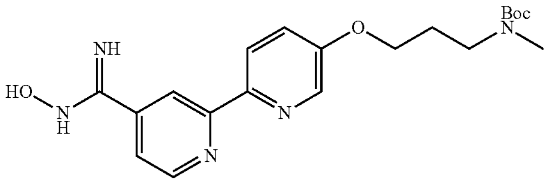 [SMILES: CN(CCCOc1ccc(-c2cc(C(=N)NO)ccn2)nc1)C(=O)OC(C)(C)C]

To a stirred solution of the compound obtained in the previous section, step b (200 mg, 0.54 mmol) in EtOH/MeOH (4:1), 50% $NH_2OH{\cdot}HCl$ aqueous solution (75 mg, 1.08 mmol) and $NaHCO_3$ (91 mg, 1.08 mmol) were added. The resulting mixture was stirred at 50° C. for 3 h. The reaction mixture was concentrated to get a crude residue that was diluted with EtOH and filtered thorough a Buckner funnel. The filtered solution was concentrated to dryness to afford the title compound (170 mg (78%) as a light brown gummy solid that was used in the next step without purification.

LC-MS (method 15): $R_t$=2.89 min; m/z=402.21 (M+H$^+$).

Step d. N-Methyl-3-((4'-(5-(trifluoromethyl)-1,2,4-oxadiazol-3-yl)-[2,2'-bipyridin]-5-yl)oxy) propan-1-amine Formate

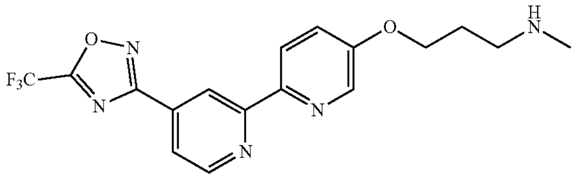 [SMILES: CNCCCOc1ccc(-c2cc(-c3noc(C(F)(F)F)n3)ccn2)nc1]

To a stirred solution of the compound obtained in the previous section, step c (150 mg, 0.37 mmol) in THF trifluroacetic anhydride (0.1 mL, 0.56 mmol) was added. The resulting mixture was heated at 70° C. and TFA (0.5 mL, 0.64 mmol) was added. It was stirred at 50° C. for 2 h. The solvents were evaporated under vacuum and the crude residue was poured in to ice water and extracted with EtOAc. The organic layer was dried over anhydrous $Na_2SO_4$, filtered and concentrated. The crude compound was purified by prep HPLC to afford the title compound (65 mg, 45%) as a pink solid.

LC-MS (method 15): $R_t$=2.79 min; m/z=380.15 (M+H$^+$).

Prep.HPLC conditions: Column/dimensions: SYNERGY POLAR C18(21.2×250 mm), 5 μm Mobile phase 0.1% FA: Acetonitrile (A:B) Gradient (Time/% B): 0/20, 1/20, 7/50, 10/50, 10.1/98, 13/98, 13.120, 16/20. Flow rate: 20 ml/min.

Example 3

1-(1-Butyl-5-(4-(5-(trifluoromethyl)-1,2,4-oxadiazol-3-yl)pyridin-2-yl)-1-pyrrolo[2,3-c]pyridin-3-yl)-N,N-dimethylmethanamine

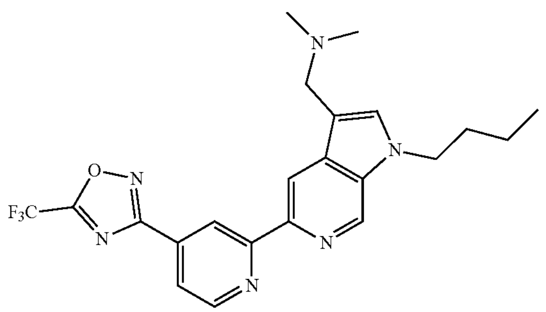 [SMILES: CCCCn1cc(CN(C)C)c2cc(-c3cc(-c4noc(C(F)(F)F)n4)ccn3)ncc21]

To a stirred solution of example 1 (400 mg, 1 mmol) in n-butanol, HCHO (300 mg, 10 mmol) and dimethyl amine HCl salt (815 mg 10 mmol) were added. The resulting mixture was stirred at 120° C. for 16 h. The reaction mixture concentrated to get a crude compound that was purified by prep-HPLC to afford the title compound (38 mg, 8.6%) as a pink sticky solid.

LC-MS (method 15): $R_t$=3.37 min; m/z=445.39 (M+H$^+$).

Preparative HPLC Conditions: Column/dimensions: XSELECT C18 (19*250*5 μm) Mobile phase A: 0.1% FA in water (aq) Mobile phase B: Acetonitrile (org) Gradient (Time/% B) 0/10, 1/10, 5/30, 9/30, 9.1/100, 11/100, 11.1/10, 13/10. Flow rate: 18 ml/min Solubility: Methanol+THF.

Example 4

3-(2-(1H-Pyrazolo[4,3-b]pyridin-3-yl)pyridin-4-yl)-5-(trifluoromethyl)-1,2,4-oxadiazole

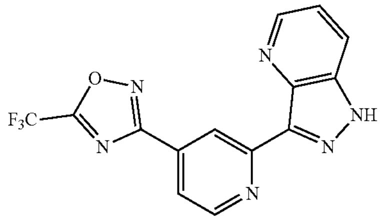 [SMILES: FC(F)(F)c1nc(-c2ccnc(-c3n[nH]c4cccnc34)c2)no1]

Step a. 2-(1-(Tetrahydro-2H-pyran-2-yl)-1H-pyrazolo[4,3-b]pyridin-3-yl)isonicotinonitrile

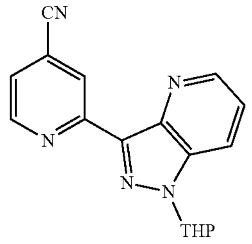

To a stirred solution of reference example 26 (900 mg, 3.19 mmol) in toluene (25 mL), reference example 1 (1100 mg, 4.15 mmol) was added and degassed for 10 min with nitrogen gas. Then, $PdCl_2(PPh_3)_2$ (112 mg, 0.16 mmol) was added and the resulting solution was degassed for another 5 min and heated at 100° C. for 16 h. The reaction mixture was concentrated under reduced pressure to afford a crude residue that was purified by column chromatography to afford the title compound (800 mg, 82.2%).

LC-MS (method 1): $R_t$=2.44 min; m/z=306.24 (M+H$^+$).

Step b. 2-(1H-Pyrazolo[4,3-b]pyridin-3-yl)isonicotinonitrile

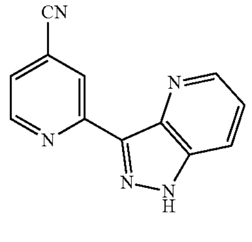 [SMILES: N#Cc1ccnc(-c2n[nH]c3cccnc23)c1]

To a stirred solution of the compound obtained in the previous section, step a (800 mg, 2.62 mmol) in DCM (15 mL), TFA (10 mL) was added and it was stirred at rt for 48 h. The reaction mixture was concentrated under reduced pressure to afford a crude residue that was purified by column chromatography to afford the title compound (400 mg, 69.0%).

LC-MS (method 1): $R_t$=1.85 min; m/z=222.13 ($M+H^+$).

Step c. N-hydroxy-2-(1H-pyrazolo[4,3-b]pyridin-3-yl)isonicotinamidoxime

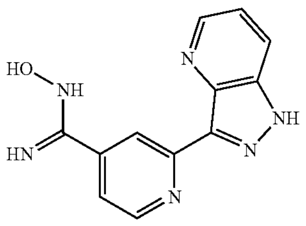 [SMILES: N=C(NO)c1ccnc(-c2n[nH]c3cccnc23)c1]

Following a similar procedure to that described in example 1, section b, but using the compound obtained in the previous section, step b, instead of 2-(1-butyl-1H-pyrrolo[2,3-c]pyridin-5-yl)isonicotinonitrile, the desired compound was obtained.

LC-MS (method 14): $R_t$=1.25 min; m/z=255.1 ($M+H^+$).

Step d. 3-(2-(1H-pyrazolo[4,3-b]pyridin-3-yl)pyridin-4-yl)-5-(trifluoromethyl)-1,2,4-oxadiazole

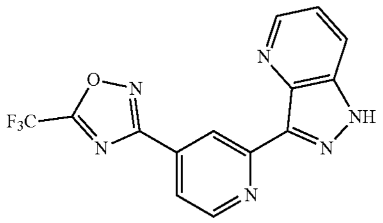 [SMILES: FC(F)(F)c1nc(-c2ccnc(-c3n[nH]c4cccnc34)c2)no1]

Following a similar procedure to that described in example 1, section c, but using the compound obtained in the previous section, step c, instead of 2-(1-butyl-1H-pyrrolo[2,3-c]pyridin-5-yl)-N-hydroxyisonicotinimidamide, the desired compound was obtained.

LC-MS (method 6): $R_t$=1.98 min; m/z=333.20 ($M+H^+$).

Example 5

N-(4'-(5-(trifluoromethyl)-1,2,4-oxadiazol-3-yl)-[2,2'-bipyridin]-4-yl)piperidine-3-carboxamide (as Hemiformate Salt)

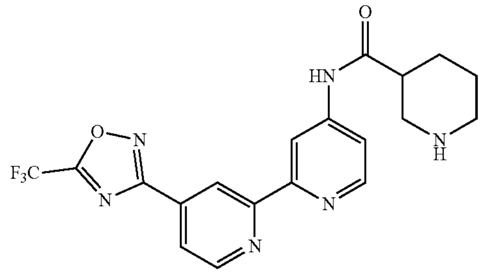 [SMILES: O=C(Nc1ccnc(-c2cc(-c3noc(C(F)(F)F)n3)ccn2)c1)C1CCCNC1]

Step a. tert-butyl 3-((4'-cyano-[2,2'-bipyridin]-4-yl)carbamoyl)piperidine-1-carboxylate

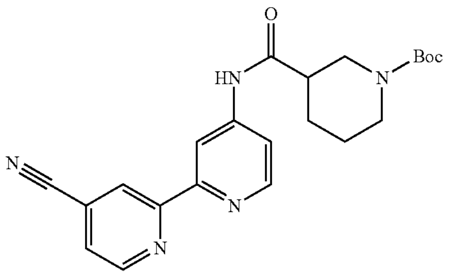 [SMILES: CC(C)(C)OC(=O)N1CCCC(C(=O)Nc2ccnc(-c3cc(C#N)ccn3)c2)C1]

To a stirred solution of reference example 16c (3 g, 7.81 mmol) in toluene (30 mL), 2-bromoisonicotinonitrile (2.14 g, 11.71 mmol), and hexamethylditin (2.8 mL, 13.67 mmol) were added. The resulting solution was degassed with argon for 10 minutes, then $Pd(PPh_3)_4$ (902 mg, 0.781 mmol) was added. The resulting mixture was degassed for 5 minutes and heated at 110° C. for 16 h. The reaction mixture was diluted with water and extracted with EtOAc (2×20 mL). The organic layer was dried over anhydrous $Na_2SO_4$ and concentrated under reduced pressure to get a crude residue that was purified by column chromatography using 10% EtOAc in petroleum ether to afford the title compound (800 mg, 25.1%) LC-MS (method 1): $R_t$=2.62 min; m/z=408.31 ($M+H^+$).

Step b. N-(4'-cyano-[2,2'-bipyridin]-4-yl)piperidine-3-carboxamide hydrochloride

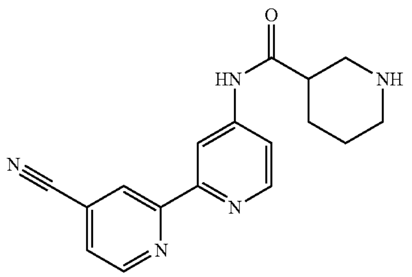 [SMILES: N#Cc1ccnc(-c2cc(NC(=O)C3CCCNC3)ccn2)c1]

To a stirred solution of the compound obtained in the previous section, step a, (200 mg, 0.486 mmol) in DCM (2 mL), 2M HCl solution in diethylether (3 mL) was added at 0° C. The reaction mixture was allowed to stir at rt for 2 h. The resulting mixture was concentrated and the crude residue was triturated with n-pentane and diethyl ether. It was filtered under reduced pressure to afford 800 mg (54%) of the title compound LC-MS (method 1): $R_t$=1.54 min; m/z=308.29 (M+H$^+$).

Step c. N-(4'-(N-hydroxycarbamimidoyl)-[2,2'-bipyridin]-4-yl)piperidine-3-carboxamide hydrochloride

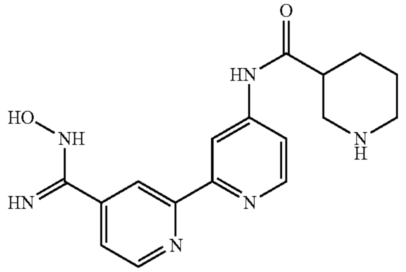 [SMILES: N=C(NO)c1ccnc(-c2cc(NC(=O)C3CCCNC3)ccn2)c1]

To a stirred solution of the compound obtained in the previous section, step b, (50 mg, 0.16 mmol) in EtOH (6 mL), hydroxylamine hydrochloride (22 mg, 0.32 mmol), and $NaHCO_3$ (27 mg, 0.32 mmol) in water (2 mL) were added. The reaction mixture was stirred at 70° C. for 6 h. The resulting solution was concentrated to dryness and the crude residue was diluted with EtOH and filtered thorough a Buckner funnel to remove the $NaHCO_3$. The filtered solution was concentrated to afford the title compound (45 mg, 82%) that was used in next step without further purification.

LC-MS (method 14): $R_t$=1.26 min; m/z=341.1 (M+H$^+$).

Step d. 1-(2,2,2-trifluoroacetyl)-N-(4'-(5-(trifluoromethyl)-1,2,4-oxadiazol-3-yl)-[2,2'-bipyridin]-4-yl)piperidine-3-carboxamide

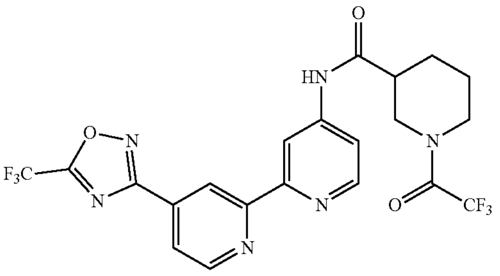 [SMILES: O=C(Nc1ccnc(-c2cc(-c3noc(C(F)(F)F)n3)ccn2)c1)C1CCCN(C(=O)C(F)(F)F)C1]

To a stirred solution of the compound obtained in the previous section, step c, (40 mg, 0.11 mmol) in THF (5 mL), trifluroacetic anhydride (0.1 mL) was added. The resulting mixture was stirred at 70° C. for 3 h. The reaction mixture was concentrated under reduced pressure to get a crude residue that was purified by Prep HPLC to afford the title compound (16 mg, 28%) as an off white solid.

LC-MS (method 14): $R_t$=2.82 min; m/z=515.1 (M+H$^+$).

Preparative HPLC Conditions: Column/dimensions Prontosil C18 (20×250 mm), 10 μm Mobile phase: 0.1% Ammonium Acetate in water: Acetonitrile (A:B) Gradient (Time/% B): 0/20, 1/20, 5/70, 15/700, 15.1/100 Flow rate: 20 ml/miN Solubility: ACN+THF+WATER Step e. N-(4'-(5-(trifluoromethyl)-1,2,4-oxadiazol-3-yl)-[2,2'-bipyridin]-4-yl)piperidine-3-carboxamide Hemiformate

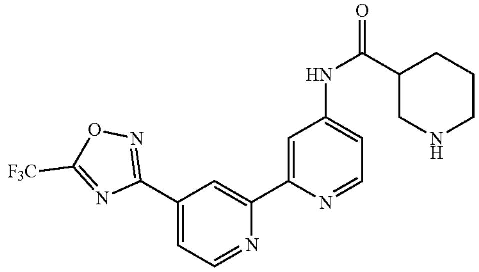 [SMILES: O=C(Nc1ccnc(-c2cc(-c3noc(C(F)(F)F)n3)ccn2)c1)C1CCCNC1]

To a stirred solution of the compound obtained in the previous section, step c, (16 mg, 0.03 mmol) in MeOH (5 ML), $K_2CO_3$ (4.7 mg, 0.034 mmol) were added. The resulting mixture was stirred at rt for 16 h. The reaction mixture was concentrated under reduced to get a crude residue that was purified by Prep HPLC to afford the title compound (6 mg, 46%) as an off white solid.

LC-MS (method 6): $R_t$=1.84 min; m/z=419.34 (M+H$^+$).

Preparative HPLC Conditions: Column/dimensions: SUN FIRE C18 (19*150 mm, 5 um) Mobile phase A: 0.1% FA in water (aq) Mobile phase B: Acetonitrile (org) Gradient (Time/% B): 0/10, 1/10, 5/25, 8/25, 8.1/98, 10/98, 10.1/10, 12/10. Flow rate: 18 ml/min Solubility:Acetonitrile+THF Example 6

3-(2-(1H-Pyrazolo[3,4-b]pyridin-1-yl)pyridin-4-yl)-5-(trifluoromethyl)-1,2,4-oxadiazole

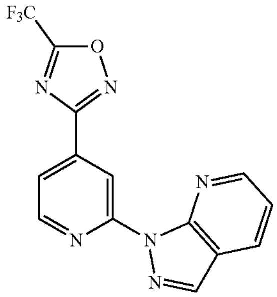 [SMILES: FC(F)(F)c1nc(-c2ccnc(-n3ncc4cccnc43)c2)no1]

Step a. 2-(1H-pyrazolo[3,4-b]pyridin-1-yl)isonicotinonitrile

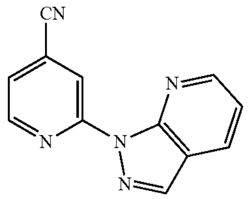 [SMILES: N#Cc1ccnc(-n2ncc3cccnc32)c1]

To a stirred solution of 2-bromoisonicotinonitrile (500 mg, 2.7 mmol) in toluene (25 mL), 1H-pyrazolo[3,4-b]pyridine (0.6432 g, 5.4 mmol), and $K_2CO_3$ (1.86 g, 13.5 mmol) were added followed by CuI (0.256 g, 1.35 mmol). The resulting solution was degassed with nitrogen for 15 minutes, and trans N,N-dimethylcyclohexane-1,2-diamine (0.192 g, 1.35 mmol) was added. The resulting reaction was heated at 110° C. for 16 h. The reaction mixture was evaporated under vacuum to get a crude residue that was purified by prep HPLC to afford the title compound (300 mg, 29.3%)

LC-MS (method 6): $R_t$=1.626 min; m/z=222.01 (M+H$^+$).

Step b. N-hydroxy-2-(1H-pyrazolo[3,4-b]pyridin-1-yl)isonicotinamidoxime

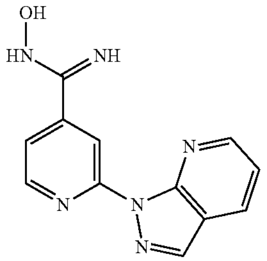 [SMILES: N=C(NO)c1ccnc(-n2ncc3cccnc32)c1]

To a stirred solution the compound obtained in the previous section, step a (300 mg, 1.0 mmol) in EtOH (5 mL), 50% $NH_2OH \cdot HCl$ aqueous solution (179 mg, 2.1 mmol) and $Na_2CO_3$ (296 mg, 2.8 mmol) in $H_2O$ (5 mL) were added. The resulting solution was stirred at rt for 18 h. The reaction mixture was evaporated under vacuum, to get a crude compound that was used for the next step without any further purification.

LC-MS (method 6): $R_t$=1.16 min; m/z=255.12 (M+H$^+$).

Step c. 3-(2-(1H-Pyrazolo[3,4-b]pyridin-1-yl)pyridin-4-yl)-5-(trifluoromethyl)-1,2,4-oxadiazole

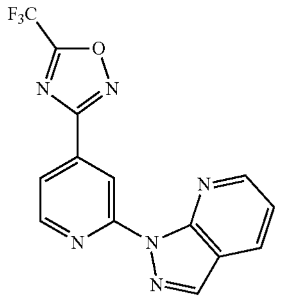 [SMILES: FC(F)(F)c1nc(-c2ccnc(-n3ncc4cccnc43)c2)no1]

To a stirred solution the compound obtained in the previous section, step b (300 mg, 1.2 mmol) in THF (10 mL), trifluroacetic anhydride (252 mg, 1.2 mmol) was added. The resulting solution was heated at 70° C. for 3 h. The reaction mixture was evaporated under vacuum to get a crude residue that was purified by prep HPLC to afford the title compound (115 mg, 29.3%) as an off white solid.

LC-MS (method 20): $R_t$=4.79 min; m/z=333.11 (M+H$^+$).

Example 7

N,N-Dimethyl-3-((4'-(5-(trifluoromethyl)-1,2,4-oxadiazol-3-yl)-[2,2'-bipyridin]-5-yl)oxy)propan-1-amine

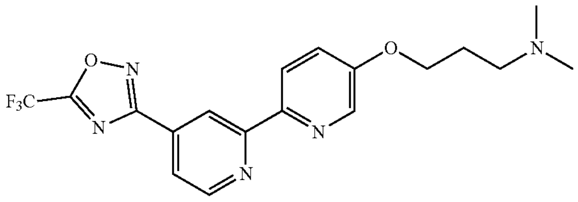 [SMILES: CN(C)CCCOc1ccc(-c2cc(-c3noc(C(F)(F)F)n3)ccn2)nc1]

To a stirred solution of reference example 31 (300 mg, 1.0 mmol) in toluene (3 mL), reference example 30 (928 mg, 3.47 mmolv) was added. The resulting solution was degassed with nitrogen for 15 minutes, and then Pd $(PPh_3)_4$ (115 mg, 0.1 mmol) was added. The reaction mixture was again degassed for another 5 min, and then heated at 110° C., for 16 h. The crude reaction was filtered through a celite pad, washed with EtOAc (50 mL), and the filtrated solution was evaporated to dryness. The crude compound was purified by prep HPLC to afford the title compound (65 mg, 16%) as a light pink solid.

LC-MS (method 16): $R_t$=4.49 min; m/z=394.29 (M+H$^+$).

Following a similar procedure to that described in example 7, but using the corresponding starting material, the following compound was obtained:

| Example | Compound name | Starting material | HPLC method | $R_t$ (min) | m/z |
|---|---|---|---|---|---|
| 7a | 3-(2-(1-Methyl-1H-pyrazolo[4,3-b]pyridin-3-yl)pyridin-4-yl)-5-(trifluoromethyl)-1,2,4-oxadiazole | Reference example 34 | 27 | 4.60 | 347.30 $(M + H^+)$ |

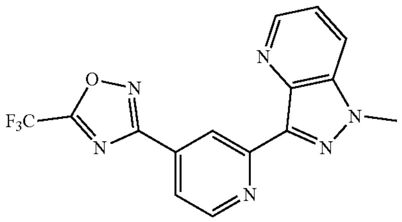 [SMILES: Cn1nc(-c2cc(-c3noc(C(F)(F)F)n3)ccn2)c2ncccc21]

Example 8

HDAC6 and HDAC2 Enzyme Inhibition Assay

Method:

A fluorimetric assay was used for testing the activity of compounds of the invention against HDAC6 and HDAC2. Recombinant proteins reference and amounts used in each assay are listed in the Table below.

| Assay | Reference | ng/reaction |
|---|---|---|
| HDAC2 | BPS Bioscience Inc. #50002 (full length with C-terminal His-tag) | 7.5 |
| HDAC6 | BPS Bioscience Inc. #50006 (full length with N-terminal GST-tag) | 20 |

The compounds were dissolved in DMSO. Serial dilutions were prepared in DMSO and then diluted 1:10 in HDAC assay buffer (Tris-buffered solution, BPS Bioscience Inc. #50031). 5 μl of the compound dilution was added to a 50 μl reaction so that the final concentration of DMSO was 1%.

The compounds were pre-incubated in duplicate at RT for 3 hours in a mixture containing HDAC assay buffer, 5 μg BSA and recombinant HDAC enzyme (see table above). The enzymatic reactions were initiated by the addition of a fluorogenic, acetylated peptide substrate based on a histone protein (BPS Bioscience Inc. #50037) to a final concentration of 10 μM. The enzymatic reaction proceeded for 30 minutes at 37° C. Then, 50 μl of 2× HDAC Developer, which contains peptidase activity and Trichostatin A (BPS Bioscience Inc. #50030) was added and the plate was incubated at RT for an additional 15 minutes. Fluorescence intensity was measured at an excitation of 360 nm and an emission of 460 nm using a Tecan Infinite M1000 microplate reader.

Trichostatin A (TSA, Selleckchem #S1045) was used as reference inhibitor.

The fluorescent intensity data were analyzed using the computer software Graphpad Prism (GraphPad Software, San Diego, CA). 100% activity was defined as the fluorescent intensity (Ft) in the absence of the compound. 0% activity was defined as the fluorescent intensity (Fb) in the absence of the enzyme. The percent activity in the presence of each compound was calculated according to the following equation: % activity=(F−Fb)/(Ft−Fb), where F=the fluorescent intensity in the presence of the compound.

Results:

The results obtained in the above assays with compounds of the invention are shown in the table below:

| Example # | HDAC6 % inh @ 1 μM | HDAC2 % inh @ 1 μM |
|---|---|---|
| 1 | 79 | NT |
| 1a | NT | NT |
| 1b | 84 | NT |
| 1c | 89 | 3 |
| 1d | 78 | NT |
| 1e | 84 | 9 |
| 1f | 71 | 16 |
| 1g | 96 | 38 |
| 1h | 96 | NT |
| 1i | NT | NT |
| 1j | 69 | 10 |
| 1k | 95 | 27 |
| 1l | NT | NT |
| 1m | 81 | NT |
| 1n | NT | NT |
| 1o | 97 | 23 |
| 1p | NT | NT |
| 1q | 73 | 11 |
| 1r | 92 | NT |
| 1s | NT | NT |
| 1t | 88 | NT |
| 1u | 98 | 19 |
| 1v | 66 | 3 |
| 1w | 86 | 6 |
| 1x | 95 | 16 |
| 1y | 92 | 27 |
| 1z | 97 | 46 |
| 1aa | 92 | NT |
| 1ab | 93 | 38 |
| 1ac | 78 | 18 |
| 1ad | NT | NT |
| 1ae | 85 | 5 |
| 1af | NT | NT |
| 1ag | NT | NT |
| 1ah | 96 | 35 |
| 1ai | NT | NT |
| 1aj | NT | NT |
| 1ak | 90 | 14 |
| 1al | 92 | 31 |
| 1am | NT | NT |
| 1an | NT | NT |
| 1ao | NT | NT |
| 1ap | 86 | 6 |
| 1aq | 89 | 2 |
| 1ar | NT | NT |
| 1as | NT | NT |
| 1at | NT | NT |
| 1au | 85 | 19 |
| 1av | NT | NT |
| 1aw | 81 | 15 |
| 1ax | NT | NT |
| 1ay | NT | NT |
| 1az | NT | NT |
| 2 | NT | NT |
| 3 | 90 | 30 |

-continued

| Example # | HDAC6 % inh @ 1 μM | HDAC2 % inh @ 1 μM |
|---|---|---|
| 4 | 96 | 25 |
| 5 | 95 | 29 |
| 6 | NT | NT |
| 7 | NT | NT |

NT: Not tested

Example 9

In Vitro Cell-Based Assay

Method:

In order to determine the cellular activity of HDAC6 upon treatment with HDAC6 inhibitors, acetylation levels of Alpha-Tubulin (a HDAC6-specific substrate) were measured by Western Blot. For this, MOLP8 cells were seeded in 6-well plates at a cell density of 500.000 cells/well and treated with the selected compounds at 5 and 1 μM for 18 h at 37° C. and 5% $CO_2$ in a humidified tissue culture incubator. Consecutively, cell pellets were collected and whole protein extracts prepared using RIPA buffer (SIGMA) supplemented with 1× protease inhibitors (cOmplete mini, Roche). Protein concentration was determined with Bradford's reagent (Bio-Rad) as per manufacturer's instructions, and 7 μg of total protein were loaded into pre-cast 10% NuPAGE Novex gels (Life Technologies). Gels were run in MOPS-SOS buffer (Life Technologies) and proteins were transferred using the iBlot 2 Dry Blotting System (Life Technologies). Blots were subsequently rinsed in distilled water and stained with Ponceau S solution (SIGMA). Blots were then washed in distilled water to remove Ponceau excess and scanned with the Epson Perfection V600 Photo professional Scanner. After this, blots were de-stained and blocked in 5% milk/PBS-Tween 0.1% for 1 h at room temperature followed by incubation with anti-Acetyl-alpha Tubulin (SIGMA cat. #T7451, 1:10.000 dilution) and anti-Beta-actin (SIGMA, cat. #A5316, 1:2.000 dilution) primary antibodies in 5% milk/PBS-T 0.1%, overnight at 4° C. on a shaking platform. After incubation, blots were washed 3 times for 5 minutes each in PBS-Tween 0.5% and incubated with anti-mouse HRP-conjugated secondary antibody (Jackson Immuno Research, cat. #115-035-068) at 1:8.000 in 5% milk/PBS-Tween 0.1%, 1 h at room temperature on a shaking platform. After 3 washes of 5 minutes each with PBS-Tween 0.5% and 1 wash in PBS 1×, blots were developed with ECL Plus (GE Healthcare) and the chemiluminescent reaction imaged with the G:Box Chemi XRQ (Syngene) imaging system. WB and Ponceau images were analysed with ImageJ software, WB band intensities normalized by either total protein or Beta-actin content and made relative to ACY-1215 1 μM (equivalent to 100%). ACY-1215 is a HDAC6 inhibitor, and is also known as ricolinostat, with chemical name 2-(diphenylamino)-N-[7-(hydroxyamino)-7-oxoheptyl]-5-pyrimidinecarboxamide.

Percentage of band intensities was classified as follows:

| Relative band intensity (%) | Classification |
|---|---|
| <50 | − |
| 50-150 | + |
| 150-300 | ++ |
| >300 | +++ |

Results:

The results obtained in this assay with compounds of the invention are shown in the table below:

| Example | Cellular activity @1 uM | Cellular activity @5 uM |
|---|---|---|
| 1 | − | + |
| 1a | − | ++ |
| 1b | + | ++ |
| 1c | + | ++ |
| 1d | + | ++ |
| 1e | + | ++ |
| 1f | − | ++ |
| 1g | + | +++ |
| 1h | + | ++ |
| 1i | − | + |
| 1j | − | ++ |
| 1k | + | + |
| 1l | − | + |
| 1m | − | + |
| 1n | − | + |
| 1o | ++ | +++ |
| 1p | − | ++ |
| 1q | + | ++ |
| 1r | ++ | ++ |
| 1s | − | + |
| 1t | − | + |
| 1u | +++ | +++ |
| 1v | + | +++ |
| 1w | + | ++ |
| 1x | ++ | +++ |
| 1y | + | ++ |
| 1z | + | ++ |
| 1aa | + | + |
| 1ab | ++ | ++ |
| 1ac | + | ++ |
| 1ad | + | + |
| 1ae | + | + |
| 1af | + | + |
| 1ag | − | + |
| 1ah | + | ++ |
| 1ai | − | + |
| 1aj | + | + |
| 1ak | + | ++ |
| 1al | ++ | ++ |
| 1am | + | + |
| 1an | + | + |
| 1ao | + | ++ |
| 1ap | + | ++ |
| 1aq | ++ | ++ |
| 1ar | + | + |
| 1as | + | + |
| 1at | − | + |
| 1au | + | ++ |
| 1av | + | ++ |
| 1aw | + | ++ |
| 1ax | + | + |
| 1ay | − | + |
| 1az | − | + |
| 1aaa | + | + |
| 1aab | + | + |
| 1aac | + | ++ |
| 1aad | + | ++ |
| 2 | − | + |
| 3 | + | +++ |
| 4 | ++ | +++ |

-continued

| Example | Cellular activity @1 uM | Cellular activity @5 uM |
|---|---|---|
| 5 | ++ | ++ |
| 6 | + | + |
| 7 | − | + |
| 7a | + | ++ |

The data provided in Examples 8 and 9 show that compounds of Formula (I) exhibit potent HDAC6 inhibitory activity, including in cells. Furthermore, compounds of the invention show selectivity towards HDAC6 vs HDAC2, based on the data obtained for representative compounds of the invention against HDAC2, as shown in example 8.

The invention claimed is:

1. A compound of Formula (I) or a salt thereof:

(I)

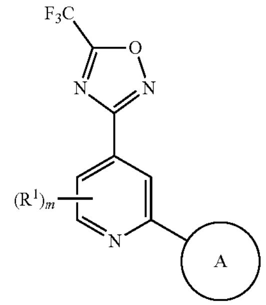

wherein m is 0, 1, or 2;

each $R^1$ is independently selected from halo, methyl, and trifluoromethyl;

A is selected from the cyclic groups listed below:

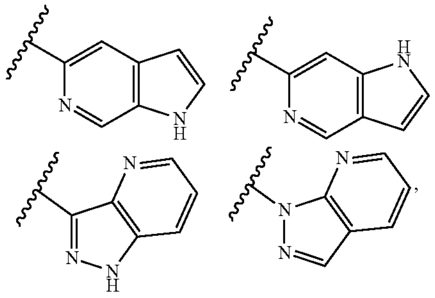

wherein A is optionally substituted with one or two $R^2$ and in addition A is optionally substituted with one $R^3$;

each $R^2$ is independently selected from halo, $C_{1-6}$ alkyl, $C_{1-6}$ haloalkyl, $C_{3-7}$ cycloalkyl, and —($C_{1-6}$ alkylene)-$OR^4$;

$R^3$ is selected from -$L^1$-$R^5$, -$L^2$-$OR^6$, -$L^3$-$NR^7R^8$, -$L^4$-$CONR^9R^{10}$, -$L^5$-$NR^{11}COR^{12}$, —Y-$L^6$-$OR^6$, and —Y-$L^7$-$NR^7R^8$;

$L^1$, $L^2$, $L^3$, $L^4$ and $L^5$ are each independently selected from a bond and $C_{1-6}$ alkylene;

$L^6$ and $L^7$ are each independently selected from $C_{2-6}$ alkylene;

each Y is independently selected from —O—, —$NR^{13}$—, —$CONR^{14}$—, and —$NR^{15}CO$—;

each $R^4$ is independently selected from hydrogen, $C_{1-6}$ alkyl, $C_{1-6}$ haloalkyl, $C_{3-7}$ cycloalkyl, and $C_{3-7}$ cycloalkyl-$C_{1-6}$ alkyl;

each $R^5$ is independently selected from carbocyclyl, aryl, heterocyclyl, and heteroaryl, wherein the carbocyclyl, the aryl, the heterocyclyl, and the heteroaryl are each optionally substituted with one or more $R^{16}$;

$R^6$ and $R^{12}$ are each independently selected from hydrogen, $C_{1-6}$ alkyl, $C_{1-6}$ haloalkyl, and -$L^1$-$R^5$;

$R^7$ and $R^8$ are each independently selected from hydrogen, $C_{1-6}$ alkyl, $C_{1-6}$ haloalkyl, —($C_{1-6}$ alkylene)-$OR^4$, and -$L^1$-$R^5$;

$R^9$ and $R^{10}$ are each independently selected from hydrogen, $C_{1-6}$ alkyl, $C_{1-6}$ haloalkyl, —($C_{1-6}$ alkylene)-$OR^4$, and -$L^1$-$R^5$, or $R^9$ and $R^{10}$ taken together with the N atom to which they are attached form a saturated 4- to 12-membered heterocyclic ring optionally containing one additional heteroatom selected from N, O, and S, wherein said heterocyclic ring is optionally substituted with one or more $R^{16}$;

$R^{11}$, $R^{13}$, $R^{14}$, and $R^{15}$ are each independently selected from hydrogen, $C_{1-6}$ alkyl, $C_{1-6}$ haloalkyl, $C_{3-7}$ cycloalkyl, $C_{3-7}$ cycloalkyl-$C_{1-6}$ alkyl, and —($C_{1-6}$ alkylene)-$OR^4$;

each $R^{16}$ is independently selected from $C_{1-6}$ alkyl, $C_{1-6}$ haloalkyl, halo, $C_{1-6}$ alkoxy, $C_{1-6}$ haloalkoxy, —OH, —$NR^{17}R^{18}$, —$COR^{19}$, —CN, -$L^8$-carbocyclyl, -$L^8$-aryl, -$L^8$-heterocyclyl, and -$L^8$-heteroaryl, wherein the carbocyclyl in -$L^8$-carbocyclyl, the aryl in -$L^8$-aryl, the heterocyclyl in -$L^8$-heterocyclyl, and the heteroaryl in -$L^8$-heteroaryl are each optionally substituted with one or more $R^{20}$;

each $L^8$ is independently selected from a bond and $C_{1-6}$ alkylene;

$R^{17}$ and $R^{18}$ are each independently selected from hydrogen, $C_{1-6}$ alkyl, $C_{1-6}$ haloalkyl, $C_{3-7}$ cycloalkyl, and $C_{3-7}$ cycloalkyl-$C_{1-6}$ alkyl;

$R^{19}$ is selected from hydrogen, $C_{1-6}$ alkyl, and $C_{1-6}$ haloalkyl; and each $R^{20}$ is independently selected from $C_{1-6}$ alkyl, $C_{1-6}$ haloalkyl, halo, $C_{1-6}$ alkoxy, $C_{1-6}$ haloalkoxy, —OH, —$NR^{17}R^{18}$, —$COR^{19}$, and —CN.

2. The compound of claim 1, wherein the compound has formula (IIIa) or (IIIb), or a salt thereof (IIIa)

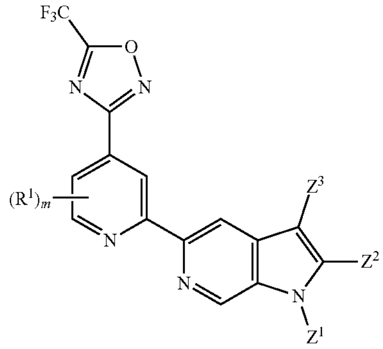

-continued (IIIb)

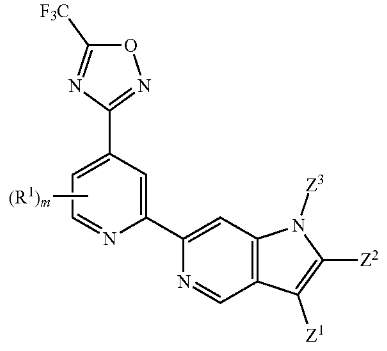

wherein one of $Z^1$, $Z^2$, and $Z^3$ is $R^3$ or H, and the others are independently selected from H and $R^2$.

3. The compound of claim 1, wherein the compound has formula (IVa), or a salt thereof (IVa)

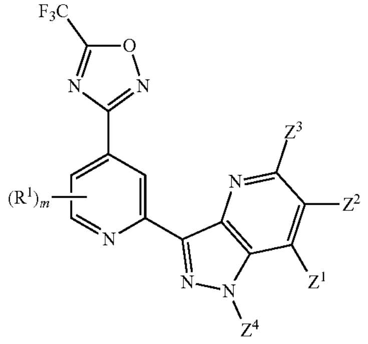

wherein one of $Z^1$, $Z^2$, $Z^3$, and $Z^4$ is selected from $R^2$, $R^3$, and H, and the others are independently selected from H and $R^2$, with the proviso that only up to two of $Z^1$, $Z^2$, $Z^3$, and $Z^4$ are $R^2$, or the compound has formula (IVb), or a salt thereof (IVb)

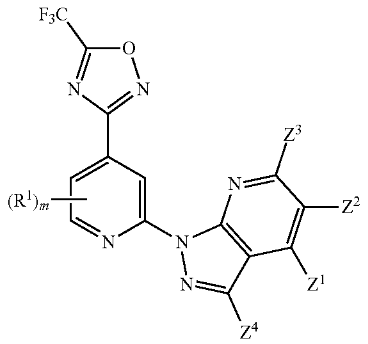

wherein one of $Z^1$, $Z^2$, $Z^3$, and $Z^4$ is selected from $R^2$, $R^3$, and H, and the others are independently selected from H and $R^2$, with the proviso that only up to two of $Z^1$, $Z^2$, $Z^3$ and $Z^4$ are $R^2$.

4. The compound of claim 1, wherein m is 0.

5. The compound of claim 1, wherein $R^3$ is selected from $-L^1-R^5$, $-L^2-OR^6$, $-L^3-NR^7R^8$, $—CONR^9R^{10}$, $—NR^{11}COR^{12}$, and $—Y-L^7-NR^7R^8$.

6. The compound of claim 1, wherein $R^3$ is $—CONR^9R^{10}$ or $—NR^{11}COR^{12}$.

7. The compound of claim 1, wherein each $R^2$ is independently selected from $C_{1-4}$ alkyl, $C_{1-4}$ haloalkyl, and $—(C_{1-4}$ alkylene)-$OR^4$.

8. The compound of claim 1, which is a compound selected from:

3-(2-(1-Butyl-1H-pyrrolo[2,3-c]pyridin-5-yl)pyridin-4-yl)-5-(trifluoromethyl)-1,2,4-oxadiazole, 3-(2-(1-Propyl-1H-pyrrolo[2,3-c]pyridin-5-yl)pyridin-4-yl)-5-(trifluoromethyl)-1,2,4-oxadiazole, 1-Butyl-N,N-dimethyl-5-(4-(5-(trifluoromethyl)-1,2,4-oxadiazol-3-yl)pyridin-2-yl)-1H-pyrrolo[2,3-c]pyridine-2-carboxamide, 1-Butyl-N-ethyl-5-(4-(5-(trifluoromethyl)-1,2,4-oxadiazol-3-yl)pyridin-2-yl)-1H-pyrrolo[2,3-c]pyridine-2-carboxamide, 3-(2-(3-(Piperidin-1-ylmethyl)-1-propyl-1H-pyrrolo[2,3-c]pyridin-5-yl)pyridin-4-yl)-5-(trifluoromethyl)-1,2,4-oxadiazole, 4-((1-Propyl-5-(4-(5-(trifluoromethyl)-1,2,4-oxadiazol-3-yl)pyridin-2-yl)-1H-pyrrolo[2,3-c]pyridin-3-yl) methyl) morpholine, 3-(2-(1-(Tetrahydro-2H-pyran-4-yl)-1H-pyrrolo[3,2-c] pyridin-6-yl)pyridin-4-yl)-5-(trifluoromethyl)-1,2,4-oxadiazole, 3-(2-(1-((Tetrahydro-2H-pyran-4-yl)methyl)-1H-pyrrolo [3,2-c]pyridin-6-yl)pyridin-4-yl)-5-(trifluoromethyl)-1,2,4-oxadiazole, N,N,1-Trimethyl-5-(4-(5-(trifluoromethyl)-1,2,4-oxadiazol-3-yl)pyridin-2-yl)-1H-pyrrolo[2,3-c]pyridine-2-carboxamide, 3-(2-(1-Propyl-3-(1H-pyrazol-4-yl)-1H-pyrrolo[2,3-c] pyridin-5-yl)pyridin-4-yl)-5-(trifluoromethyl)-1,2,4-oxadiazole, 1-Butyl-N,N-diethyl-5-(4-(5-(trifluoromethyl)-1,2,4-oxadiazol-3-yl)pyridin-2-yl)-1H-pyrrolo[2,3-c]pyridine-2-carboxamide, 3-(2-(1-(2-Methoxyethyl)-1H-pyrrolo[2,3-c]pyridin-5-yl) pyridin-4-yl)-5-(trifluoromethyl)-1,2,4-oxadiazole, 3-(2-(1-(2-(4,4-Difluoropiperidin-1-yl)ethyl)-1H-pyrrolo [3,2-c]pyridin-6-yl)pyridin-4-yl)-5-(trifluoromethyl)-1,2,4-oxadiazole, (1-Propyl-5-(4-(5-(trifluoromethyl)-1,2,4-oxadiazol-3-yl) pyridin-2-yl)-1H-pyrrolo[2,3-c]pyridin-3-yl)methanol, 3-(2-(3-(Methoxymethyl)-1-propyl-1H-pyrrolo[2,3-c] pyridin-5-yl)pyridin-4-yl)-5-(trifluoromethyl)-1,2,4-oxadiazole, (1-Butyl-5-(4-(5-(trifluoromethyl)-1,2,4-oxadiazol-3-yl) pyridin-2-yl)-1H-pyrrolo[2,3-c] pyridin-3-yl)methanol, 3-(2-(1H-Pyrrolo[3,2-c]pyridin-6-yl)pyridin-4-yl)-5-(trifluoromethyl)-1,2,4-oxadiazole, 3-(2-(1-(Pyridin-4-ylmethyl)-1H-pyrrolo[3,2-c]pyridin-6-yl)pyridin-4-yl)-5-(trifluoromethyl)-1,2,4-oxadiazole, 3-(2-(1-(1-(2,2,2-Trifluoroethyl)piperidin-4-yl)-1H-pyrrolo[3,2-c]pyridin-6-yl)pyridin-4-yl)-5-(trifluoromethyl)-1,2,4-oxadiazole, 3-(2-(1-Methyl-3-(1H-pyrazol-4-yl)-1H-pyrrolo[2,3-c] pyridin-5-yl)pyridin-4-yl)-5-(trifluoromethyl)-1,2,4-oxadiazole, 3-(2-(1-Butyl-3-(1-methyl-1,2,3,6-tetrahydropyridin-4-yl)-1H-pyrrolo[2,3-c]pyridin-5-yl)pyridin-4-yl)-5-(trifluoromethyl)-1,2,4-oxadiazole, 1-(1-Butyl-5-(4-(5-(trifluoromethyl)-1,2,4-oxadiazol-3-yl)pyridin-2-yl)-1H-pyrrolo[2,3-c]pyridin-3-yl)-N,N-dimethylmethanamine, 3-(2-(1H-Pyrazolo[4,3-b]pyridin-3-yl)pyridin-4-yl)-5-(trifluoromethyl)-1,2,4-oxadiazole, 1-(2-Methoxyethyl)-N,N-dimethyl-5-(4-(5-(trifluoromethyl)-1,2,4-oxadiazol-3-yl)pyridin-2-yl)-1H-pyrrolo[2,3-c]pyridine-2-carboxamide, 3-(2-(1-(2-Methoxyethyl)-3-(1H-pyrazol-4-yl)-1H-pyrrolo[2,3-c]pyridin-5-yl)pyridin-4-yl)-5-(trifluoromethyl)-1,2,4-oxadiazole, 3-(2-(1-Methyl-1H-pyrrolo[2,3-c]pyridin-5-yl)pyridin-4-yl)-5-(trifluoromethyl)-1,2,4-oxadiazole, 3-(2-(1-(2-Methoxyethyl)-1H-pyrrolo[3,2-c]pyridin-6-yl)pyridin-4-yl)-5-(trifluoromethyl)-1,2,4-oxadiazole, 3-(2-(1-(Pyridin-3-ylmethyl)-1H-pyrrolo[3,2-c]pyridin-6-yl)pyridin-4-yl)-5-(trifluoromethyl)-1,2,4-oxadiazole, 3-(2-(1-(Pyridin-2-ylmethyl)-1H-pyrrolo[3,2-c]pyridin-6-yl)pyridin-4-yl)-5-(trifluoromethyl)-1,2,4-oxadiazole, 3-(2-(1H-Pyrazolo[3,4-b]pyridin-1-yl)pyridin-4-yl)-5-(trifluoromethyl)-1,2,4-oxadiazole, 3-(2-(1-Methyl-1H-pyrazolo[4,3-b]pyridin-3-yl)pyridin-4-yl)-5-(trifluoromethyl)-1,2,4-oxadiazole, 3-(2-(1-(2-Methoxyethyl)-1H-pyrazolo[4,3-b]pyridin-3-yl)pyridin-4-yl)-5-(trifluoromethyl)-1,2,4-oxadiazole, 3-(2-(1-Ethyl-1H-pyrazolo[4,3-b]pyridin-3-yl)pyridin-4-yl)-5-(trifluoromethyl)-1,2,4-oxadiazole, 3-(2-(1-(2-(1-Methyl-1H-imidazol-2-yl)ethyl)-1H-pyrazolo[4,3-b]pyridin-3-yl)pyridin-4-yl)-5-(trifluoromethyl)-1,2,4-oxadiazole, and 3-(2-(1-((1-Methyl-1H-pyrazol-4-yl)methyl)-1H-pyrrolo[3,2-c]pyridin-6-yl)pyridin-4-yl)-5-(trifluoromethyl)-1,2,4-oxadiazole, or a salt thereof.

9. A pharmaceutical composition which comprises a compound of claim 1 or a pharmaceutically acceptable salt thereof, and a pharmaceutically acceptable carrier.

10. A method for treating a disease associated with HDAC6, comprising administering a therapeutically effective amount of a compound of claim 1, or a pharmaceutically acceptable salt thereof, to a patient in need thereof.

11. A method for treating a disease selected from cancer, an autoimmune or inflammatory disease, transplant rejection, a ciliopathy, a disease of the nervous system, a mental or behavioral disorder, an infectious disease, a cardiovascular disease, muscle atrophy and cachexia, comprising administering a therapeutically effective amount of a compound of claim 1, or a pharmaceutically acceptable salt thereof, to a patient in need thereof.

12. The method of claim 10, wherein the patient to be treated is a human.

13. The method of claim 10, wherein said disease is a disease of the nervous system.

14. The method of claim 13, wherein said disease is a peripheral neuropathy.

15. The method of claim 13, wherein said disease is a chemotherapy-induced peripheral neuropathy.

16. The method of claim 13, wherein said disease is Charcot-Marie Tooth Disease.

17. The method of claim 13, wherein said disease is amyotrophic lateral sclerosis.

18. The compound of claim 1, wherein the compound has formula (IIIa), or a salt thereof (IIIa)

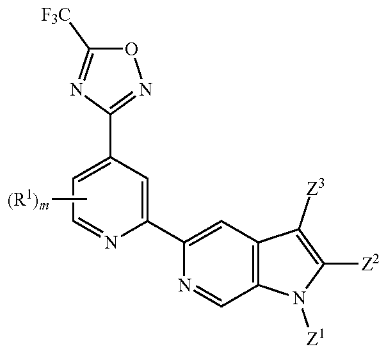

wherein one of $Z^1$, $Z^2$, and $Z^3$ is $R^3$ or H, and the others are independently selected from H and $R^2$.

19. The compound of claim 18, wherein $Z^2$ is $R^3$, wherein $Z^1$ and $Z^3$ are independently selected from H and $R^2$, and wherein $R^3$ is —$CONR^9R^{10}$.

20. The compound of claim 1, which is N,N,1-trimethyl-5-(4-(5-(trifluoromethyl)-1,2,4-oxadiazol-3-yl)pyridin-2-yl)-1H-pyrrolo[2,3-c]pyridine-2-carboxamide, or a salt thereof.

21. The compound of claim 1, which is 3-(2-(1-(2-methoxyethyl)-1H-pyrazolo[4,3-b]pyridin-3-yl)pyridin-4-yl)-5-(trifluoromethyl)-1,2,4-oxadiazole, or a salt thereof.

22. The compound of claim 1, which is 3-(2-(1H-pyrazolo[4,3-b]pyridin-3-yl)pyridin-4-yl)-5-(trifluoromethyl)-1,2,4-oxadiazole, or a salt thereof.

* * * * *